United States Patent
Cooper et al.

(10) Patent No.: US 11,051,794 B2
(45) Date of Patent: Jul. 6, 2021

(54) APPARATUS FOR PITCH AND YAW ROTATION

(71) Applicant: Intuitive Surgical Operations, Inc., Sunnyvale, CA (US)

(72) Inventors: Thomas G. Cooper, Menlo Park, CA (US); Daniel T. Wallace, Redwood City, CA (US); Stacey Chang, Sunnyvale, CA (US); S. Christopher Anderson, San Francisco, CA (US); Dustin Williams, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 171 days.

(21) Appl. No.: 16/162,652

(22) Filed: Oct. 17, 2018

(65) Prior Publication Data
US 2019/0046173 A1  Feb. 14, 2019

Related U.S. Application Data

(60) Continuation of application No. 15/624,344, filed on Jun. 15, 2017, now Pat. No. 10,105,128, which is a
(Continued)

(51) Int. Cl.
*A61B 17/00* (2006.01)
*A61B 34/00* (2016.01)
(Continued)

(52) U.S. Cl.
CPC ........ *A61B 17/00234* (2013.01); *A61B 34/30* (2016.02); *A61B 34/71* (2016.02);
(Continued)

(58) Field of Classification Search
CPC ... A61B 17/00; A61B 17/00234; A61B 17/29; A61B 19/2203; A61B 2017/2908;
(Continued)

(56) References Cited

U.S. PATENT DOCUMENTS 1,418,184 A   5/1922 Trunick
2,681,991 A   6/1954 Marco et al.
(Continued)

FOREIGN PATENT DOCUMENTS

AT    1489 T      9/1982
CH    482439 A   12/1969
(Continued)

OTHER PUBLICATIONS

Adams, Ludwig et al., "Computer-Assisted Surgery," IEEE Computer Graphics & Applications, May 1990, pp. 43-52, vol. 10—Issue 3, IEEE Computer Society Press.
(Continued)

*Primary Examiner* — Vi X Nguyen

(57) ABSTRACT

The present invention is directed to a tool having a wrist mechanism that provides pitch and yaw rotation in such a way that the tool has no singularity in roll, pitch, and yaw. A positively positionable multi-disk wrist mechanism includes a plurality of disks or vertebrae stacked in series. Each vertebra is configured to rotate in pitch or in yaw with respect to each neighboring vertebra. Actuation cables are used to manipulate and control movement of the vertebrae. In specific embodiments, some of the cables are distal cables that extend from a proximal vertebra through one or more intermediate vertebrae to a distal vertebra, while the remaining cables are medial cables that extend from the proximal vertebra to one or more of the intermediate vertebrae. The cables are actuated by a pivoted plate cable actuator mechanism.

6 Claims, 55 Drawing Sheets

Related U.S. Application Data continuation of application No. 14/536,899, filed on Nov. 10, 2014, now Pat. No. 9,717,486, which is a continuation of application No. 13/414,445, filed on Mar. 7, 2012, now Pat. No. 8,911,428, which is a continuation of application No. 12/782,833, filed on May 19, 2010, now Pat. No. 8,142,421, which is a division of application No. 10/980,119, filed on Nov. 1, 2004, now Pat. No. 7,736,356, which is a division of application No. 10/187,248, filed on Jun. 28, 2002, now Pat. No. 6,817,974.

(60) Provisional application No. 60/327,702, filed on Oct. 5, 2001, provisional application No. 60/301,967, filed on Jun. 29, 2001.

(51) Int. Cl.
*A61B 34/30* (2016.01)
*A61B 17/29* (2006.01)
*A61B 1/005* (2006.01)
*A61B 1/008* (2006.01)

(52) U.S. Cl.
CPC .............. *A61B 34/72* (2016.02); *A61B 1/008* (2013.01); *A61B 1/0055* (2013.01); *A61B 1/0057* (2013.01); *A61B 2017/0069* (2013.01); *A61B 2017/00314* (2013.01); *A61B 2017/2908* (2013.01); *A61B 2017/2929* (2013.01); *A61B 2017/2936* (2013.01); *A61B 2034/304* (2016.02); *A61B 2034/305* (2016.02); *A61B 2034/306* (2016.02)

(58) Field of Classification Search
CPC .... A61B 2017/2929; A61B 2017/2936; A61B 19/00; A61B 19/201; A61B 19/203; A61B 19/5244; A61B 34/30; A61B 34/71; A61B 34/72

See application file for complete search history.

(56) References Cited

U.S. PATENT DOCUMENTS

| | | |
|---|---|---|
| 2,815,697 A | 12/1957 | Saunders-Singer |
| 2,901,258 A | 8/1959 | Brandafi |
| 3,060,972 A | 10/1962 | Sheldon |
| 3,145,333 A | 8/1964 | Pardini et al. |
| 3,190,286 A | 6/1965 | Stokes |
| 3,266,059 A | 8/1966 | Stelle |
| 3,268,059 A | 8/1966 | Hill |
| 3,463,329 A | 8/1969 | Gartner |
| 3,557,780 A | 1/1971 | Masaaki |
| 3,628,535 A | 12/1971 | Ostrowsky et al. |
| 3,788,303 A | 1/1974 | Hall |
| 3,818,125 A | 6/1974 | Butterfield |
| 3,921,445 A | 11/1975 | Hill et al. |
| 3,923,166 A | 12/1975 | Fletcher et al. |
| 3,934,201 A | 1/1976 | Majefski |
| 4,038,987 A | 8/1977 | Komiya |
| 4,113,115 A | 9/1978 | Yoshio |
| 4,149,278 A | 4/1979 | Frosch et al. |
| 4,150,326 A | 4/1979 | Engelberger et al. |
| 4,203,430 A | 5/1980 | Takahashi |
| 4,260,319 A | 4/1981 | Motoda et al. |
| 4,264,266 A | 4/1981 | Trechsel |
| 4,281,447 A | 8/1981 | Miller et al. |
| 4,300,362 A | 11/1981 | Lande et al. |
| 4,329,980 A | 5/1982 | Terada |
| 4,332,066 A | 6/1982 | Hailey et al. |
| 4,349,837 A | 9/1982 | Hinds |
| 4,367,998 A | 1/1983 | Causer |
| 4,419,041 A | 12/1983 | Rose |
| 4,483,326 A | 11/1984 | Yamaka et al. |
| 4,486,928 A | 12/1984 | Tucker et al. |
| 4,500,065 A | 2/1985 | Hennekes et al. |
| 4,510,574 A | 4/1985 | Guittet et al. |
| 4,511,305 A | 4/1985 | Kawai et al. |
| 4,512,709 A | 4/1985 | Hennekes et al. |
| 4,562,463 A | 12/1985 | Lipton |
| 4,580,551 A | 4/1986 | Siegmund et al. |
| 4,582,067 A | 4/1986 | Silverstein et al. |
| 4,583,117 A | 4/1986 | Lipton et al. |
| 4,611,888 A | 9/1986 | Prenovitz et al. |
| 4,622,954 A | 11/1986 | Arakawa et al. |
| 4,636,138 A | 1/1987 | Gorman |
| 4,651,201 A | 3/1987 | Schoolman |
| 4,697,577 A | 10/1987 | Forkner |
| 4,706,372 A | 11/1987 | Ferrero et al. |
| 4,708,434 A * | 11/1987 | Tsuno ................ A61B 1/00082 385/118 |
| 4,710,093 A | 12/1987 | Zimmer et al. |
| 4,722,056 A | 1/1988 | Roberts et al. |
| 4,726,355 A | 2/1988 | Okada |
| 4,744,363 A | 5/1988 | Hasson |
| 4,750,475 A | 6/1988 | Yoshihashi |
| 4,751,925 A | 6/1988 | Tontarra |
| 4,762,455 A | 8/1988 | Coughlan et al. |
| 4,766,775 A | 8/1988 | Hodge |
| 4,793,053 A | 12/1988 | Zuccaro et al. |
| 4,806,068 A | 2/1989 | Kohli et al. |
| 4,808,898 A | 2/1989 | Pearson |
| 4,809,747 A | 3/1989 | Choly et al. |
| 4,830,569 A | 5/1989 | Jannborg |
| 4,832,198 A | 5/1989 | Alikhan |
| 4,833,383 A | 5/1989 | Skarr et al. |
| 4,834,069 A | 5/1989 | Umeda |
| 4,837,703 A | 6/1989 | Kakazu et al. |
| 4,837,734 A | 6/1989 | Ichikawa et al. |
| 4,853,874 A | 8/1989 | Iwamoto et al. |
| 4,855,822 A | 8/1989 | Narendra et al. |
| 4,860,215 A | 8/1989 | Seraji |
| 4,862,873 A | 9/1989 | Yajima et al. |
| 4,863,133 A | 9/1989 | Bonnell |
| 4,873,572 A | 10/1989 | Miyazaki et al. |
| 4,899,730 A | 2/1990 | Stennert et al. |
| 4,903,536 A * | 2/1990 | Salisbury, Jr. ........... B25J 9/046 414/7 |
| 4,919,112 A | 4/1990 | Siegmund |
| 4,919,382 A | 4/1990 | Forman |
| 4,922,338 A | 5/1990 | Arpino |
| 4,928,546 A | 5/1990 | Walters |
| 4,941,106 A | 7/1990 | Krieger |
| 4,942,538 A | 7/1990 | Yuan et al. |
| 4,942,539 A | 7/1990 | McGee et al. |
| 4,943,939 A | 7/1990 | Hoover |
| 4,947,702 A | 8/1990 | Kato |
| 4,979,496 A | 12/1990 | Komi |
| 4,979,949 A | 12/1990 | Matsen, III |
| 4,989,253 A | 1/1991 | Liang et al. |
| 4,996,975 A | 3/1991 | Nakamura |
| 5,002,418 A | 3/1991 | McCown et al. |
| 5,005,558 A | 4/1991 | Aomori |
| 5,018,266 A | 5/1991 | Hutchinson et al. |
| 5,020,933 A | 6/1991 | Salvestro et al. |
| 5,029,574 A | 7/1991 | Shimamura et al. |
| 5,045,936 A | 9/1991 | Lobb et al. |
| 5,046,022 A | 9/1991 | Conway et al. |
| 5,053,687 A | 10/1991 | Merlet |
| 5,060,532 A | 10/1991 | Barker |
| 5,062,761 A | 11/1991 | Glachet |
| 5,078,140 A | 1/1992 | Kwoh |
| 5,096,236 A | 3/1992 | Thony |
| 5,141,519 A | 8/1992 | Smith et al. |
| 5,142,930 A | 9/1992 | Allen et al. |
| 5,143,453 A | 9/1992 | Weynant Nee Girones |
| 5,154,717 A | 10/1992 | Matsen, III et al. |
| 5,174,300 A | 12/1992 | Bales et al. |
| 5,179,935 A | 1/1993 | Miyagi |
| 5,182,641 A | 1/1993 | Diner et al. |
| 5,184,601 A | 2/1993 | Putman |
| 5,187,796 A | 2/1993 | Wang et al. |
| 5,209,747 A | 5/1993 | Knoepfler |

(56) References Cited

U.S. PATENT DOCUMENTS

| | | |
|---|---|---|
| 5,217,003 A | 6/1993 | Wilk |
| 5,219,351 A | 6/1993 | Teubner et al. |
| 5,221,283 A | 6/1993 | Chang |
| 5,236,432 A | 8/1993 | Matsen, III et al. |
| 5,239,883 A | 8/1993 | Rosheim |
| 5,253,706 A | 10/1993 | Reid |
| 5,254,130 A | 10/1993 | Poncet et al. |
| 5,255,429 A | 10/1993 | Nishi et al. |
| 5,257,998 A | 11/1993 | Ota et al. |
| 5,260,319 A | 11/1993 | Effland et al. |
| 5,264,266 A | 11/1993 | Yokoyama et al. |
| 5,271,381 A | 12/1993 | Ailinger et al. |
| 5,271,384 A | 12/1993 | McEwen et al. |
| 5,273,039 A | 12/1993 | Fujiwara et al. |
| 5,279,309 A | 1/1994 | Taylor et al. |
| 5,281,220 A | 1/1994 | Blake, III |
| 5,284,130 A | 2/1994 | Ratliff |
| 5,294,209 A | 3/1994 | Naka et al. |
| 5,299,288 A | 3/1994 | Glassman et al. |
| 5,299,559 A | 4/1994 | Bruce et al. |
| 5,305,203 A | 4/1994 | Raab |
| 5,312,212 A | 5/1994 | Naumec |
| 5,313,306 A | 5/1994 | Kuban et al. |
| 5,313,935 A | 5/1994 | Kortenbach et al. |
| 5,321,353 A | 6/1994 | Furness |
| 5,325,866 A | 7/1994 | Krzyzanowski |
| 5,325,886 A | 7/1994 | Klink |
| 5,339,799 A | 8/1994 | Kami et al. |
| 5,341,950 A | 8/1994 | Sinz |
| 5,343,385 A | 8/1994 | Joskowicz et al. |
| 5,351,676 A | 10/1994 | Putman |
| 5,354,314 A | 10/1994 | Hardy et al. |
| 5,355,743 A | 10/1994 | Tesar |
| 5,359,993 A | 11/1994 | Slater et al. |
| 5,368,015 A | 11/1994 | Wilk |
| 5,372,147 A | 12/1994 | Lathrop, Jr. et al. |
| 5,382,885 A | 1/1995 | Salcudean et al. |
| 5,383,888 A | 1/1995 | Zvenyatsky et al. |
| 5,397,323 A | 3/1995 | Taylor et al. |
| 5,399,951 A | 3/1995 | Lavallee et al. |
| 5,400,267 A | 3/1995 | Denen et al. |
| 5,402,801 A | 4/1995 | Taylor |
| 5,403,319 A | 4/1995 | Matsen, III et al. |
| 5,405,344 A | 4/1995 | Williamson et al. |
| 5,410,944 A | 5/1995 | Cushman |
| 5,417,210 A | 5/1995 | Funda et al. |
| 5,423,648 A | 6/1995 | Akeel et al. |
| 5,425,528 A | 6/1995 | Rains et al. |
| 5,427,097 A | 6/1995 | Depp |
| 5,430,643 A | 7/1995 | Seraji |
| 5,441,505 A | 8/1995 | Nakamura |
| 5,448,989 A | 9/1995 | Heckele |
| 5,451,368 A | 9/1995 | Jacob |
| 5,454,827 A | 10/1995 | Aust et al. |
| 5,460,168 A | 10/1995 | Masubuchi et al. |
| 5,474,566 A | 12/1995 | Alesi et al. |
| 5,474,571 A | 12/1995 | Lang |
| 5,479,930 A | 1/1996 | Gruner et al. |
| 5,480,409 A | 1/1996 | Riza |
| 5,499,320 A | 3/1996 | Backes et al. |
| 5,503,320 A | 4/1996 | Webster et al. |
| 5,503,616 A | 4/1996 | Jones |
| 5,515,478 A | 5/1996 | Wang |
| 5,520,678 A | 5/1996 | Heckele et al. |
| 5,524,180 A | 6/1996 | Wang et al. |
| 5,553,198 A | 9/1996 | Wang et al. |
| 5,573,520 A | 11/1996 | Schwartz et al. |
| 5,577,991 A | 11/1996 | Akui et al. |
| 5,582,576 A | 12/1996 | Hori et al. |
| 5,611,813 A | 3/1997 | Lichtman |
| 5,618,294 A | 4/1997 | Aust et al. |
| 5,619,195 A | 4/1997 | Allen et al. |
| 5,624,398 A | 4/1997 | Smith et al. |
| 5,625,576 A | 4/1997 | Massie et al. |
| 5,631,973 A | 5/1997 | Green |
| 5,636,138 A | 6/1997 | Gilbert et al. |
| 5,649,956 A | 7/1997 | Jensen et al. |
| 5,657,429 A | 8/1997 | Wang et al. |
| 5,695,500 A | 12/1997 | Taylor et al. |
| 5,697,889 A | 12/1997 | Slotman et al. |
| 5,697,939 A | 12/1997 | Kubota et al. |
| 5,699,695 A | 12/1997 | Canfield et al. |
| 5,715,729 A | 2/1998 | Toyama et al. |
| 5,737,500 A | 4/1998 | Seraji et al. |
| 5,740,699 A | 4/1998 | Ballantyne et al. |
| 5,748,767 A | 5/1998 | Raab |
| 5,754,741 A | 5/1998 | Wang et al. |
| 5,755,731 A | 5/1998 | Grinberg |
| 5,762,458 A | 6/1998 | Wang et al. |
| 5,776,049 A | 7/1998 | Takahashi |
| 5,784,542 A | 7/1998 | Ohm et al. |
| 5,791,231 A | 8/1998 | Cohn et al. |
| 5,792,135 A | 8/1998 | Madhani et al. |
| 5,797,900 A | 8/1998 | Madhani et al. |
| 5,800,423 A | 9/1998 | Jensen |
| 5,808,665 A | 9/1998 | Green |
| 5,810,715 A * | 9/1998 | Moriyama ......... A61B 1/00078 600/139 |
| 5,810,880 A | 9/1998 | Jensen et al. |
| 5,814,038 A | 9/1998 | Jensen et al. |
| 5,815,640 A | 9/1998 | Wang et al. |
| 5,820,545 A | 10/1998 | Arbter et al. |
| 5,855,553 A | 1/1999 | Tajima et al. |
| 5,855,583 A | 1/1999 | Wang et al. |
| 5,859,934 A | 1/1999 | Green |
| 5,860,912 A | 1/1999 | Chiba |
| 5,864,359 A | 1/1999 | Kazakevich |
| 5,868,760 A | 2/1999 | McGuckin, Jr. |
| 5,876,325 A | 3/1999 | Mizuno et al. |
| 5,878,193 A | 3/1999 | Wang et al. |
| 5,885,288 A | 3/1999 | Aust et al. |
| 5,907,664 A | 5/1999 | Wang et al. |
| 5,908,436 A | 6/1999 | Cuschieri et al. |
| 5,911,036 A | 6/1999 | Wright et al. |
| 5,916,146 A | 6/1999 | Allotta et al. |
| 5,931,832 A | 8/1999 | Jensen |
| 5,938,678 A | 8/1999 | Zirps et al. |
| 5,960,125 A | 9/1999 | Michael et al. |
| 5,971,976 A | 10/1999 | Wang et al. |
| 6,053,907 A | 4/2000 | Zirps |
| 6,071,233 A | 6/2000 | Ishikawa et al. |
| 6,077,287 A | 6/2000 | Taylor et al. |
| 6,116,802 A | 9/2000 | Gueret |
| 6,120,433 A | 9/2000 | Mizuno et al. |
| 6,132,368 A | 10/2000 | Cooper |
| 6,174,280 B1 | 1/2001 | Oneda et al. |
| 6,191,809 B1 | 2/2001 | Hori et al. |
| 6,196,081 B1 | 3/2001 | Yau |
| 6,244,809 B1 | 6/2001 | Wang et al. |
| 6,270,453 B1 | 8/2001 | Sakai |
| 6,296,635 B1 | 10/2001 | Smith et al. |
| 6,306,081 B1 | 10/2001 | Ishikawa et al. |
| 6,307,285 B1 | 10/2001 | Delson et al. |
| 6,312,435 B1 | 11/2001 | Wallace et al. |
| 6,330,837 B1 | 12/2001 | Charles et al. |
| 6,331,181 B1 | 12/2001 | Tierney et al. |
| 6,335,755 B1 | 1/2002 | McLaine et al. |
| 6,394,998 B1 | 5/2002 | Wallace et al. |
| 6,418,811 B1 | 7/2002 | Rosheim |
| 6,424,885 B1 | 7/2002 | Niemeyer et al. |
| 6,425,177 B1 | 7/2002 | Akeel |
| 6,436,107 B1 | 8/2002 | Wang et al. |
| 6,450,948 B1 | 9/2002 | Matsuura et al. |
| 6,451,027 B1 | 9/2002 | Cooper et al. |
| 6,471,637 B1 | 10/2002 | Green et al. |
| 6,491,701 B2 | 12/2002 | Tierney et al. |
| 6,516,681 B1 | 2/2003 | Pierrot et al. |
| 6,522,906 B1 | 2/2003 | Salisbury, Jr. et al. |
| 6,592,572 B1 | 7/2003 | Suzuta |
| 6,658,962 B1 | 12/2003 | Rosheim |
| 6,676,684 B1 | 1/2004 | Morley et al. |
| 6,699,235 B2 | 3/2004 | Wallace et al. |
| 6,743,239 B1 | 6/2004 | Kuehn et al. |
| 6,786,896 B1 | 9/2004 | Madhani et al. |

(56) References Cited

U.S. PATENT DOCUMENTS

| | | |
|---|---|---|
| 6,807,295 B1 | 10/2004 | Ono |
| 6,817,974 B2 | 11/2004 | Cooper et al. |
| 6,858,003 B2 | 2/2005 | Evans et al. |
| 7,066,926 B2 | 6/2006 | Wallace et al. |
| 7,273,488 B2 | 9/2007 | Nakamura et al. |
| 7,320,700 B2 | 1/2008 | Cooper et al. |
| 7,691,098 B2 | 4/2010 | Wallace et al. |
| 7,736,356 B2 | 6/2010 | Cooper et al. |
| 7,862,580 B2 | 1/2011 | Cooper et al. |
| 8,142,421 B2 | 3/2012 | Cooper et al. |
| 8,337,521 B2 | 12/2012 | Cooper et al. |
| 8,690,908 B2 | 4/2014 | Cooper et al. |
| 8,790,243 B2 | 7/2014 | Cooper et al. |
| 8,911,428 B2 | 12/2014 | Cooper et al. |
| 9,005,112 B2 | 4/2015 | Hasser et al. |
| 9,095,317 B2 | 8/2015 | Cooper et al. |
| 9,585,641 B2 | 3/2017 | Cooper et al. |
| 9,717,486 B2 | 8/2017 | Cooper et al. |
| 9,730,572 B2 | 8/2017 | Hasser et al. |
| 10,105,128 B2 | 10/2018 | Cooper et al. |
| 10,506,920 B2 | 12/2019 | Hasser et al. |
| 10,524,868 B2 | 1/2020 | Cooper et al. |
| 2001/0023313 A1 | 9/2001 | Ide |
| 2002/0045888 A1 | 4/2002 | Ramans et al. |
| 2002/0103418 A1 | 8/2002 | Maeda et al. |
| 2002/0107530 A1 | 8/2002 | Sauer et al. |
| 2002/0120178 A1 | 8/2002 | Tartaglia et al. |
| 2003/0028217 A1 | 2/2003 | Nakamura et al. |
| 2004/0158268 A1 | 8/2004 | Danitz et al. |
| 2004/0186345 A1 | 9/2004 | Yang et al. |
| 2004/0236316 A1 | 11/2004 | Danitz et al. |
| 2005/0182298 A1 | 8/2005 | Ikeda et al. |
| 2006/0178556 A1 | 8/2006 | Hasser et al. |
| 2006/0199999 A1 | 9/2006 | Ikeda et al. |
| 2007/0287992 A1 | 12/2007 | Diolaiti et al. |
| 2011/0028991 A1 | 2/2011 | Ikeda et al. |
| 2017/0156804 A1 | 6/2017 | Cooper et al. |
| 2017/0311778 A1 | 11/2017 | Hasser et al. |
| 2020/0107700 A1 | 4/2020 | Hasser et al. |
| 2020/0107892 A1 | 4/2020 | Cooper et al. |

FOREIGN PATENT DOCUMENTS

| | | |
|---|---|---|
| DE | 1766809 B1 | 5/1972 |
| DE | 2819976 A1 | 11/1979 |
| DE | 3008120 A1 | 9/1980 |
| DE | 3309737 A1 | 9/1984 |
| DE | 3806190 | 9/1988 |
| DE | 4138861 | 10/1992 |
| DE | 4234833 A1 | 4/1993 |
| DE | 4136861 | 5/1993 |
| DE | 4442185 A1 | 5/1996 |
| DE | 4213426 | 1/1997 |
| DE | 19813781 A1 | 10/1999 |
| EP | 0009447 A1 | 4/1980 |
| EP | 0239409 A1 | 9/1987 |
| EP | 0291292 A2 | 11/1988 |
| EP | 0595291 A1 | 5/1994 |
| EP | 0612496 A1 | 8/1994 |
| EP | 0623316 A1 | 11/1994 |
| EP | 0626604 A2 | 11/1994 |
| EP | 0764423 A1 | 3/1997 |
| EP | 1575439 B1 | 4/2012 |
| FR | 2460762 A1 | 1/1981 |
| FR | 2593106 B1 | 3/1990 |
| GB | 2040134 A | 8/1980 |
| GB | 2045964 A | 11/1980 |
| GB | 2117732 A | 10/1983 |
| GB | 2295601 A | 6/1996 |
| JP | S609676 A | 1/1985 |
| JP | S62122650 A | 6/1987 |
| JP | S63111114 U | 7/1988 |
| JP | S63315026 A | 12/1988 |
| JP | H04502584 A | 5/1992 |
| JP | H0538342 A | 2/1993 |
| JP | H05184525 A | 7/1993 |
| JP | H05305052 A | 11/1993 |
| JP | H06285010 A | 10/1994 |
| JP | H06343644 A | 12/1994 |
| JP | H07410 A | 1/1995 |
| JP | H07163574 A | 6/1995 |
| JP | H07328016 A | 12/1995 |
| JP | H0871072 A | 3/1996 |
| JP | H08160315 A | 6/1996 |
| JP | H08224247 A | 9/1996 |
| JP | H09288239 A | 11/1997 |
| JP | H10109285 A | 4/1998 |
| JP | H10258024 A | 9/1998 |
| JP | H10277985 A | 10/1998 |
| JP | H1110575 A | 1/1999 |
| JP | H11267095 A | 10/1999 |
| JP | 2001145636 A | 5/2001 |
| JP | 2001161711 A | 6/2001 |
| JP | 2002503131 A | 1/2002 |
| JP | 2002503132 A | 1/2002 |
| JP | 2002282265 A | 10/2002 |
| JP | 2003225201 A | 8/2003 |
| JP | 2003265500 A | 9/2003 |
| WO | WO-8403761 A1 | 9/1984 |
| WO | WO-9216141 A1 | 10/1992 |
| WO | WO-199219147 A1 | 11/1992 |
| WO | WO-9310711 A1 | 6/1993 |
| WO | WO-9313916 A1 | 7/1993 |
| WO | WO-9426167 A1 | 11/1994 |
| WO | WO-9501757 A1 | 1/1995 |
| WO | WO-9516396 A1 | 6/1995 |
| WO | WO-9530964 A1 | 11/1995 |
| WO | WO-9639944 A1 | 12/1996 |
| WO | WO-9723158 A1 | 7/1997 |
| WO | WO-9729690 A1 | 8/1997 |
| WO | WO-9740966 A1 | 11/1997 |
| WO | WO-9856297 A1 | 12/1998 |
| WO | WO-9856299 A1 | 12/1998 |
| WO | WO-9910137 A1 | 3/1999 |
| WO | WO-9950721 A1 | 10/1999 |
| WO | WO-0051486 A1 | 9/2000 |
| WO | WO-0192971 A2 | 12/2001 |
| WO | WO-03001986 A2 | 1/2003 |
| WO | WO-200301987 A2 | 1/2003 |
| WO | WO-2004052171 A2 | 6/2004 |
| WO | WO-2005099560 A1 | 10/2005 |
| WO | WO-2006094242 A1 | 9/2006 |
| WO | WO-2007120353 A2 | 10/2007 |

OTHER PUBLICATIONS

Agency of Industrial Science and Technology, Ministry of International Trade and Industry, Japan, "Introduction to New Project for the National Research Development Program (Large-Scale Project) in FY 1991—Micromachine Technology," 1991, 8 pages.

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1974, pp. 121-136, vol. 2, Springer-Verlag.

Arai, Tatsuo et al., "Bilateral control for manipulators with different configurations," IECON Inn Conference on Industrial Electronics Control and Instrumentation, Oct. 22-26, 1984, pp. 40-45, vol. 1.

Asada Haruhiko et al., "Development of a direct drive arm using high torque brushless motors," Proc. of 1st Int. Symp. on Robotics Research, 1984, pp. 583-599, Chapter 7, MIT Press.

Baker, Daniel R. et al., "On the inverse kinematics of redundant manipulators," The International Journal of Robotics Research Inc, Mar. 21, 1988, pp. 3-21, vol. 7—Issue 2, Sage Publications.

Bejczy, Antal K. et al., "Controlling Remote Manipulators through Kinesthetic Coupling," Computers in Mechanical Engineering, 1983, pp. 48-60, vol. 1—Issue 1.

Blue Cross, Another Pair of Hands for Surgeon, The Blue Cross magazine Perspective, 1972, 3 Pages Total.

Borovoi, A.V., "Stability of a manipulator with force feedback," Izv. AN SSSR Mekhanika Tverdogo Teal, 1990, pp. 37-45, vol. 25—Issue 1, Allerton Press, Inc.

(56) References Cited

OTHER PUBLICATIONS

Burdea, Grigore et al., "Dextrous Telerobotics with Force Feedback—an overview. Part 2: Control and Implementation," Robotica, 1991, pp. 291-298, vol. 9.
Caccavale, Fabrizio et al., "Experiments of kinematic control on a redundant robot manipulator with non-spherical wrist," Laboratory Robotics and Automation, 1996, pp. 25-36, vol. 8—Issue 1.
Chang, Kyong-Sok et al., "Manipulator control at kinematic singularities: A dynamically consistent strategy," IEEE International Conference on Robotics and Automation, 1995, pp. 84-88, vol. 3, IEEE.
Colgate, Edward, J., "Power and Impedance Scaling in Bilateral Manipulation," IEEE International Conference on Robotics and Automation, Sacramento, California, Apr. 1991, pp. 2292-2297, vol. 3, IEEE.
Decision Rejecting the Opposition dated Jul. 7, 2014 for European Application No. 02756362 filed Jun. 28, 2002.
ERCIM News, No. 42, Jul. 2000, Special Theme: Robotics, 60 pages.
European Search Report for Application No. 11002838, dated Apr. 25, 2013, 6 pages.
European Search Report for Application No. EP11002837 dated Apr. 25, 2013, 6 pages.
Extended European Search Report for Application No. 11160272.8, dated Sep. 23, 2016, 9 pages.
Extended European Search Report for Application No. 16162402.8, dated Aug. 17, 2016, 8 pages.
Extended European Search Report for Application No. 16175279.5, dated Oct. 6, 2016, 6 pages.
Extended European Search Report for Application No. EP14150662, dated Jul. 28, 2014, 7 pages.
Extended European Search Report for Application No. EP14193159.2, dated Apr. 25, 2015, 6 pages.
Extended European Search Report for Application No. EP14193162.6, dated Apr. 29, 2015, 7 pages.
Extended European Search Report for Application No. EP14193176.6, dated Apr. 28, 2015, 5 pages.
Extended European Search Report for Application No. EP17188442.2, dated Mar. 28, 2018, 8 pages.
Fisher, Scott S., "Virtual interface environment," IEEE/A1AA 7th Digital Avionics Systems Conference Ft. Worth Texas, 1986, pp. 346-350, IEEE.
Fu, K.S. et al., "Robotics: control, sensing, vision, and intelligence," 1987, pp. 12-76 and 201-265, Ch. 2 & 5, McGraw-Hill Book Company.
Fukuda, Toshio et al., "A new method of master-slave type of teleoperation for a micro-manipulator system," IEEE Microrobots and Teleoperations Workshop, 1987, 5 pages, IEEE.
Funda J., et al., "Constrained Cartesian Motion Control for Teleoperated Surgical Robots," IEEE Transactions on Robotics and Automation, IEEE, Jun. 1996, vol. 12 (3), pp. 453-465.
Furuta, Katsuhisa et al., "Master slave manipulator based on virtual internal model following control concept," IEEE Intl. Conference on Robotics and Automation, 1987, pp. 567-572, vol. 1, IEEE.
Green, Philip, S. et al., "Mobile telepresence surgery," 2nd Annual Intl Symposium on Med. Robotics and Computer Assisted Surgery, Maryland Nov. 1995, pp. 97-103.
Green P.S., et al., "Telepresence Surgery," IEEE Engineering in Medicine and Biology Magazine, IEEE Sevice Center, Pisacataway, NJ, US, May 1, 1995, vol. 14 (3), pp. 324-329, XP000505090.
Guerrouad, Aicha et al., "SMOS: Stereotaxical Microtelemanipulator for Ocular Surgery," IEEE Engineering in Medicine & Biology Society 11th annual international conference, Nov. 9-12, 1989, pp. 879-880, vol. 3, IEEE.
Hannaford, Blake et al., "Experimental and simulation studies of hard contact in force reflecting teleoperation," IEEE International Conference on Robotics and Automation Proceedings, 1988, pp. 584-589, vol. 1, IEEE.
Held, Richard et al., "Telepresence. Time Delay and Adaptation", *, Spatial Displays and Spatial Instruments Proceedings of a Conference sponsored by NASA Ames Research Center and the School of Optometry, Univ. of California, Aug. 31-Sep. 3, 1987, Published 1989, pp. 28-1 through 28-16.
Hill, John W., "Telepresence surgery demonstration system," Robotics and Automation, 1994, pp. 2302-2307, vol. 3, SRI International.
Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.
Inoue, Masao; "Six-Axis bilateral control of an articulated slave manipulator using a Cartesian master manipulator," Advanced robotics, 1990, pp. 139-150, vol. 4—Issue 2, Robotic society of Japan.
International Preliminary Examination Report for Application No. PCT/US02/20884, dated Jul. 13, 2004, 3 pages.
International Preliminary Examination Report for Application No. PCT/US02/20921, dated May 24, 2004, 4 pages.
International Search Report for application No. PCT/US02/20884, dated May 8, 2003, 1 page.
International Search Report for application No. PCT/US02/20921, dated Jun. 17, 2003, 1 page.
International Search Report for Application No. PCT/US03/38462, dated Feb. 18, 2005, 1 page.
International Search Report for application No. PCT/US06/07757, dated Jun. 27, 2006, 3 pages.
Jau, B. M., "Anthropomorphic Remote Manipulator," NASA Tech Briefs, Apr. 1991, p. 92, NASA's Jet Propulsion Laboratory, Pasadena, California.
Kazerooni, H., "Design and analysis of the statically balanced direct-drive robot manipulator," Robotics and Computer-Integrated Manufacturing, 1989, pp. 287-293, vol. 6, Issue 4.
Kazerooni, H. et al., "The Dynamics and Control of a Haptic Interface Device," IEEE Transactions on Robotics and Automation, 1994, pp. 453-464, vol. 10—Issue 4, IEEE.
Kazerooni, H., "Human/Robot Interaction via the Transfer of Power and Information Signals Part I: Dynamics and Control Analysis," IEEE International Conference on Robotics and Automation, 1989, pp. 1632-1640, IEEE.
Khatib. Oussama, "Reduced effective inertia in macro / mini manipulator systems," Proceedings of ACC, 1988, pp. 2140-2147.
Kim, Won S. et al., "A Helmet Mounted Display for Telerobotics," Compcon Spring '88. Thirty-Third IEEE Computer Society International Conference, 1988, pp. 543-547, IEEE.
Kim, Won S. et al., "Active compliance and damping in telemanipulator control," Jet Propulsion Laboratory New technology Report, 1991, pp. 1-14a, vol. 15—Issue 4, JPL & NASA Case No. NPO-1796917466, Item 40.
Kosuge Kazuhiro, et al., "Unified Approach for Teleoperation of Virtual and Real Environment for Skill Based Teleoperation," Proceedings of the IEEE/RSJ/GI International Conference on Intelligent Robots and Systems, 1994, pp. 1242-1247, vol. 2, IEEE.
Kosuge, Kazuhiro et al., "Unified approach for teleoperation of virtual and real environment manipulation based on reference dynamics," IEEE International Conference on Robotics and Automation, 1995, pp. 938-943, IEEE.
Kwoh, Yik, San et al., "A Robot With Improved Absolute Positioning Accuracy for CT Guided Stereotactic Brain Surgery," IEEE Transactions on Biomedical Engineering, Feb. 1988, pp. 153-160, vol. 35—Issue 2, IEEE.
Laika A., "Geregelte Vorschubantriebe Fur Numerisch Gesteuerte Arbeitsmaschinen," Holz als Roh-und Werkstoff, 1984, vol. 42, pp. 461-466.
Madhani, Akhil J., "Design of Teleoperated Surgical Instruments for Minimally Invasive Surgery," Feb. 1998, pp. 1-251.
Madhani, Akhil J. et al., "The black falcon: A teleoperated surgical instrument for minimally invasive surgery," IEEE/RSJ Int. Conf. on Intelligent Robots and Systems (IROS) Victoria B.C. Canada ), 1998, pp. 936-944, vol. 2, IEEE.
Massie, Thomas H. et al., "The PHANTOM Haptic Interface: A Device for Probing Virtual Objects," Proceedings of the ASME Winter Annual Meeting, Symposium on Haptic Interfaces for Virtual Environment and Teleoperator Systems, 1994, 7 pages.

(56) References Cited

OTHER PUBLICATIONS

Matsushima, K. et al., "Servo Micro-Manipulator Tiny-Micro Mark-1," 4th Symposium on Theory and Practice of Robots and Manipulators, 1982, pp. 193-201.
Merlet J.P., "Optimal Design for the Micro Parallel Robot MIPS," Proceedings of the 2002 IEEE, International Conference on Robotics & Automation Washington, DC, May 2002, pp. 1149-1154.
Merlet J.P., Parallel Robots—First Edition (Solid Mechanics and its Applications, Band 74), Kluwer Academic Publishers, 2000, ISBN: 0792363086, 9780792363088.
Mitsuishi, Mamoru et al., "A tele-micro-surgery system with co-located view and operation points and a rotational-force-feedback-free master manipulator," 2nd Annual Intl. Symposium on Medical robotics and Computer Assisted Surgery Baltimore Maryland, Nov. 4-7, 1995, pp. 111-118.
Moyer, Thomas H., "The design for an integrated hand and wrist mechanism," Masters Thesis, Feb. 1992, 106 pages, Massachusetts Institute of Technology.
Neisius B. et al., "Entwicklung eines Manipulators zur endoskopischen Handhabung chirurgischer Effektoren," Nachrichten—Forschungszentrum Karlsruhe, 1995, pp. 173-180.
Neisius B. et al., "Robotic manipulator for endoscopic handling of surgical effectors and cameras," 1st Intl. Symposium on Medical Robotics and Computer Assisted Surgery, 1994, pp. 169-175, vol. 2.
Ng, W.S. et al., "Robotic Surgery, A First-Hand Experience in Transurethral Resection of the Prostate," IEEE Engineering in Medicine and Biology, Mar. 1993, pp. 120-125, vol. 12—Issue 1, IEEE.
Office Action dated Jul. 1, 2014 for Japanese Application No. 2013-138343 filed Jul. 1, 2013, 4 pages.
Office Action dated Jan. 22, 2016 for Japanese Application No. 2015-033632 filed Feb. 24, 2015, 7 pages.
Office Action dated Feb. 28, 2014 for Japanese Application No. 2012-0222926 filed Oct. 5, 2012.
PCT/US06/62385 International Search Report and Written Opinion of the International Searching Authority, dated Mar. 28, 2008, 16 pages.
Peirs J., et al., "A Flexible Distal Tip with Two Degrees of Freedom for Enhanced Dexterity in Endoscopic Robot Surgery," MME'02, The 13th Micromechanics Europe Workshop, Oct. 6-8, 2002, Sinaia, Romania, pp. 271-274.
Jones D. B. et al., Chapter 25,"Next-Generation 3D Videosystems may Improve Laprascopic Task Performance," Interactive Technology and the New Paradigm for Healthcare, 1995, pp. 152-160.
Extended European Search Report for Application No. EP13162794.5, dated Feb. 10, 2017, 7 pages.
Extended European Search Report for Application No. EP13162798.6, dated Feb. 16, 2017, 8 pages.
Michael B. Cohn's Home Page, http://ww-bsac.ees.berkeley.edu/users/michaelc/, downloaded Nov. 1, 1996, p. 1; UC Berkeley/Endorobotics Corporation Surgical Robotics Project Job Openings, http:/www-bsac.eecs.berkeley.edu/users/michaelc/jobs.html, downloaded Nov. 1, 1996, p. 1; and Medical Robotics, http://robotics.eecs.berkeley.edu/~mcenk/medical/, downloaded Nov. 1, 1996, pp. 1-8.
Partial European Search Report for Application No. EP13162796.0, dated Feb. 16, 2017, 6 pages
Thring, M.W., Robots and Telechirs: Manipulators with Memory; Remote Manipulators; Machine Limbs for the Handicapped, Ellis Horwood Limited, England,1983, 79 pages, including Table of Contents, Preface, Chap. 5 (pp. 108-131), Chap. 7 (pp. 194-195, 235), Chap. 8 (pp. 236-287), Chap. 9 (p. 279).
Reboulet C., et al., "Optimal Design of Redundant Parallel Mechanism for Endoscopic Surgery," Proceedings of the 1999 IEEE/RSJ International Conference on Intelligent Robots and Systems, 1999, vol. 3, pp. 1432-1437.
Richter, Ruthann, "Telesurgery may bridge future gaps," Times Tribune, Jan. 24, 1988, pp. A-1 and A-16.
Robodoc, aus Wikipedia, der freien Enzyklopadie, 3 pages, [online], [retrieved Aug. 26, 2013]. Retrieved from the Internet:< URL: http://de.wikipedia.org/wiki/ROBODOC>.
Rosheim, Mark E., Chapter 5: "Pitch-Yaw-Roll Wrists," Robot Wrist Actuators, Wiley & Sons, New York, 1989, pp. 95-206.
Rosheim, Mark E., "Robot Wrist Actuators," John Wiley & Sons, Inc., New York, 1989, pp. 112-114, Figures 5.23-5.26, p. 140, figure 5.54.
Rosheim, Mark E., "Robot Wrist Actuators," Wiley & Sons, New York, 1989.
Salisbury, Kenneth J., "Kinematic and force analysis of articulated hands," Department of Computer Science Stanford University Report No. STAN CS 89 921, 1982, Chapter 9, pp. 67-77.
Sastry, Shankar et al., "Millirobotics for remote minamally invasive surgery," Proceedings of the Intl. Workshop on Some Critical Issues in Robotics, Singapore, Oct. 2-3, 1995, pp. 81-98.
Sastry, Shankar, "MilliRobotics in Minimally Invasive Telesurgery," Internet, http://robotics.eecs.berkeley.edu, 1996, 8 pages.
Spain, Edward H., "Stereo Advantage for a Peg in Hole Task Using a Force Feedback Manipulator," SPIE Stereoscopic Displays and Applications, 1990, pp. 244-254, vol. 1256, IEEE.
Supplementary European Search Report for Application No. EP02756362, dated Jun. 9, 2008, 3 pages.
Supplementary European Search Report for Application No. EP03790301, dated Jul. 2, 2009, 3 pages.
Supplementary Partial European Search Report for Application No. EP02748026, dated Jan. 14, 2011, 5 pages total.
Tachi, Susumu et al., "Tele-Existence Master Slave System for Remote Manipulation (II)," IEEE Conference on Decision and Control Honolulu Hawaii, Dec. 5-7, 1990, pp. 85-90, vol. 1—Issue 6, IEEE.
TASK 2: Miniature end effector—A preliminary design, pp. 32-47, no date.
Taubes, Gary et al., "Surgery in Cyberspace," Discover magazine, Dec. 1994, vol. 15, issue 12, pp. 85-92.
Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.
Trevelyan, James P. et al., "Motion Control for a Sheep Shearing Robot," IEEE Robotics Research Conference, the 1st International Symposium, Carroll, NH, USA., 1983, pp. 175-190, in Robotics Research, MIT Press.
Tsai L.W., "The Mechanics of Serial and Parallel Manipulators", in: Robot Analysis, John Wiley & Sons, Inc., 1999, [retrieved on Jul. 9, 2014]. Retrieved from the Internet:< URL: http://books.google.com.pe/books?id=PK_N9aFZ3ccC&pg=PR3&source=gbs_selected_pages&cad=2#v=onepage&q&f=false>.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Vibet, C., "Properties of Master-Slave Robots," Motor-con, MOTORCON'87, Hannover, Apr. 1987, pp. 309-316.
Wampler C. W., "Inverse Kinematic Functions for Redundant Sherical Wrists," IEEE Transactions on Robotics and Automation, 1989, pp. 106-111, vol. 5—Issue 1, IEEE.
Wampler, Charles W. et al., "Wrist singularities: Theory and practice," The Robotics Review 2, 1992, pp. 173-189, MIT Press.
Wampler, Charles W. II et al., "An Implementation of Inverse Kinematic Functions for Control of a Redundant Wrist," Proc. IEEE International Conference on Robotics and Automation, 1989, vol. 2, pp. 914-919.
Wampler, Charles W., "The Inverse Function Approach to Kinematic Control of Redundant Manipulators," American Control Conference, 1982, pp. 1364-1369, vol. 25.
Written Opinion for Application No. PCT/US06/07757, dated Jun. 27, 2006, 5 pages.
Extended European Search Report for Application No. EP20199958.8 dated Feb. 2, 2021, 07 pages.

* cited by examiner

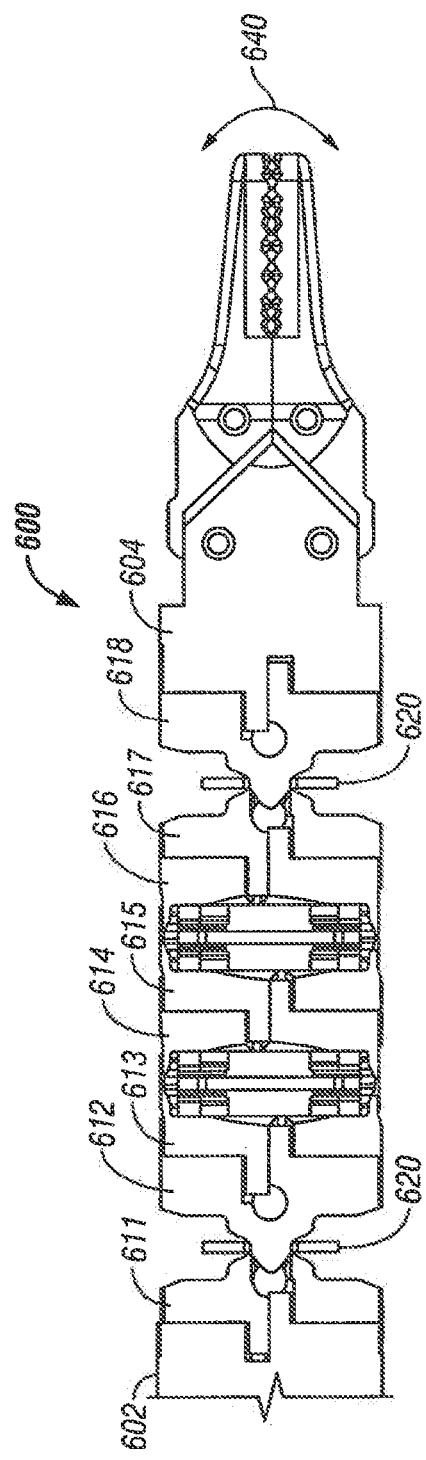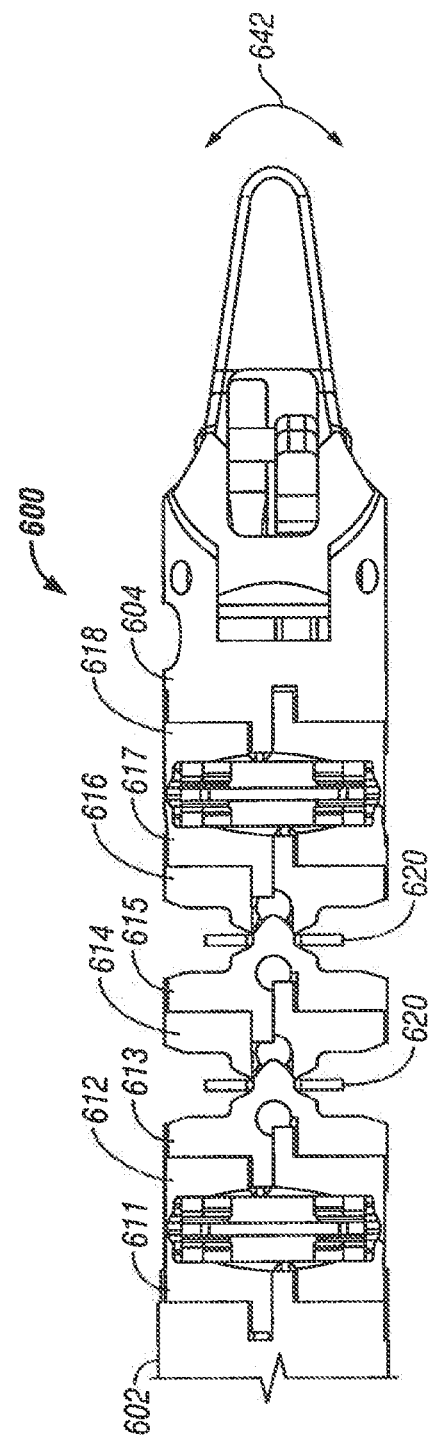

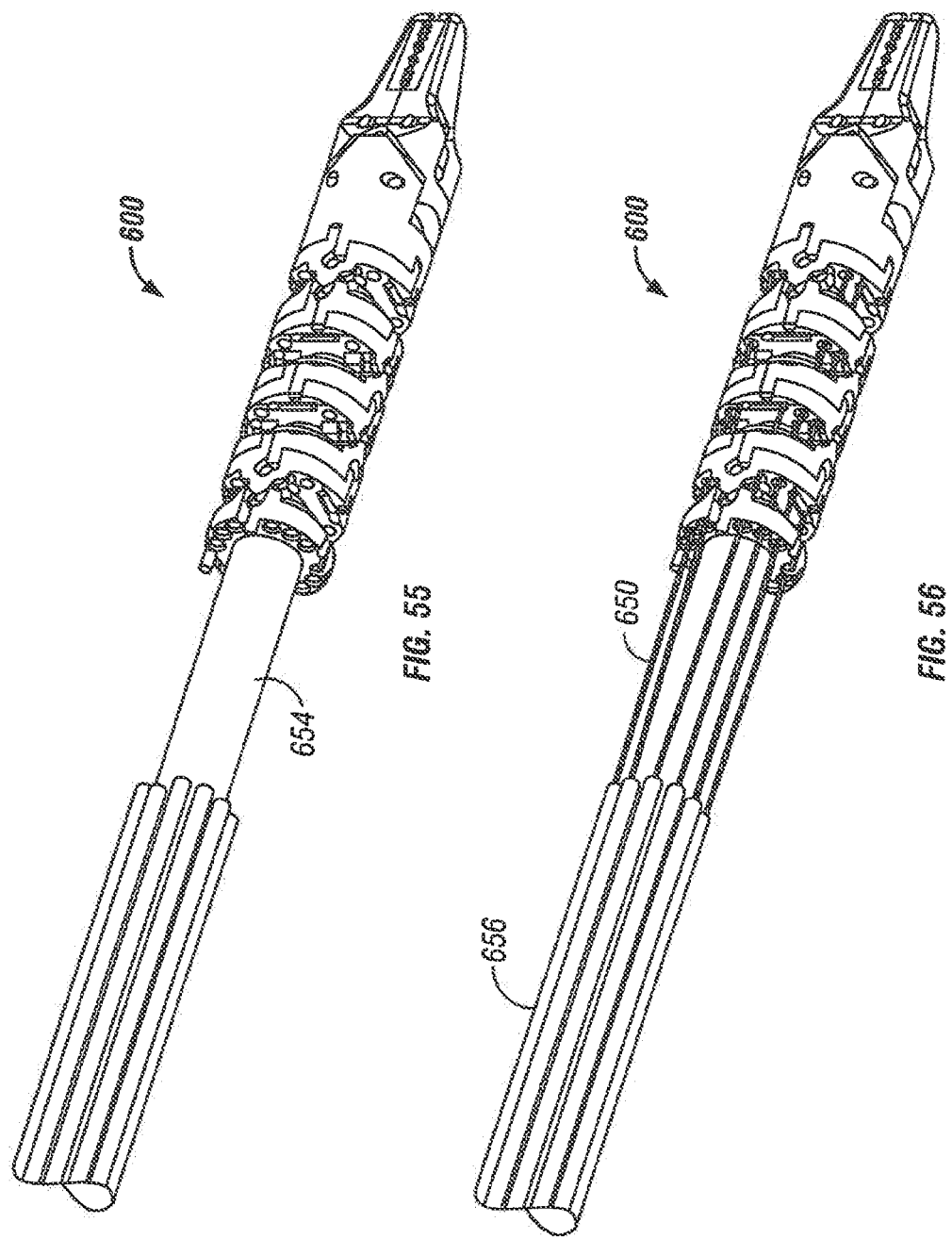

APPARATUS FOR PITCH AND YAW ROTATION

CROSS-REFERENCE TO RELATED APPLICATIONS

This application is a continuation of U.S. patent application Ser. No. 15/624,344, filed Jun. 15, 2017, which is a continuation of U.S. patent application Ser. No. 14/536,899, filed Nov. 10, 2014, now U.S. Pat. No. 9,717,486, which is a continuation of U.S. patent application Ser. No. 13/414,445, filed Mar. 7, 2012, now U.S. Pat. No. 8,911,428, which is a continuation of U.S. patent application Ser. No. 12/782,833, filed May 19, 2010, now U.S. Pat. No. 8,142,421, which is a division of U.S. patent application Ser. No. 10/980,119, filed Nov. 1, 2004, now U.S. Pat. No. 7,736,356, which is a division of U.S. patent application Ser. No. 10/187,248, filed Jun. 28, 2002, now U.S. Pat. No. 6,817,974, which is based on and claims the benefit of U.S. Provisional Patent Application No. 60/301,967, filed Jun. 29, 2001, and U.S. Provisional Patent Application No. 60/327,702, filed Oct. 5, 2001, the entire disclosures of which are incorporated herein by reference.

This application is related to the following patents and patent applications, the full disclosures of which are incorporated herein by reference:

PCT International Application No. PCT/US98/19508, entitled "Robotic Apparatus", filed on Sep. 18, 1998, and published as WO99/50721;

U.S. patent application Ser. No. 09/418,726, entitled "Surgical Robotic Tools, Data Architecture, and Use", filed on Oct. 15, 1999;

U.S. Patent Application No. 60/111,711, entitled "Image Shifting for a Telerobotic System", filed on Dec. 8, 1998;

U.S. patent application Ser. No. 09/378,173, entitled "Stereo Imaging System for Use in Telerobotic System", filed on Aug. 20, 1999;

U.S. patent application Ser. No. 09/398,507, entitled "Master Having Redundant Degrees of Freedom", filed on Sep. 17, 1999;

U.S. application Ser. No. 09/399,457, entitled "Cooperative Minimally Invasive Telesurgery System", filed on Sep. 17, 1999;

U.S. patent application Ser. No. 09/373,678, entitled "Camera Referenced Control in a Minimally Invasive Surgical Apparatus", filed on Aug. 13, 1999;

U.S. patent Application Ser. No. 09/398,958, entitled "Surgical Tools for Use in Minimally Invasive Telesurgical Applications", filed on Sep. 17, 1999; and U.S. Pat. No. 5,808,665, entitled "Endoscopic Surgical Instrument and Method for Use", issued on Sep. 15, 1998.

BACKGROUND OF THE INVENTION

The present invention relates generally to surgical tools and, more particularly, to various wrist mechanisms in surgical tools for performing robotic surgery.

Advances in minimally invasive surgical technology could dramatically increase the number of surgeries performed in a minimally invasive manner Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work may also be reduced with minimally invasive surgery.

The most common form of minimally invasive surgery may be endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments. The laparoscopic surgical instruments generally include a laparoscope (for viewing the surgical field) and working tools. The working tools are similar to those used in conventional (open) surgery, except that the working end or end effector of each tool is separated from its handle by an extension tube. As used herein, the term "end effector" means the actual working part of the surgical instrument and can include clamps, graspers, scissors, staplers, and needle holders, for example. To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy and the like.

There are many disadvantages relating to current minimally invasive surgical (MIS) technology. For example, existing MIS instruments deny the surgeon the flexibility of tool placement found in open surgery. Most current laparoscopic tools have rigid shafts, so that it can be difficult to approach the worksite through the small incision. Additionally, the length and construction of many endoscopic instruments reduces the surgeon's ability to feel forces exerted by tissues and organs on the end effector of the associated tool. The lack of dexterity and sensitivity of endoscopic tools is a major impediment to the expansion of minimally invasive surgery.

Minimally invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a computer workstation. While viewing a three-dimensional image of the surgical site on a suitable viewer or display, the surgeon performs the surgical procedures on the patient by manipulating master input or control devices of the workstation. The master controls the motion of a servomechanically operated surgical instrument. During the surgical procedure, the telesurgical system can provide mechanical actuation and control of a variety of surgical instruments or tools having end effectors such as, e.g., tissue graspers, needle drivers, or the like, that perform various functions for the surgeon, e.g., holding or driving a needle, grasping a blood vessel, or dissecting tissue, or the like, in response to manipulation of the master control devices.

Some surgical tools employ a roll-pitch-yaw mechanism for providing three degrees of rotational movement to an end effector around three perpendicular axes. The pitch and yaw rotations are typically provided by a wrist mechanism coupled between a shaft of the tool and an end effector, and the roll rotation is typically provided by rotation of the shaft. At about 90° pitch, the yaw and roll rotational movements overlap, resulting in the loss of one degree of rotational movement, referred to as a singularity.

BRIEF SUMMARY OF THE INVENTION

The present invention is directed to alternative embodiments of a tool having a wrist mechanism that provides pitch and yaw rotation in such a way that the tool has no singularity in roll, pitch, and yaw. In one preferred embodiment, a wrist mechanism includes a plurality of disks or vertebrae stacked or coupled in series. Typically the most proximal vertebrae or disk of the stack is coupled to a proximal end member segment, such as the working end of a tool or instrument shaft; and the most distal vertebrae or disk is coupled to a distal end member segment, such as an end-effector or end-effector support member. Each disk is configured to rotate in at least one degree of freedom or DOF (e.g., in pitch or in yaw) with respect to each neighboring disk or end member.

In general, in the discussion herein, the term disk or vertebrae may include any proximal or distal end members, unless the context indicates reference to an intermediate segment disposed between the proximal and distal end members. Likewise, the terms disk or vertebrae will be used interchangeably herein to refer to the segment member or segment subassembly, it being understood that the wrist mechanisms having aspects of the invention may include segment members or segment subassemblies of alternative shapes and configurations, which are not necessarily disk-like in general appearance.

Actuation cables or tendon elements are used to manipulate and control movement of the disks, so as to effect movement of the wrist mechanism. The wrist mechanism resembles in some respects tendon-actuated steerable members such as are used in gastroscopes and similar medical instruments. However, multi-disk wrist mechanisms having aspects of the invention may include a number of novel aspects. For example, a wrist embodiment may be positively positionable, and provides that each disk rotates through a positively determinable angle and orientation. For this reason, this embodiment is called a positively positionable multi-disk wrist (PPMD wrist).

In some of the exemplary embodiments having aspects of the invention, each disk is configured to rotate with respect to a neighboring disk by a nonattached contact. As used herein, a nonattached contact refers to a contact that is not attached or joined by a fastener, a pivot pin, or another joining member. The disks maintain contact with each other by, for example, the tension of the actuation cables. The disks are free to separate upon release of the tension of the actuation cables. A nonattached contact may involve rolling and/or sliding between the disks, and/or between a disk and an adjacent distal or proximal wrist portion.

As is described below with respect to particular embodiments, shaped contact surfaces may be included such that nonattached rolling contact may permit pivoting of the adjacent disks, while balancing the amount of cable motion on opposite sides of the disks. In addition, the nonattached contact aspect of the these exemplary embodiments promotes convenient, simplified manufacturing and assembly processes and reduced part count, which is particularly useful in embodiments having a small overall wrist diameter.

It is to be understood that alternative embodiments having aspects of the invention may have one or more adjacent disks pivotally attached to one another and/or to a distal or proximal wrist portion in the same or substantially similar configurations by employing one or more fastener devices such as pins, rivets, bushings and the like.

Additional embodiments are described which achieve a cable-balancing configuration by inclusion of one or more inter-disk struts having radial plugs which engage the adjacent disks (or disk and adjacent proximal or distal wrist portion). Alternative configurations of the intermediate strut and radial plugs may provide a nonattached connection or an attached connection.

In certain embodiments, some of the cables are distal cables that extend from a proximal disk through at least one intermediate disk to a terminal connection to a distal disk. The remaining cables are medial cables that extend from the proximal disk to a terminal connection to a middle disk. The cables are actuated by a cable actuator assembly arranged to move each cable so as to deflect the wrist mechanism. In one exemplary embodiment, the cable actuator assembly may include a gimbaled cable actuator plate. The actuator plate includes a plurality of small radius holes or grooves for receiving the medial cables and a plurality of large radius holes or grooves for receiving the distal cables. The holes or grooves restrain the medial cables to a small radius of motion (e.g., ½ R) and the distal cables to a large radius of motion (R), so that the medial cables to the medial disk move a smaller distance (e.g., only half as far) compared to the distal cables to the distal disk, for a given gimbal motion or rotation relative to the particular cable. Note that for alternative embodiments having more than one intermediate cable termination segment, the cable actuator may have a plurality of sets of holes at selected radii (e.g., R, ⅔ R, and ⅓ R). The wrist embodiments described are particularly suitable for robotic surgical systems, although they may be included in manually operated endoscopic tools.

Embodiments including a cable actuator assembly having aspects of the invention provide to the simultaneous actuation of a substantial plurality of cables, and provide for a predetermined proportionality of motion of a plurality of distinct cable sets. This capability is provided with a simple, inexpensive structure which avoids highly complex control mechanisms. As described further below, for a given total cross-sectional area in each cable set and a given overall disk diameter, a mechanically redundant number of cables permits the cable diameter to be smaller, permits increasing the moment arm or mechanical advantage of the cables, and permits a larger unobstructed longitudinal center lumen along the centerline of the disks. These advantages are particularly useful in wrist members built to achieve the very small overall diameter such as are currently used in endoscopic surgery.

In some embodiments, a grip actuation mechanism is provided for operating a gripping end effector. When cables are used to manipulate the end effector, the grip actuation mechanism may include a grip cable actuator disposed in a tool or instrument proximal base or "back end." The path length of a grip actuation cable may tend to vary in length during bending of the wrist in the event that cable paths do not coincide with the neutral axis. The change in cable path lengths may be accounted for in the back end mechanism used to secure and control the cables. This may be achieved by including a cable tension regulating device in the grip actuation mechanism, so as to decouple the control of the end effector such as grip jaws from the bending of the wrist.

In specific embodiments, the back end mechanism is configured to allow for the replacement of the end effector, the wrist, and the shaft of the surgical instrument with relative ease.

In accordance with an aspect of the present invention, a minimally invasive surgical instrument comprises an elongate shaft having a working end, a proximal end, and a shaft axis between the working end and the proximal end. A wrist member has a proximal portion connected to the working end. An end effector is connected to a distal portion of the wrist member. The wrist member comprises at least three vertebrae connected in series between the working end of the elongate shaft and the end effector. The vertebrae include a proximal vertebra connected to the working end of the elongate shaft and a distal vertebra connected to the end effector.

Each vertebra is pivotable relative to an adjacent vertebra by a pivotal connection, which may employ a nonattached (or alternatively an attached) contact. At least one of the vertebrae is pivotable relative to an adjacent vertebra by a pitch contact around a pitch axis which is nonparallel to the shaft axis. At least one of the vertebrae is pivotable relative to an adjacent vertebra by another contact around a second axis which is nonparallel to the shaft axis and nonparallel to the pitch axis.

In accordance with another aspect of this invention, a minimally invasive surgical instrument comprises an elongate shaft having a working end, a proximal end, and a shaft axis between the working end and the proximal end. A wrist member has a proximal portion or proximal end member connected to the working end, and a distal portion or distal end member connected to an end effector. The wrist member comprises at least three vertebrae connected in series between the working end of the elongate shaft and an end effector.

The vertebrae include a proximal vertebra connected to the working end of the elongate shaft and a distal vertebra connected to the end effector. Each vertebra is pivotable relative to an adjacent vertebra by a pivotable vertebral joint. At least one of the vertebrae is pivotable relative to an adjacent vertebra by a pitch joint around a pitch axis which is nonparallel to the shaft axis. At least one of the vertebrae is pivotable relative to an adjacent vertebra by a yaw joint around a yaw axis which is nonparallel to the shaft axis and perpendicular to the pitch axis. An end effector is connected to a distal portion of the wrist member. A plurality of cables are coupled with the vertebrae to move the vertebrae relative to each other. The plurality of cables include at least one distal cable coupled with the terminating at the distal vertebra and extending proximally to a cable actuator member, and at least one intermediate cable coupled with and terminating at an intermediate vertebra disposed between the proximal vertebra and the distal vertebra and extending to the cable actuator member. The cable actuator member is configured to adjust positions of the vertebrae by moving the distal cable by a distal displacement and the intermediate cable by an intermediate displacement shorter than the distal displacement.

In some embodiments, a ratio of each intermediate displacement to the distal displacement is generally proportional to a ratio of a distance from the proximal vertebra to the intermediate vertebra to which the intermediate cable is connected and a distance from the proximal vertebra to the distal vertebra to which the distal cable is connected.

In accordance with another aspect of the invention, a method of performing minimally invasive endoscopic surgery in a body cavity of a patient comprises introducing an elongate shaft having a working end into the cavity. The elongate shaft has a proximal end and a shaft axis between the working end and the proximal end. A wrist member comprises at least three vertebrae connected in series between the working end of the elongate shaft and the end effector. The vertebrae include a proximal vertebra connected to the working end of the elongate shaft and a distal vertebra connected to the end effector. Each vertebra is pivotable relative to an adjacent vertebra by a pivotal coupling, which may employ a nonattached contact. An end effector is connected to a distal portion of the wrist member. The end effector is positioned by rotating the wrist member to pivot at least one vertebra relative to an adjacent vertebra by a pivotal pitch coupling around a pitch axis which is nonparallel to the shaft axis. The end effector is repositioned by rotating the wrist member to pivot at least one vertebra relative to an adjacent vertebra by another pivotal coupling around a second axis which is nonparallel to the shaft axis and nonparallel to the pitch axis.

In accordance with another aspect of the present invention, a minimally invasive surgical instrument has an end effector which comprises a grip support having a left pivot and a right pivot. A left jaw is rotatable around the left pivot of the grip support and a right jaw is rotatable around the right pivot of the grip support. A left slider pin is attached to the left jaw and spaced from the left pivot pin, and a right slider pin is attached to the right jaw and spaced from the right pivot pin. A slotted member includes a left slider pin slot in which the left slider pin is slidable to move the left jaw between an open position and a closed position, and a right slider pin slot in which the right slider pin is slidable to move the right jaw between an open position and a closed position. A slider pin actuator is movable relative to the slotted member to cause the left slider pin to slide in the left slider pin slot and the right slider pin to slide in the right slider pin slot, to move the left jaw and the right jaw between the open position and the closed position.

In accordance with another aspect of the present invention, a method of performing minimally invasive endoscopic surgery in a body cavity of a patient comprises providing a tool comprising an elongate shaft having a working end coupled with an end effector, a proximal end, and a shaft axis between the working end and the proximal end. The end effector includes a grip support having a left pivot and a right pivot; a left jaw rotatable around the left pivot of the grip support and a right jaw rotatable around the right pivot of the grip support, a left slider pin attached to the left jaw and spaced from the left pivot pin, a right slider pin attached to the right jaw and spaced from the right pivot pin; and a slotted member including a left slider pin slot in which the left slider pin is slidable to move the left jaw between an open position and a closed position, and a right slider pin slot in which the right slider pin is slidable to move the right jaw between an open position and a closed position. The method further comprises introducing the end effector into a surgical site; and moving the left slider pin to slide in the left slider pin slot and the right slider pin to slide in the right slider pin slot, to move the left jaw and the right jaw between the open position and the closed position.

According to another aspect, a medical instrument comprises a base shaft having a working end, a proximal end, and a shaft axis between the working end and the proximal end. A segmented wrist member comprises a plurality of spaced-apart segment vertebrae disposed sequentially adjacent to one another along a wrist longitudinal line. The plurality of vertebrae include a proximal vertebra connected to the shaft working end, a distal vertebra supporting an end effector, and at least one intermediate vertebra disposed between the proximal vertebra and the distal vertebra, the at least one intermediate vertebrae being connected to each adjacent vertebra by a pivotally movable segment coupling.

Each segment coupling has a coupling axis nonparallel to the wrist longitudinal line. At least two of the coupling axes are non-parallel to one another. At least one of the intermediate vertebrae is a medial vertebra. A plurality of movable tendon elements are disposed generally longitudinally with respect to the shaft and wrist member. The tendon elements each have a proximal portion, and have a distal portion connected to one of the distal vertebra and the medial vertebra so as to pivotally actuate the connected vertebra. At least one of the tendons is connected to the at least one medial vertebra and at least one of the tendons is connected to the distal vertebra. A tendon actuation mechanism is drivingly coupled to the tendons and configured to controllably move at least selected ones of the plurality of tendons so as to pivotally actuate the plurality of connected vertebrae to laterally bend the wrist member with respect to the shaft.

Another aspect is directed to a tendon actuating assembly for a surgical instrument, wherein the instrument includes a shaft-like member having a distal working end for insertion into a patient's body through an aperture, and wherein the working end includes at least one distal moveable member arranged to be actuated by at least one of a plurality of movable tendon element. The actuating assembly comprises a tendon actuator member which is configured to be movable to at least pivot in one degree of freedom, and which includes a plurality of tendon engagement portions. Each engagement portion is drivingly couplable to at least one of the plurality of tendons. A drive mechanism is drivingly coupled to the actuator member so as to controllably pivot the actuator member in the at least one degree of freedom, so as to move at least one of the tendons relative to the shaft-like member so as to actuate the distal moveable member.

In another aspect, a minimally invasive surgical instrument comprises a shaft having a working end, a proximal end, and a shaft axis between the working end and the proximal end. A segmented wrist member comprises a plurality of spaced-apart segment vertebrae disposed sequentially adjacent to one another along a wrist longitudinal line. The plurality of vertebrae include a proximal vertebra connected to the shaft working end, a distal vertebra supporting an end effector, and at least one intermediate vertebra disposed between the proximal vertebra and the distal vertebra. The at least one intermediate vertebrae is connected to each adjacent vertebra by a pivotally movable segment coupling. Each segment coupling has a coupling axis nonparallel to the wrist longitudinal line. At least two of the coupling axes are non-parallel to one another. The movable segment couplings include at least one spring-like element arranged to regulate the pivotal motion of at least one adjacent vertebra. A plurality of movable tendon elements are disposed generally longitudinally with respect to the shaft and wrist member. The tendon elements each have a proximal portion, and a distal portion connected to the distal vertebra so as to pivotally actuate the distal vertebra. A tendon actuation mechanism is drivingly coupled to the tendons and configured to controllably move at least one of the plurality of tendons so as to pivotally actuate the plurality of connected vertebrae to laterally bend the wrist member with respect to the shaft.

Another aspect is directed a segment pivoted coupling mechanism for pivotally coupling two adjacent segment vertebrae of a multi-segment flexible member of a medical instrument, wherein the two adjacent segments have bending direction with respect to one another, and wherein the flexible member has at least one neutral bending axis. The instrument includes at least two movable actuation tendon passing through at least two apertures in each adjacent vertebrae, wherein the at least two apertures in each of the vertebra are spaced apart on opposite sides of the neutral axis with respect to the pivot direction, and wherein openings of the apertures are disposed one adjacent surfaces of the two vertebrae so as to generally define an aperture plane. The coupling mechanism comprises at least one inter-vertebral engagement element coupled to each of the vertebrae, the element pivotally engaging the vertebrae so as to define at least two spaced-apart parallel cooperating pivot axes, each one of the pivot axes being aligned generally within the aperture plane of a respective one of the adjacent vertebra, so as to provide that each vertebra is pivotally movable about its respective pivot axis, so as to balance the motion of the tendons on opposite sides of the neutral axis when the flexible member is deflected in the bending direction.

BRIEF DESCRIPTION OF THE DRAWINGS

FIGS. 53 and 54 are elevational views of the PPMD wrist of FIG. 51;

FIGS. 55 and 56 are perspective views illustrating the cable connections for the PPMD wrist of FIG. 51;

DETAILED DESCRIPTION OF THE INVENTION

As used herein, "end effector" refers to an actual working distal part that is manipulable by means of the wrist member for a medical function, e.g., for effecting a predetermined treatment of a target tissue. For instance, some end effectors have a single working member such as a scalpel, a blade, or an electrode. Other end effectors have a pair or plurality of working members such as forceps, graspers, scissors, or clip appliers, for example. In certain embodiments, the disks or vertebrae are configured to have openings which collectively define a longitudinal lumen or space along the wrist, providing a conduit for any one of a number of alternative elements or instrumentalities associated with the operation of an end effector. Examples include conductors for electrically activated end effectors (e.g., electrosurgical electrodes; transducers, sensors, and the like); conduits for fluids, gases or solids (e.g., for suction, insufflation, irrigation, treatment fluids, accessory introduction, biopsy extraction and the like); mechanical elements for actuating moving end effector members (e.g., cables, flexible elements or articulated elements for operating grips, forceps, scissors); wave guides; sonic conduction elements; fiberoptic elements; and the like. Such a longitudinal conduit may be provided with a liner, insulator or guide element such as a elastic polymer tube; spiral wire wound tube or the like.

As used herein, the terms "surgical instrument", "instrument", "surgical tool", or "tool" refer to a member having a working end which carries one or more end effectors to be introduced into a surgical site in a cavity of a patient, and is actuatable from outside the cavity to manipulate the end effector(s) for effecting a desired treatment or medical function of a target tissue in the surgical site. The instrument or tool typically includes a shaft carrying the end effector(s) at a distal end, and is preferably servomechanically actuated by a telesurgical system for performing functions such as holding or driving a needle, grasping a blood vessel, and dissecting tissue.

A. Gastroscope Style Wrist

A gastroscope style wrist has a plurality of vertebrae stacked one on top of another with alternating yaw (Y) and pitch (P) axes. For instance, an example of a gastroscope-style wrist may include twelve vertebrae. Such a wrist typically bends in a relatively long arc. The vertebrae are held together and manipulated by a plurality of cables. The use of four or more cables allows the angle of one end of the wrist to be determined when moved with respect to the other end of the wrist. Accessories can be conveniently delivered through the middle opening of the wrist. The wrist can be articulated to move continuously to have orientation in a wide range of angles (in roll, pitch, and yaw) with good control and no singularity.

Figure 1:
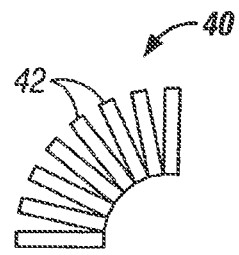
FIG. 1 is an elevational view schematically illustrating the rotation of a gastroscope-style wrist.
Figure 2:
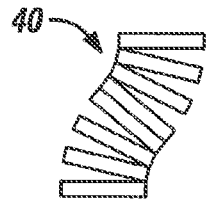
FIG. 2 is an elevational view schematically illustrating an S-shape configuration of the gastroscope-style wrist of FIG. 1.

FIGS. 1 and 2 show a typical prior art gastroscope style flexible wrist-like multi-segment member having a plurality of vertebrae or disks coupled in series in alternating yaw and pitch pivotal arrangement (YPYP . . . Y). FIG. 1 shows the rotation of a gastroscope-style wrist 40 having vertebrae 42, preferably rotating at generally uniform angles between neighboring vertebrae 42. On the other hand, when pitch and yaw forces are applied, the gastroscope-style wrist can take on an S shape with two arcs, as seen in FIG. 2. In addition, backlash can be a problem when the angles between neighboring vertebrae vary widely along the stack. It may be seen that, in operation, the angles of yaw and pitch between adjacent segments may typically take a range of non-uniform, or indeterminate values during bending. Thus, a multi-segment wrist or flexible member may exhibit unpredictable or only partially controlled behavior in response to tendon actuation inputs. Among other things, this can reduce the bending precision, repeatability and useful strength of the flexible member.

Figure 3:
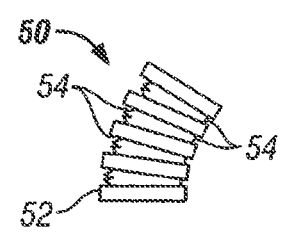
FIG. 3 is an elevational view schematically illustrating a gastroscope-style wrist having vertebrae connected by springs in accordance with an embodiment of the present invention.

One way to minimize backlash and avoid the S-shape configuration is to provide springs 54 between the vertebrae 52 of the wrist 50, as schematically illustrated in FIG. 3. The springs 54 help keep the angles between the vertebrae 52 relatively uniform during rotation of the stack to minimize backlash. The springs 54 also stiffen the wrist 50 and stabilize the rotation to avoid the S-shape configuration.

Figure 4:
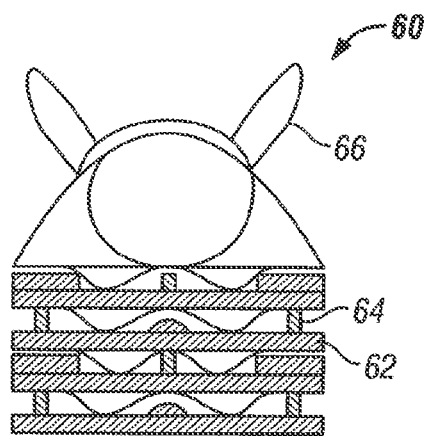
FIG. 4 is a partial cross-sectional view of a gastroscope-style wrist having vertebrae connected by wave springs according to an embodiment of the invention.

As shown in the wrist 60 of FIG. 4, one type of spring that can be connected between the vertebrae 62 is a wave spring 64, which has the feature of providing a high spring force at a low profile. FIG. 4 also shows an end effector in the form of a scissor or forcep mechanism 66. Actuation members such as cables or pulleys for actuating the mechanism 66 may conveniently extend through the middle opening of the wrist 60. The middle opening or lumen allows other items to be passed therethrough.

The wrist 60 is singularity free, and can be designed to bend as much as 360° if desired. The wrist 60 is versatile, and can be used for irrigation, imaging with either fiberoptics or the wires to a CCD passing through the lumen, and the like. The wrist 60 may be used as a delivery device with a working channel. For instance, the surgical instrument with the wrist 60 can be positioned by the surgeon, and hand-operated catheter-style or gastroenterology instruments can be delivered to the surgical site through the working channel for biopsies.

Note that in FIGS. 1-4, (and generally elsewhere herein) the distinction between yaw and pitch may be arbitrary as terms of generalized description of a multi-segment wrist or flexible member, the Y and P axes typically being generally perpendicular to a longitudinal centerline of the member and also typically generally perpendicular to each other. Note, however, that various alternative embodiments having aspects of the invention are feasible having Y and P axes which are not generally perpendicular to a centerline and/or not generally perpendicular to one another. Likewise, a simplified member may be useful while having only a single degree of freedom in bending motion (Y or P).

B. Positively Positionable Multi-Disk Wrist (PPMD Wrist)

A constant velocity or PPMD wrist also has a plurality of vertebrae or disks stacked one on top of another in a series of pivotally coupled engagements and manipulated by cables. In one five-disk embodiment (the disk count including end members), to prevent the S-shape configuration, one set of the cables (distal cables) extend to and terminate at the last vertebrae or distal end disk at the distal end of the wrist, while the remaining set of cables (medial cables) extend to and terminate at a middle disk. By terminating a medial set of cables at the medial disk, and terminating second distal set of cables at the distal disk, all pivotal degrees of freedom of the five disk sequence may be determinately controlled by cable actuators. There is no substantial uncertainty of wrist member shape or position for any given combination of cable actuations. This is the property implied by the term "positively positionable", and which eliminates the cause of S-curve bending or unpredictable bending as described above with respect to FIGS. 1-2).

Note that medial cable set of the PPMD wrist will move a shorter distance than the distal set, for a given overall wrist motion (e.g., half as far). The cable actuator mechanism, examples of which are described further below, provides for this differential motion. Note also, that while the examples shown generally include a plurality of disks or segments which are similarly or identically sized, they need not be. Thus, where adjacent segments have different sizes, the scale of motion between the medial set(s) and the distal set may differ from the examples shown.

In certain preferred embodiments, one of a yaw (Y) or pitch (P) coupling is repeated in two consecutive segments. Thus, for the an exemplary sequence of four couplings between the 5 disk segments, the coupling sequence may be YPPY or PYYP, and medial segment disk (number 3 of 5) is bounded by two Y or two P couplings. This arrangement has the property that permits a "constant velocity" rolling motion in a "roll, pitch, yaw" type instrument distal end. In other words, in the event that the instrument distal portion (shaft/wrist/end effector) is rotated axially about the centerline while the wrist is bent and while the end effector is maintained at a given location and pointing angle (analogous to the operation of a flexible-shaft screw driver), both end effector and instrument shaft will rotate at the same instantaneous angular velocity.

This property "constant velocity" may simplify control algorithms for a dexterous surgical manipulation instrument, and produce smoother operation characteristics. Note that this coupling sequence is quite distinct from the alternating YPYP . . . coupling arrangement of the prior art gastroscope style wrist shown in FIGS. 1 and 2, which includes a strictly alternating sequence of yaw and pitch axes.

In an exemplary embodiment shown in FIGS. 5-8, the wrist 70 has five disks 72-76 stacked with pitch, yaw, yaw, and pitch joints (the disk count including proximal and distal end member disks). The disks are annular and form a hollow center or lumen. Each disk has a plurality of apertures 78 for passing through actuation cables. To lower the forces on each cable, sixteen cables are used. Eight distal cables 80 extend to the fifth disk 76 at the distal end; and eight medial cables 82 extend to the third disk 74 in the middle. The number of cables may change in other embodiments, although a minimum of three cables (or four in a symmetrical arrangement), more desirably six or eight cables, are used. The number and size of cables are limited by the space available around the disks. In one embodiment, the inner diameter of each disk is about 3 mm, the outer diameter is about 2 mm, and the apertures for passing through the cables are about 0.5 mm in diameter. For a given total cross-sectional area in each cable set (medial or distal) and a given overall disk diameter, a mechanically redundant number of cables permits the cable diameter to be smaller, and thus permits the cables to terminate at apertures positioned farther outward radially from the center line of the medial or distal disk, thus increasing the moment arm or mechanical advantage of applied cable forces. In addition, the resulting smaller cable diameter permits a larger unobstructed longitudinal center lumen along the centerline of the disks. These advantages are particularly useful in wrist members built to achieve the very small overall diameter of the insertable instrument portion (about 5 mm or less) that is currently favored for the endoscopic surgery.

Figure 5:
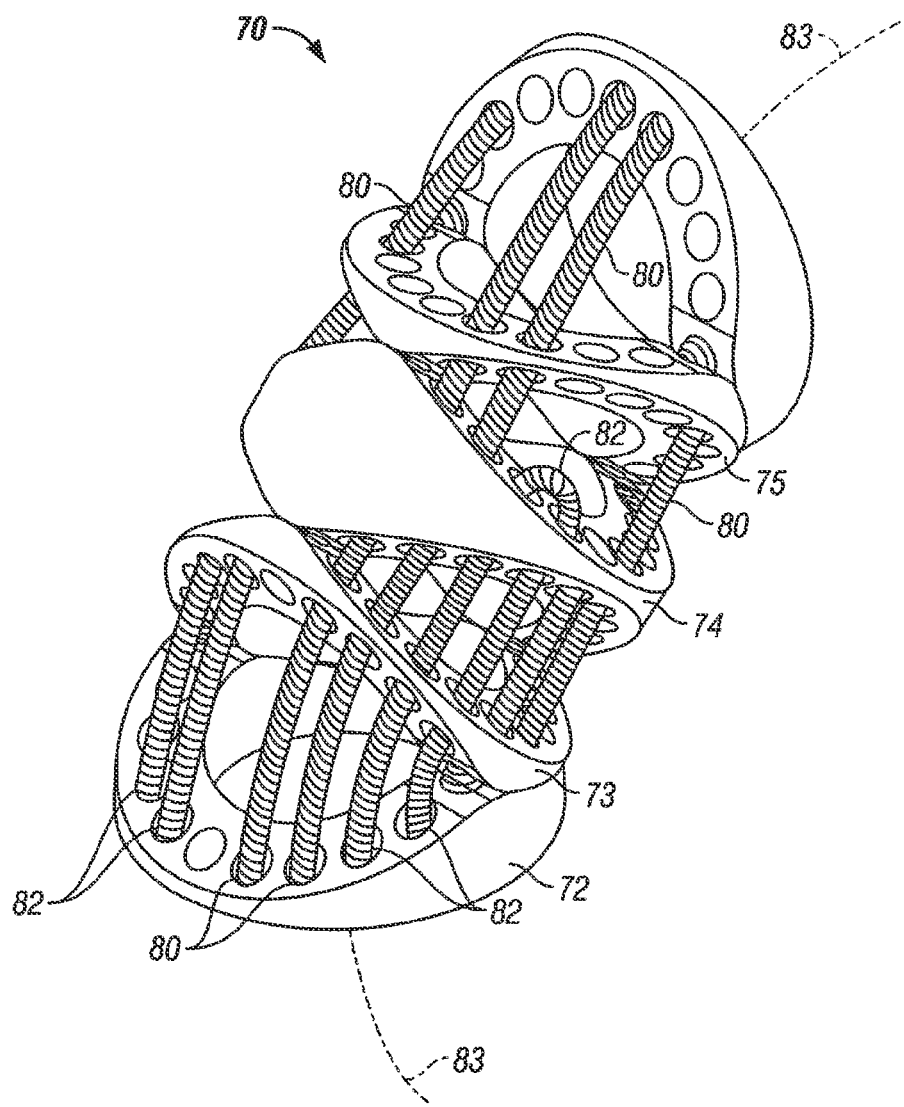
FIG. 5 is a perspective view of a positively positionable multi-disk (PPMD) wrist in pitch rotation according to an embodiment of the present invention.
Figure 6:
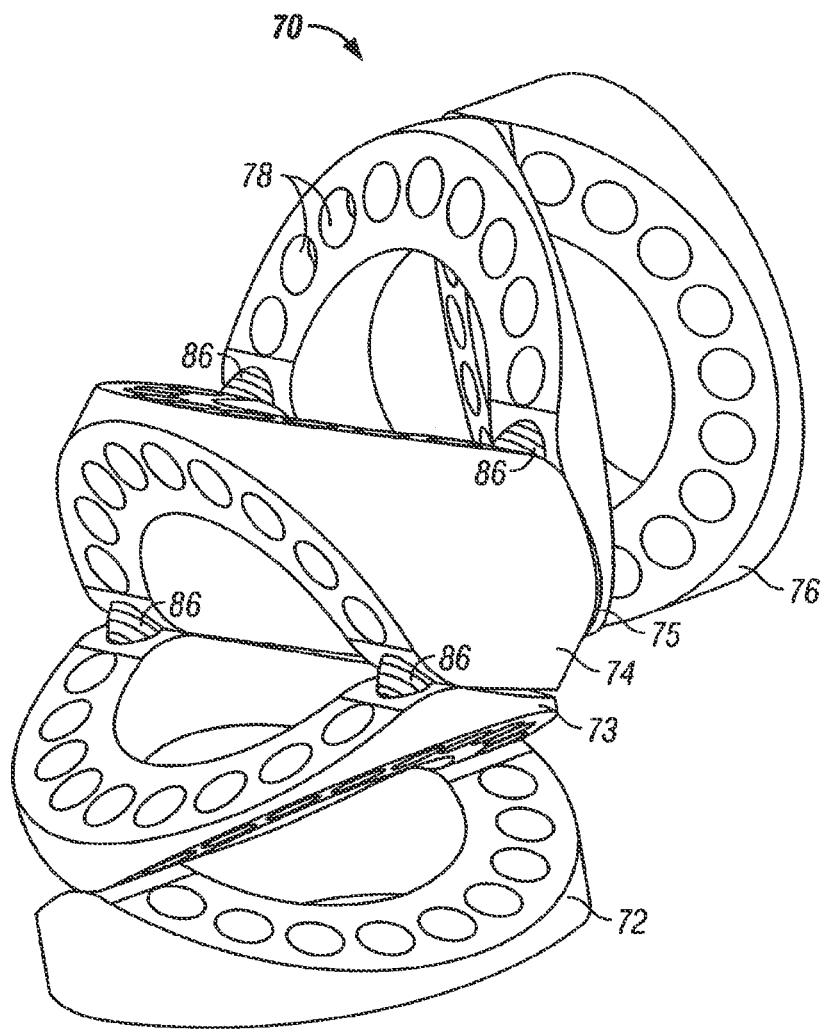
FIG. 6 is a perspective view of the PPMD wrist of FIG. 5 in yaw rotation.
Figure 7:
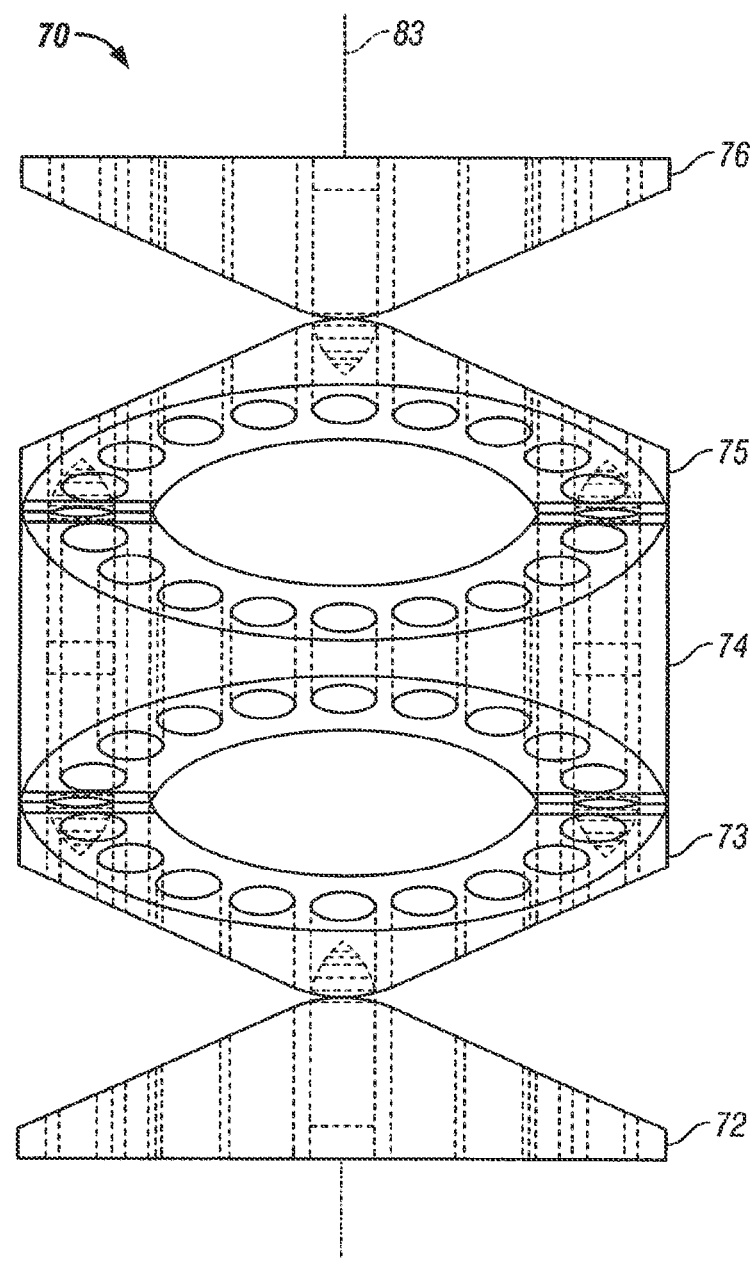
FIG. 7 is an elevational view of the PPMD wrist of FIG. 5 in a straight position.
Figure 8:
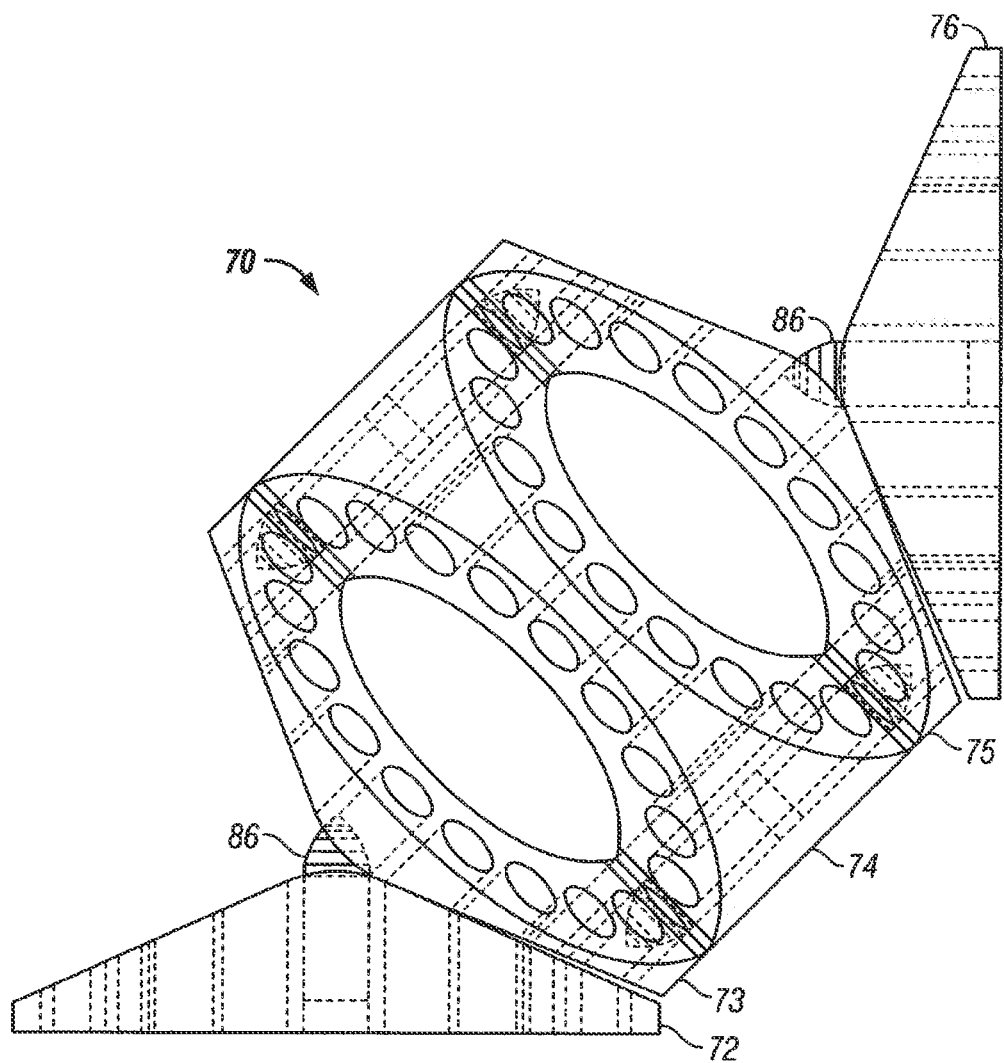
FIG. 8 is an elevational view of the PPMD wrist of FIG. 5 in pitch rotation.

FIG. 5 shows alternating pairs of long or distal cables 80 and short or medial cable 82 disposed around the disks. The cables 80, 82 extending through the disks are parallel to a wrist central axis or neutral axis 83 extending through the centers of the disks. The wrist neutral axis 83 is fixed in length during bending of the wrist 70. When the disks are aligned in a straight line, the cables 80, 82 are straight; when the disks are rotated during bending of the wrist 70, the cables 80, 82 bend with the wrist neutral axis. In the examples shown in FIGS. 5-8, the disks are configured to roll on each other in nonattached, rolling contact to maintain the contact points between adjacent disks in the center, as formed by pairs of pins 86 coupled to apertures 78 disposed on opposite sides of the disks. The pins 86 are configured and sized such that they provide the full range of rotation between the disks and stay coupled to the apertures 78. The apertures 78 may be replaced by slots for receiving the pins 86 in other embodiments. Note that the contour of pins 86 is preferably of a "gear tooth-like" profile, so as to make constant smooth contact with the perimeter 87 of its engaged aperture during disk rotation, so as to provide a smooth non-slip rolling engagement. FIGS. 5 and 8 show the wrist 70 in a 90° pitch position (by rotation of the two pitch joints), while FIG. 6 shows the wrist 70 in a 90° yaw position (by rotation of the two yaw joints). In FIG. 7, the wrist 70 is in an upright or straight position. Of course, combined pitch and yaw bending of the wrist member can be achieved by rotation of the disks both in pitch and in yaw.

The wrist 70 is singularity free over a 180° range. The lumen formed by the annular disks can be used for isolation and for passing pull cables for grip. The force applied to the wrist 70 is limited by the strength of the cables. In one embodiment, a cable tension of about 15 lb. is needed for a yaw moment of about 0.25 N-m. Because there are only five disks, the grip mechanism needs to be able to bend sharply. Precision of the cable system depends on the friction of the cables rubbing on the apertures 78. The cables 80, 82 can be preloaded to remove backlash. Because wear is a concern, wear-resistant materials should desirably be selected for the wrist 70 and cables.

Figure 9:
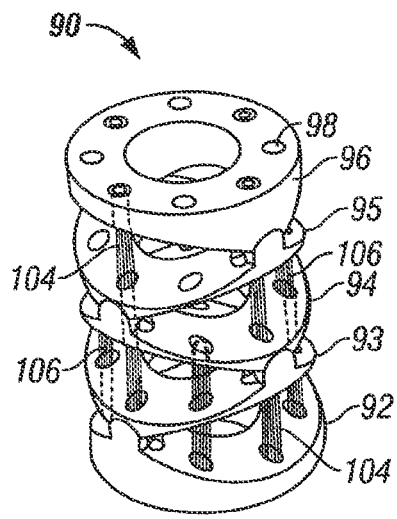
FIG. 9 is a perspective view of a PPMD wrist in a straight position according to another embodiment of the present invention.
Figure 10:
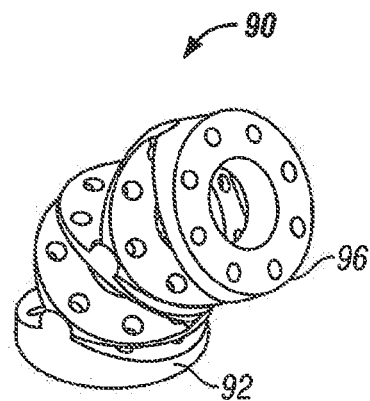
FIG. 10 is a perspective view of the PPMD wrist of FIG. 9 in pitch rotation.
Figure 11:
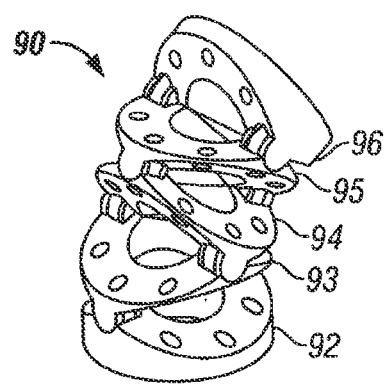
FIG. 11 is a perspective view of the PPMD wrist of FIG. 9 in yaw rotation.
Figure 12:
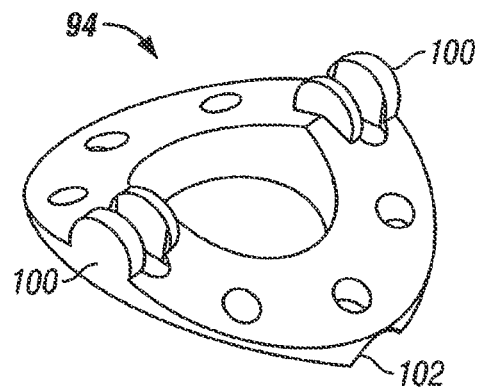
FIG. 12 is an upper perspective of an intermediate disk in the PPMD wrist of FIG. 9.
Figure 13:
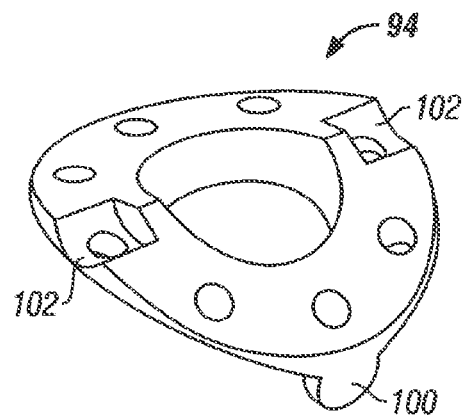
FIG. 13 is a lower perspective of the intermediate disk of FIG. 12.

FIGS. 9-13 show an alternative embodiment of a wrist 90 having a different coupling mechanism between the disks 92-96 which include apertures 98 for passing through actuation cables. Instead of pins coupled with apertures, the disks are connected by a coupling between pairs of curved protrusions 100 and slots 102 disposed on opposite sides of the disks, as best seen in the disk 94 of FIGS. 12-13. The other two intermediate disks 93, 95 are similar to the middle disk 94. The curved protrusions 100 are received by the curved slots 102 which support the protrusions 100 for rotational or rolling movement relative to the slots 102 to generate, for instance, the 90° pitch of the wrist 90 as shown in FIG. 10 and the 90° yaw of the wrist 90 as shown in FIG. 11. FIG. 9 shows two distal cables 104 extending to and terminating at the distal disk 96, and two medial cables 106 extending to and terminating at the middle disk 94. Note that the example shown in FIGS. 9-13 is not a "constant velocity" YPPY arrangement, but may alternatively be so configured.

Figure 14:
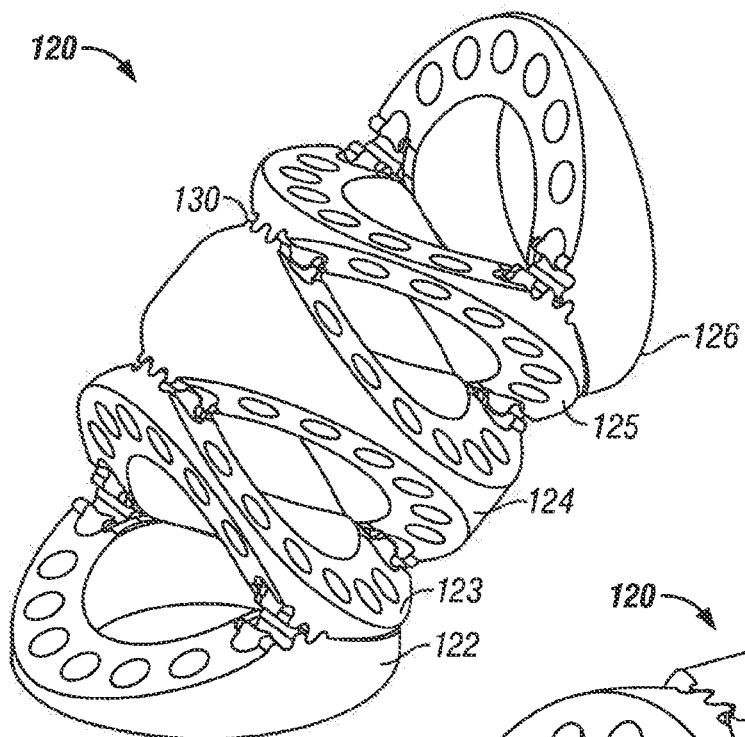
FIG. 14 is a perspective view of a PPMD wrist in pitch rotation in accordance with another embodiment of the present invention.
Figure 15:
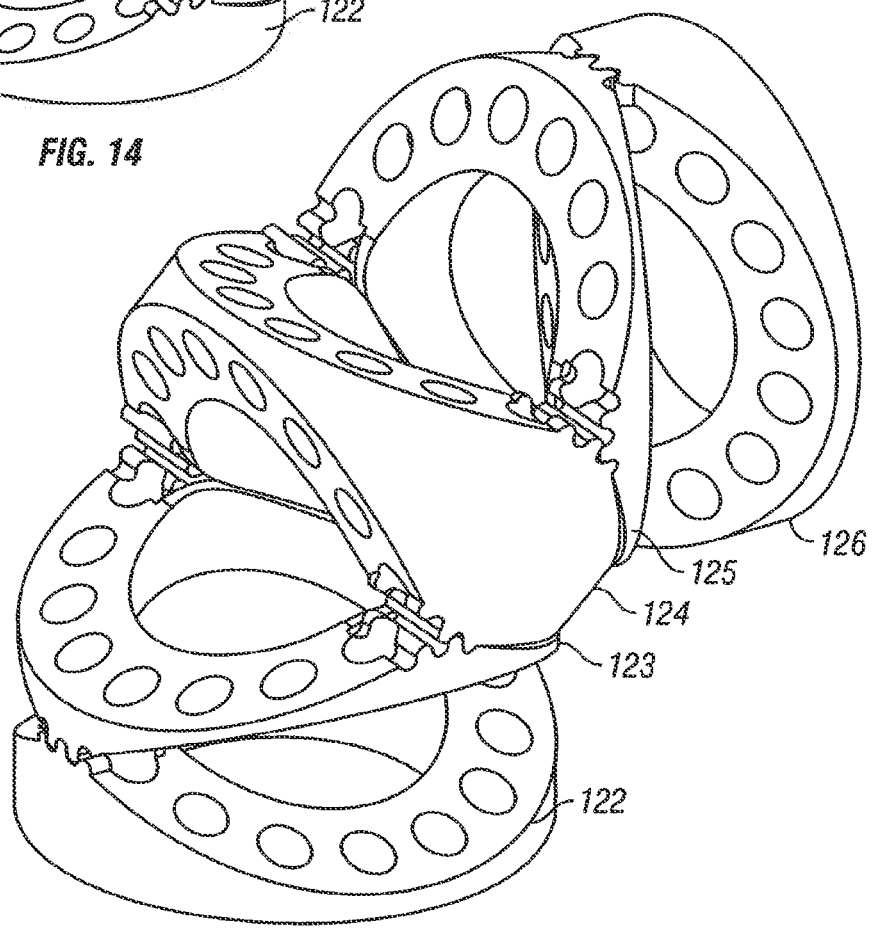
FIG. 15 is a perspective view of the PPMD wrist of FIG. 14 in yaw rotation.

In another embodiment of the wrist 120 as shown in FIGS. 14 and 15, the coupling between the disks 122-126 is formed by nonattached, rolling contact between matching gear teeth 130 disposed on opposite sides of the disks. The gear teeth 130 guide the disks in yaw and pitch rotations to produce, for instance, the 90° pitch of the wrist 120 as shown in FIG. 14 and the 90° yaw of the wrist 120 as shown in FIG. 15.

Figure 16:
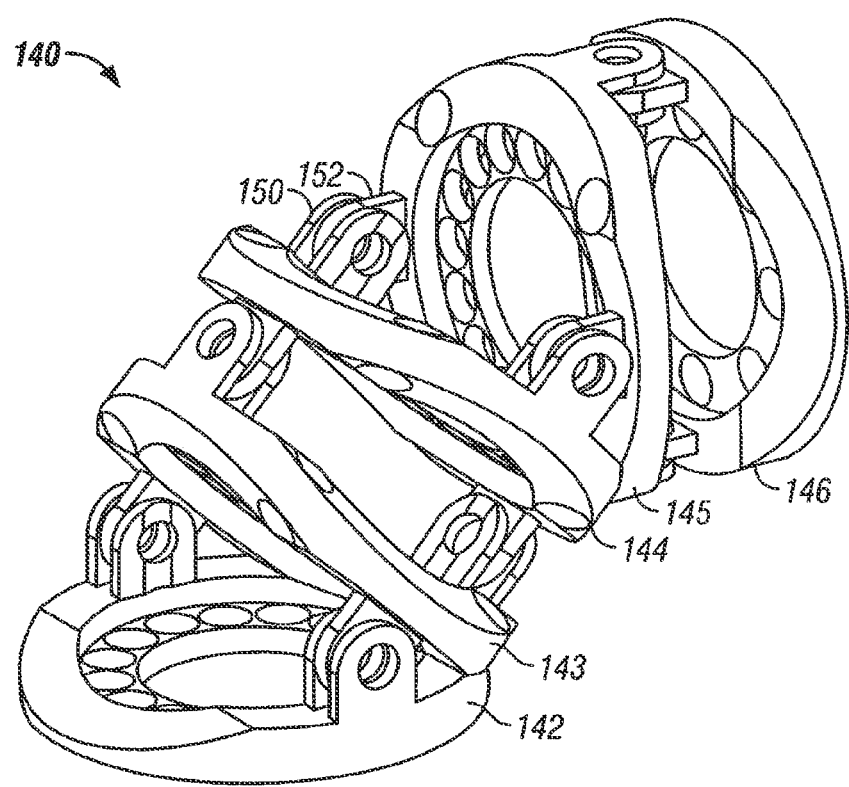
FIG. 16 is a perspective view of a PPMD wrist in pitch rotation according to another embodiment of the present invention.
Figure 17:
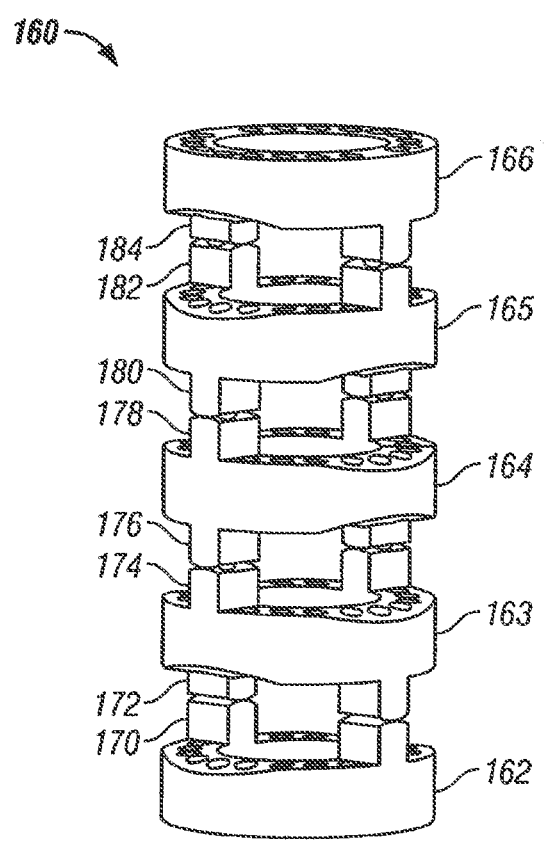
FIG. 17 is a perspective view of a PPMD wrist in a straight position in accordance with another embodiment of the present invention.

In another embodiment of the wrist 140 as illustrated in FIG. 16, the coupling mechanism between the disks includes apertured members 150, 152 cooperating with one another to permit insertion of a fastener through the apertures to form a hinge mechanism. The hinge mechanisms disposed on opposite sides of the disks guide the disks in pitch and yaw rotations to produce, for instance, the 90° pitch of the wrist 140 as seen in FIG. 16. Note that the example shown in FIG. 16 is not a "constant velocity" YPPY arrangement, but may alternatively be so configured.

FIGS. 17-24 show yet another embodiment of the wrist 160 having a different coupling mechanism between the disks 162-166. The first or proximal disk 162 includes a pair of pitch protrusions 170 disposed on opposite sides about 180° apart. The second disk 163 includes a pair of matching pitch protrusions 172 coupled with the pair of pitch protrusions 170 on one side, and on the other side a pair of yaw protrusions 174 disposed about 90° offset from the pitch protrusions 172. The third or middle disk 164 includes a pair of matching yaw protrusions 176 coupled with the pair of yaw protrusions 174 on one side, and on the other side a pair of yaw protrusions 178 aligned with the pair of yaw protrusions 174. The fourth disk 165 includes a pair of matching yaw protrusions 180 coupled with the pair of yaw protrusions 178 on one side, and on the other side a pair of pitch protrusions 182 disposed about 90° offset from the yaw protrusions 180. The fifth or distal disk 166 includes a pair of matching pitch protrusions 184 coupled with the pitch protrusions 182 of the fourth disk 165.

Figure 18:
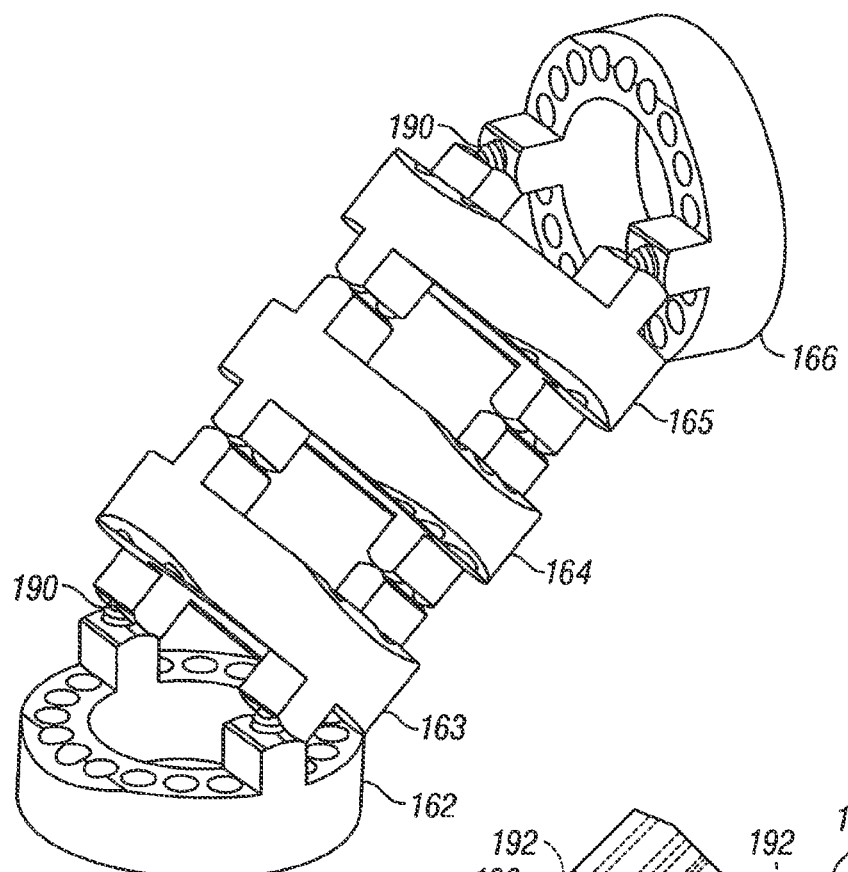
FIG. 18 is a perspective view of the PPMD wrist of FIG. 17 in pitch rotation.
Figure 19:
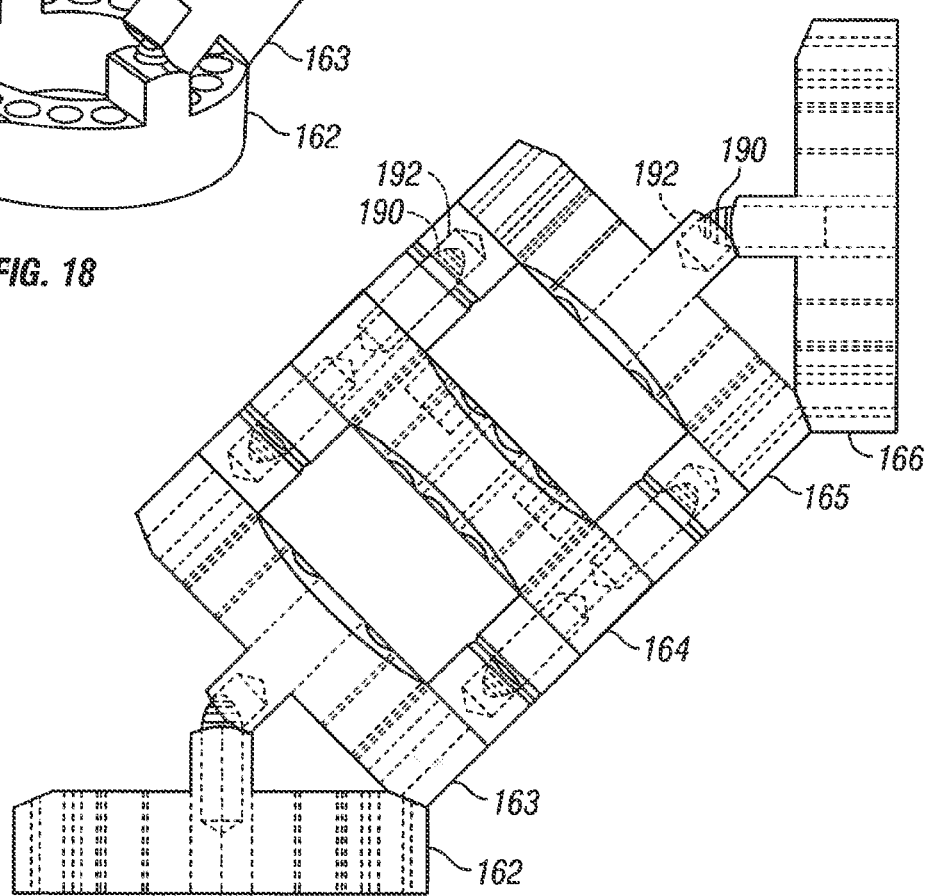
FIG. 19 is an elevational view of the PPMD wrist of FIG. 17 in pitch rotation.
Figure 20:
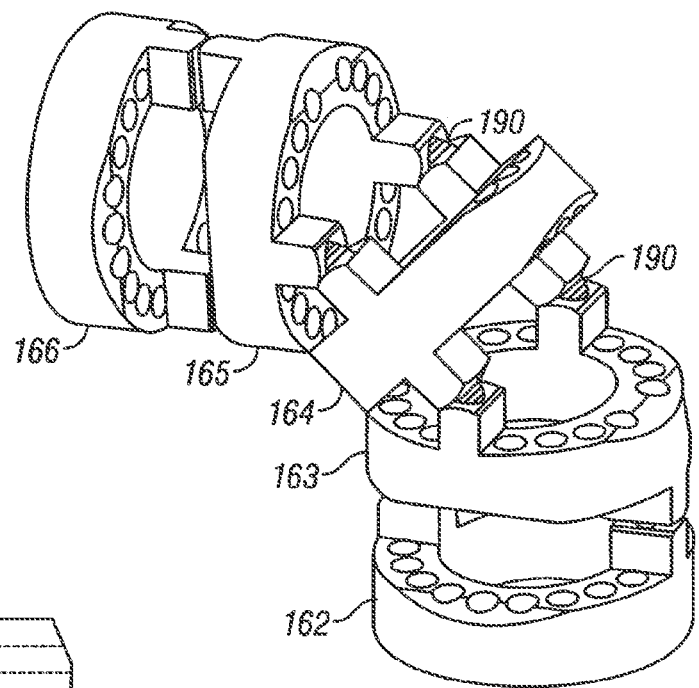
FIG. 20 is a perspective view of the PPMD wrist of FIG. 17 in yaw rotation.
Figure 21:
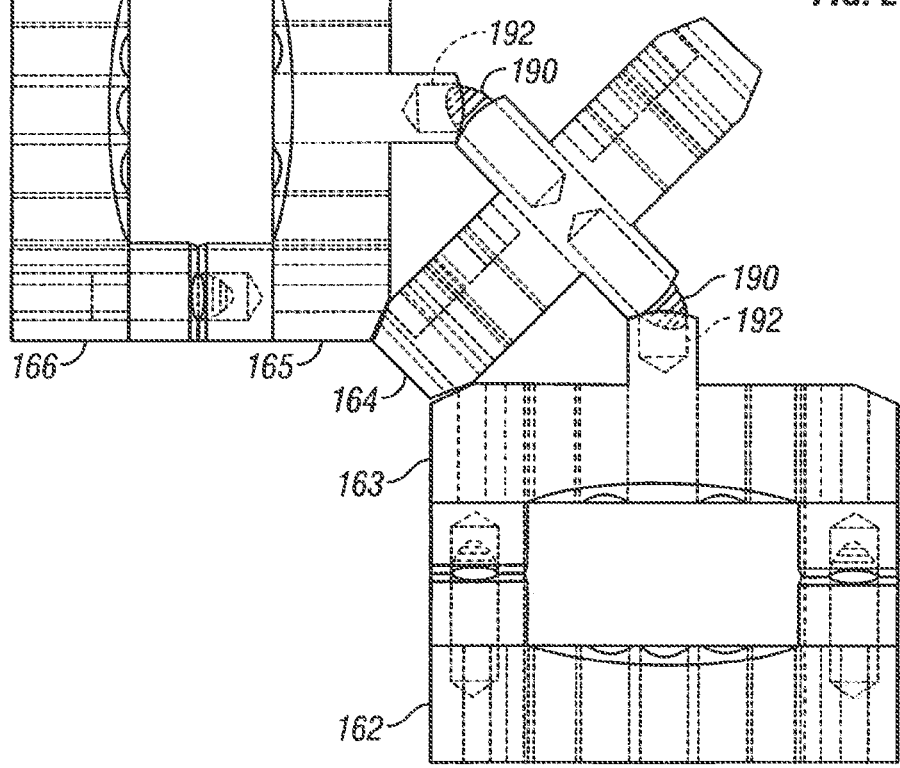
FIG. 21 is an elevational view of the PPMD wrist of FIG. 17 in yaw rotation.

The protrusions 172 and 176 having curved, convex rolling surfaces that make nonattached, rolling contact with each other to guide the disks in pitch or yaw rotations to produce, for instance, the 90° pitch of the wrist 160 as seen in FIGS. 18 and 19 and the 90° yaw of the wrist 160 as seen in FIGS. 20 and 21. In the embodiment shown, the coupling between the protrusions is each formed by a pin 190 connected to a slot 192.

Figure 22:
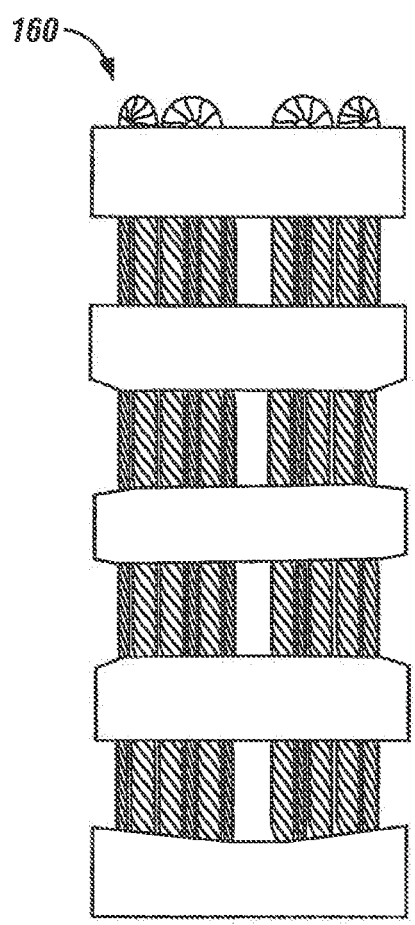
FIG. 22 is an elevational view of the PPMD wrist of FIG. 17 showing the actuation cables extending through the disks according to an embodiment of the invention.
Figure 23:
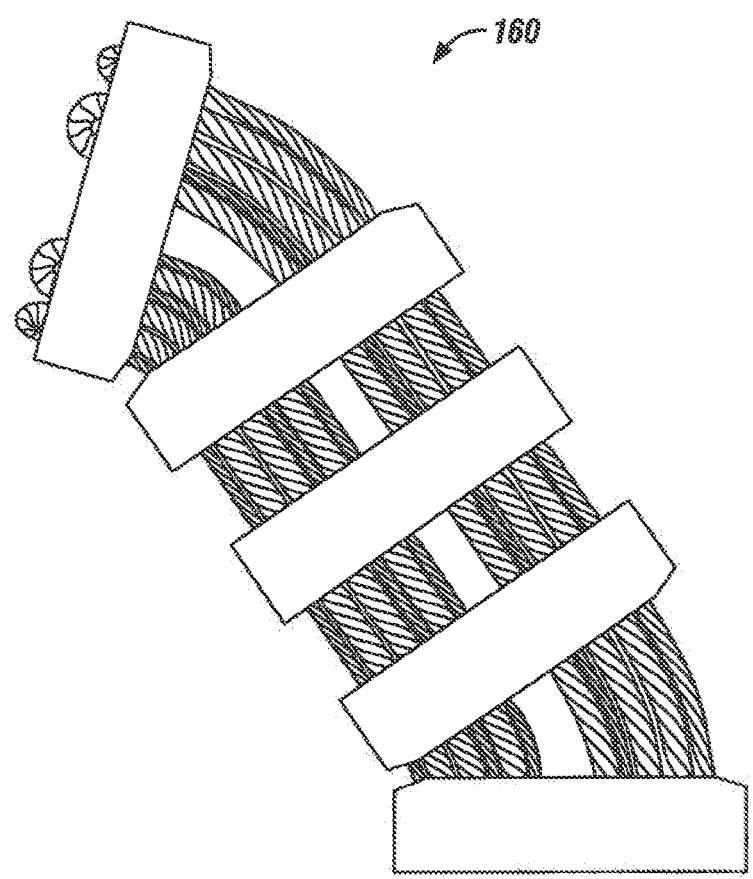
FIG. 23 is an elevational view of the PPMD wrist of FIG. 17 in pitch rotation.
Figure 24:
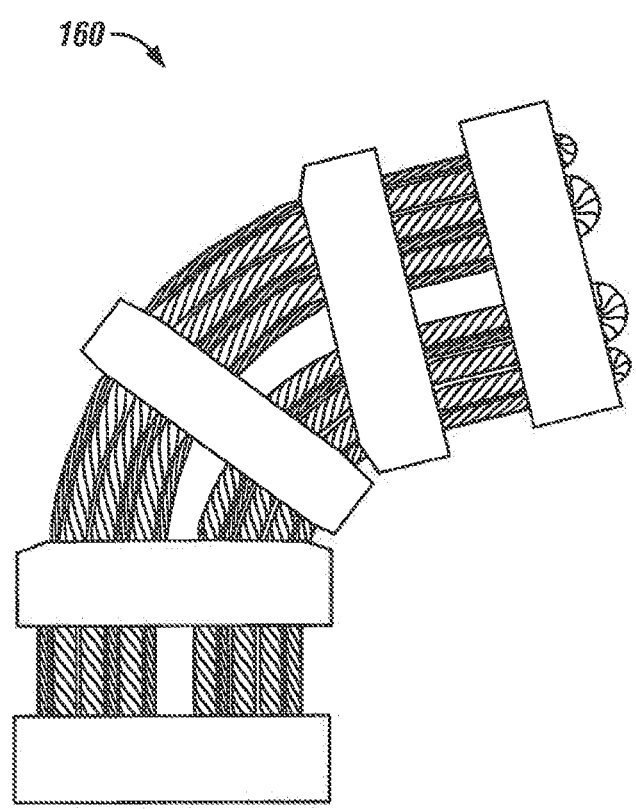
FIG. 24 is an elevational view of the PPMD wrist of FIG. 17 in yaw rotation.

FIGS. 22-24 illustrate the wrist 160 manipulated by actuation cables to achieve a straight position, a 90° pitch position, and a 90° yaw position, respectively.

Figure 25:
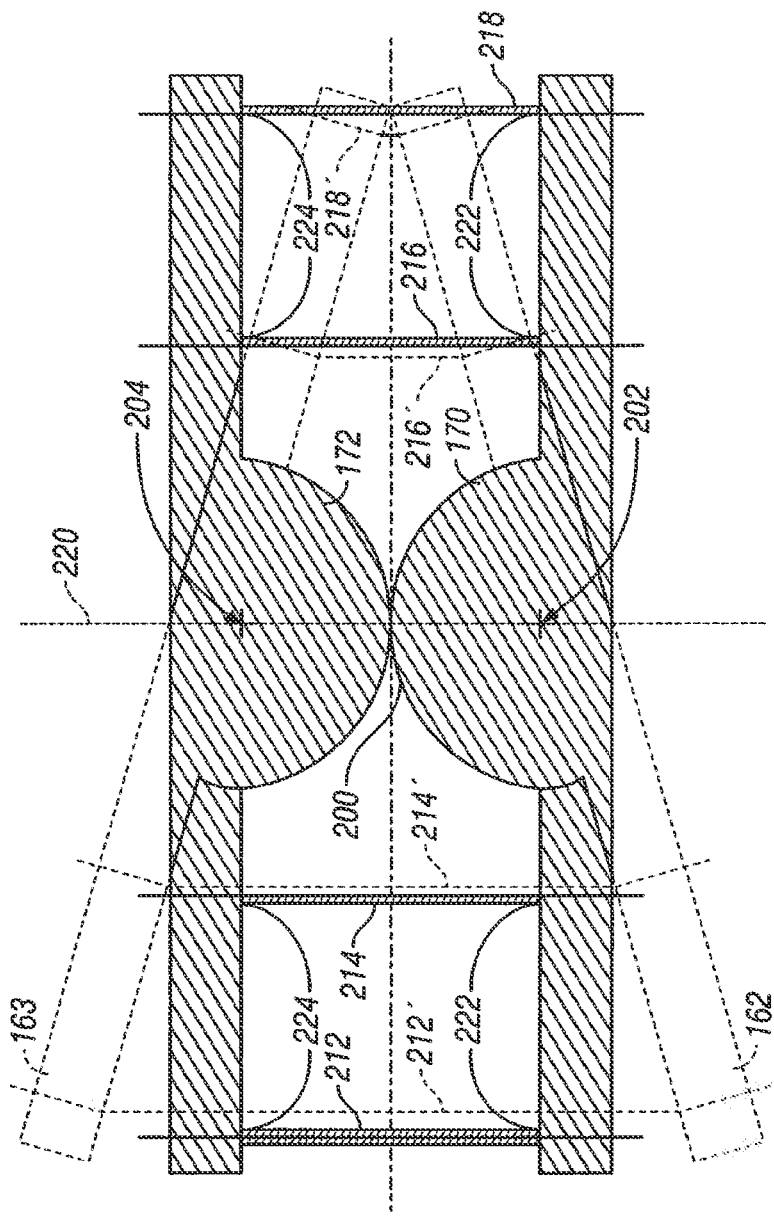
FIG. 25 is an cross-sectional view of the coupling between the disks of the PPMD wrist of FIG. 17 illustrating the rolling contact therebetween.

FIG. 25 illustrates the rolling contact between the curved rolling surfaces of protrusions 170, 172 for disks 162, 163, which maintain contact at a rolling contact point 200. The rolling action implies two virtual pivot points 202, 204 on the two disks 162, 163, respectively. The relative rotation between the disks 162, 163 is achieved by pulling cables 212, 214, 216, 218. Each pair of cables (212, 218) and (214, 216) are equidistant from the center line 220 that passes through the contact point 200 and the virtual pivot points 202, 204. Upon rotation of the disks 162, 163, the pulling cables shift to positions 212', 214', 216', 218', as shown in broken lines. The disk 162 has cable exit points 222 for the cables, and the disk 163 has cable exit points 224 for the cables. In a specific embodiment, the cable exit points 222 are coplanar with the virtual pivot point 202 of the disk 162, and the cable exit points 224 are coplanar with the virtual pivot point 204 of the disk 164. In this way, upon rotation of the disks 162, 163, each pair of cables (212', 218') and (214', 216') are kept equidistant from the center line 220. As a result, the cable length paid out on one side is equal to the cable length pulled on the other side. Thus, the non-attached, rolling engagement contour arrangement shown in FIG. 25 may be referred to as a "cable balancing pivotal mechanism." This "cable balancing" property facilitates coupling of pairs of cables with minimal backlash. Note that the example of FIGS. 17-24 has this "cable balancing" property, although due to the size of these figures, the engagement rolling contours are shown at a small scale.

Optionally, and particularly in embodiments not employing a "cable balancing pivotal mechanism" to couple adjacent disks, the instrument cable actuator(s) may employ a cable tension regulation device to take up cable slack or backlash.

The above embodiments show five disks, but the number of disks may be increased to seven, nine, etc. For a seven-disk wrist, the range of rotation increases from 180° to 270°. Thus, in a seven-disk wrist, typically ⅓ of the cables terminate at disk 3; ⅓ terminate at disk 5; and ⅓ terminate at disk 7 (most distal).

C. Pivoted Plate Cable Actuator Mechanism

Figure 26:
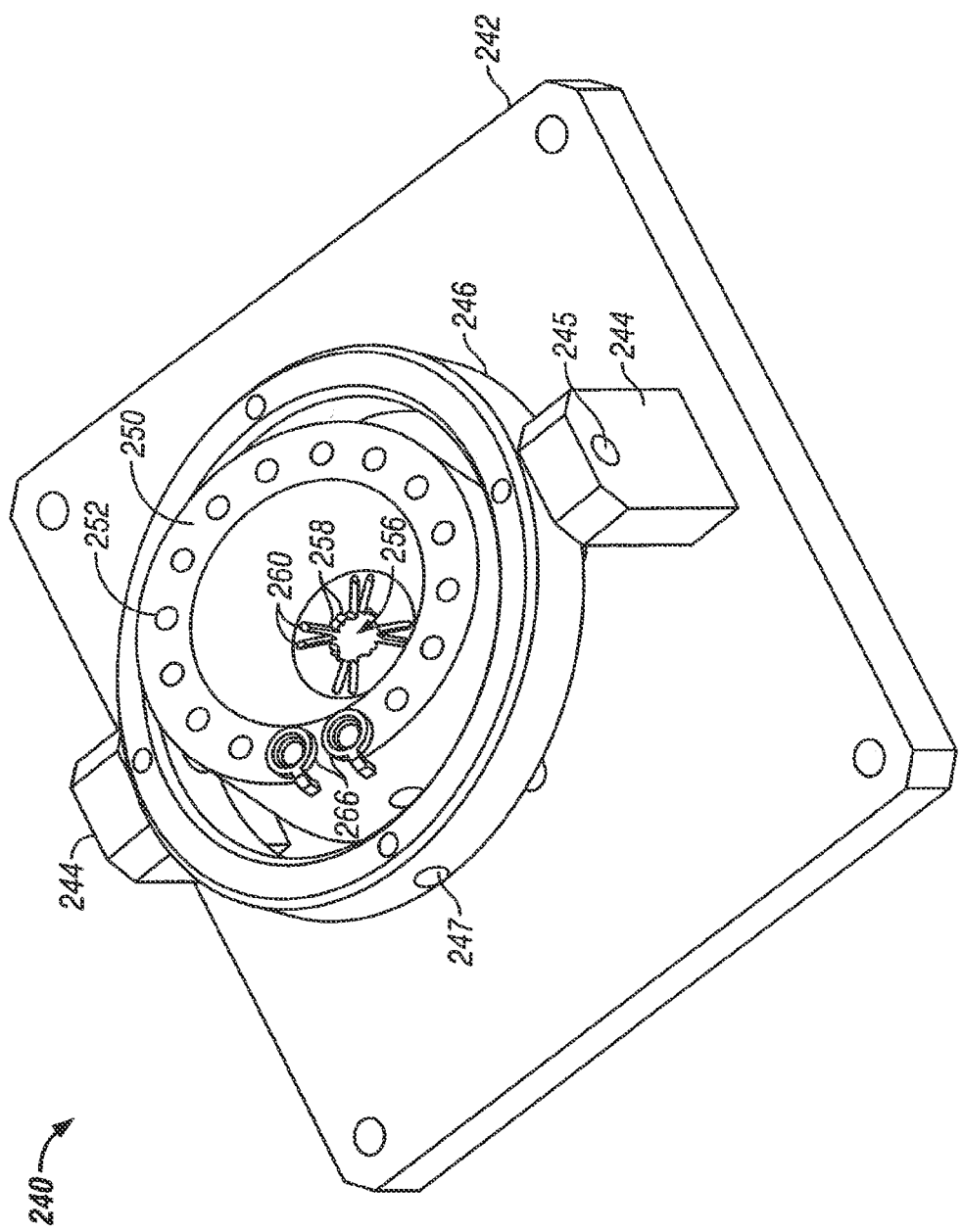
FIG. 26 is a perspective view of a gimbaled cable actuator according to an embodiment of the invention.

FIG. 26 shows an exemplary pivoted plate cable actuator mechanism 240 having aspects of the invention, for manipulating the cables, for instance, in the PPMD wrist 160 shown in FIGS. 17-21. The actuator 240 includes a base 242 having a pair of gimbal ring supports 244 with pivots 245 for supporting a gimbal ring 246 for rotation, for example, in pitch. The ring 246 includes pivots 247 for supporting a rocker or actuator plate 250 in rotation, for example, in yaw. The actuator plate 250 includes sixteen holes 252 for passing through sixteen cables for manipulating the wrist 160 (from the proximal disk 162, eight distal cables extend to the distal disk 166 and eight medial cables extend to the middle disk 164).

The actuator plate 250 includes a central aperture 256 having a plurality of grooves for receiving the cables. There are eight small radius grooves 258 and eight large radius grooves 260 distributed in pairs around the central aperture 256. The small radius grooves 258 receive medial cables that extend to the middle disk 164, while the large radius grooves 260 receive distal cables that extend to the distal disk 166. The large radius for grooves 260 is equal to about twice the small radius for grooves 258. The cables are led to the rim of the central aperture 256 through the grooves 258, 260 which restrain half of the cables to a small radius of motion and half of the cables to a large radius of motion, so that the medial cables to the medial disk 164 move only half as far as the distal cables to the distal disk 166, for a given gimbal motion. The dual radius groove arrangement facilitates such motion and control of the cables when the actuator plate 250 is rotated in the gimbaled cable actuator 240. A pair of set screws 266 are desirably provided to fix the cable attachment after pre-tensioning. The gimbaled cable actuator 240 acts as a master for manipulating and controlling movement of the slave PPMD wrist 160. Various kinds of conventional actuator (not shown in FIG. 26) may be coupled to actuator plate assembly to controllably tilt the plate in two degrees of freedom to actuate to cables.

Figure 27:
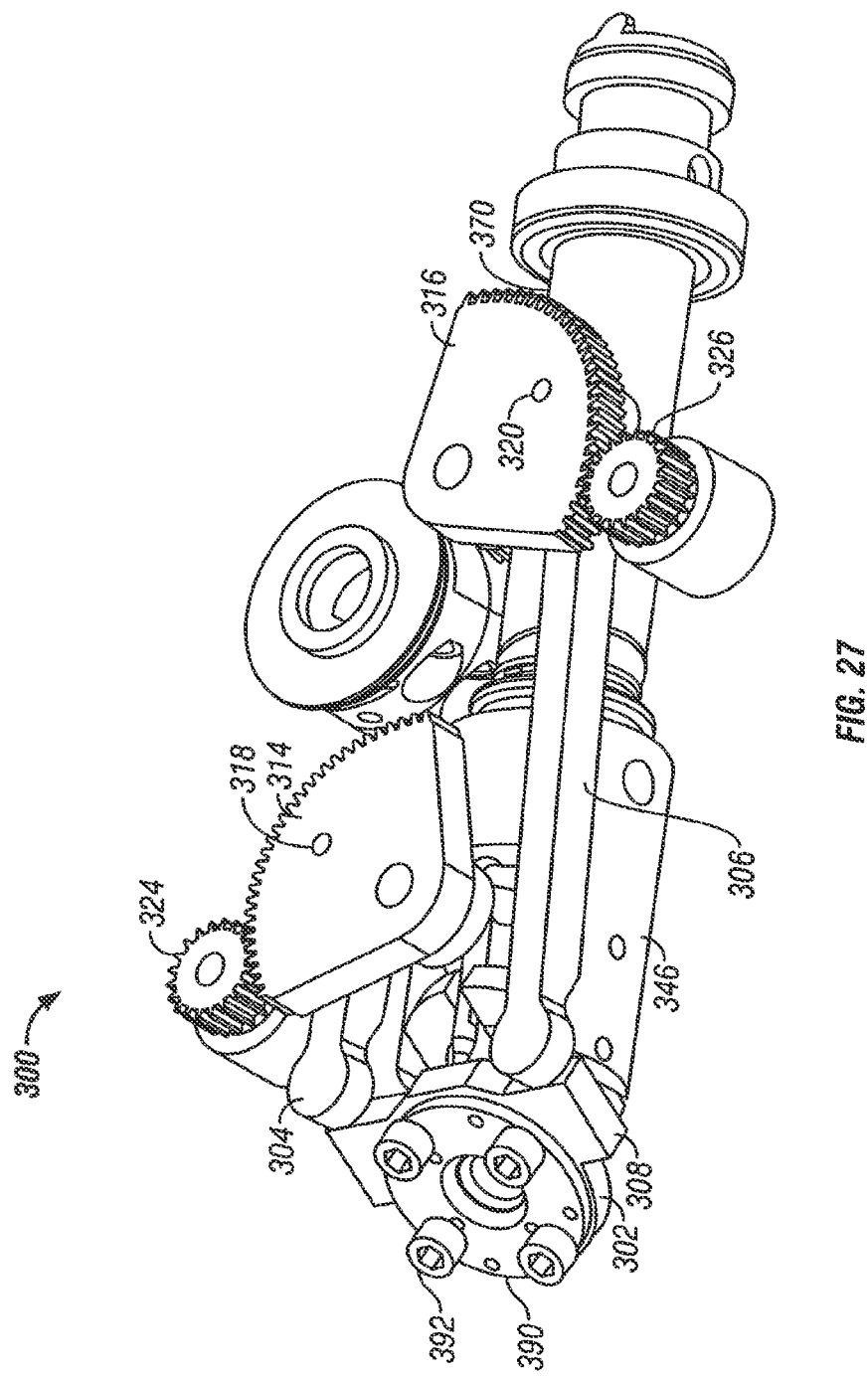
FIG. 27 is a perspective view of a gimbaled cable actuator with the actuator links configured in pitch rotation according to another embodiment of the present invention.
Figure 28:
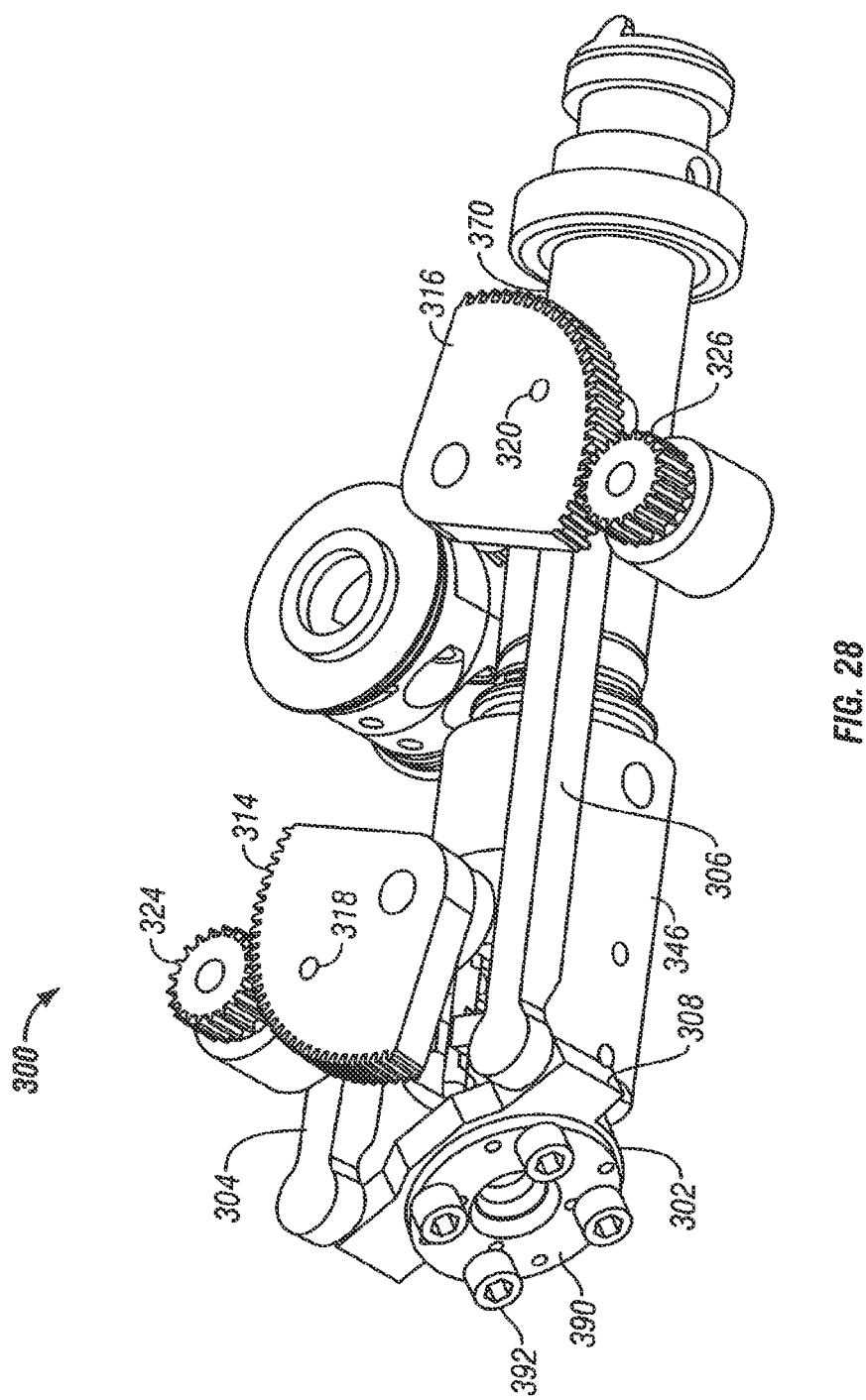
FIG. 28 is a perspective view of the gimbaled cable actuator of FIG. 27 with the actuator links configured in yaw rotation.
Figure 32:
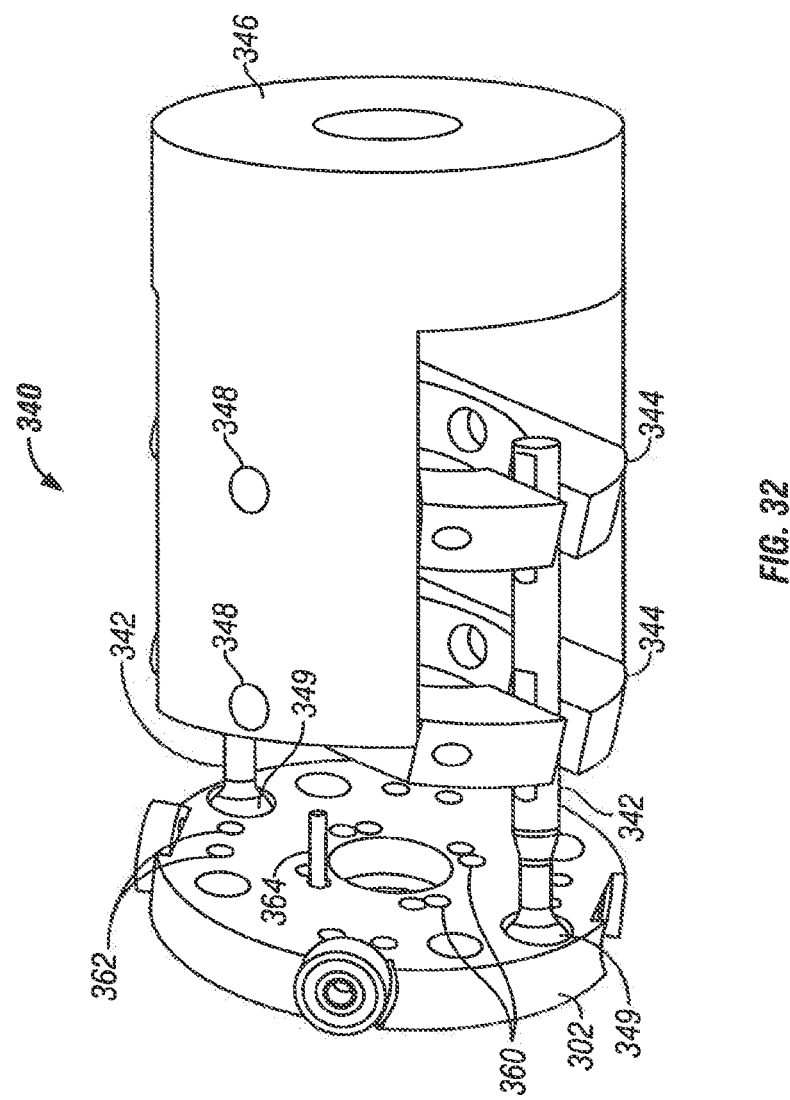
FIG. 32 is another perspective view of the parallel linkage of FIG. 30 illustrating details of the actuator plate.
Figure 33:
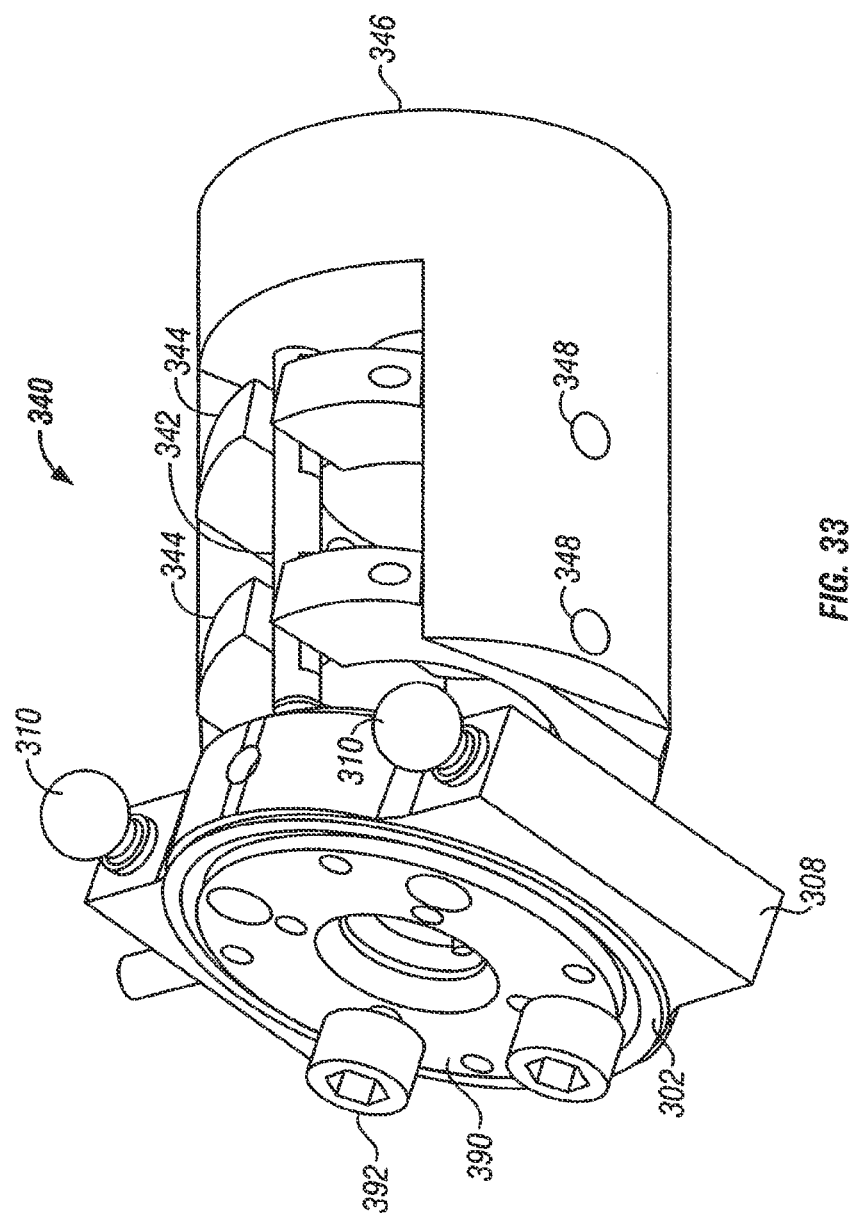
FIG. 33 is a perspective view of the parallel linkage of FIG. 30 illustrating the cover plate over the actuator plate and a mounting member around the actuator plate for mounting the actuator links.
Figure 34:
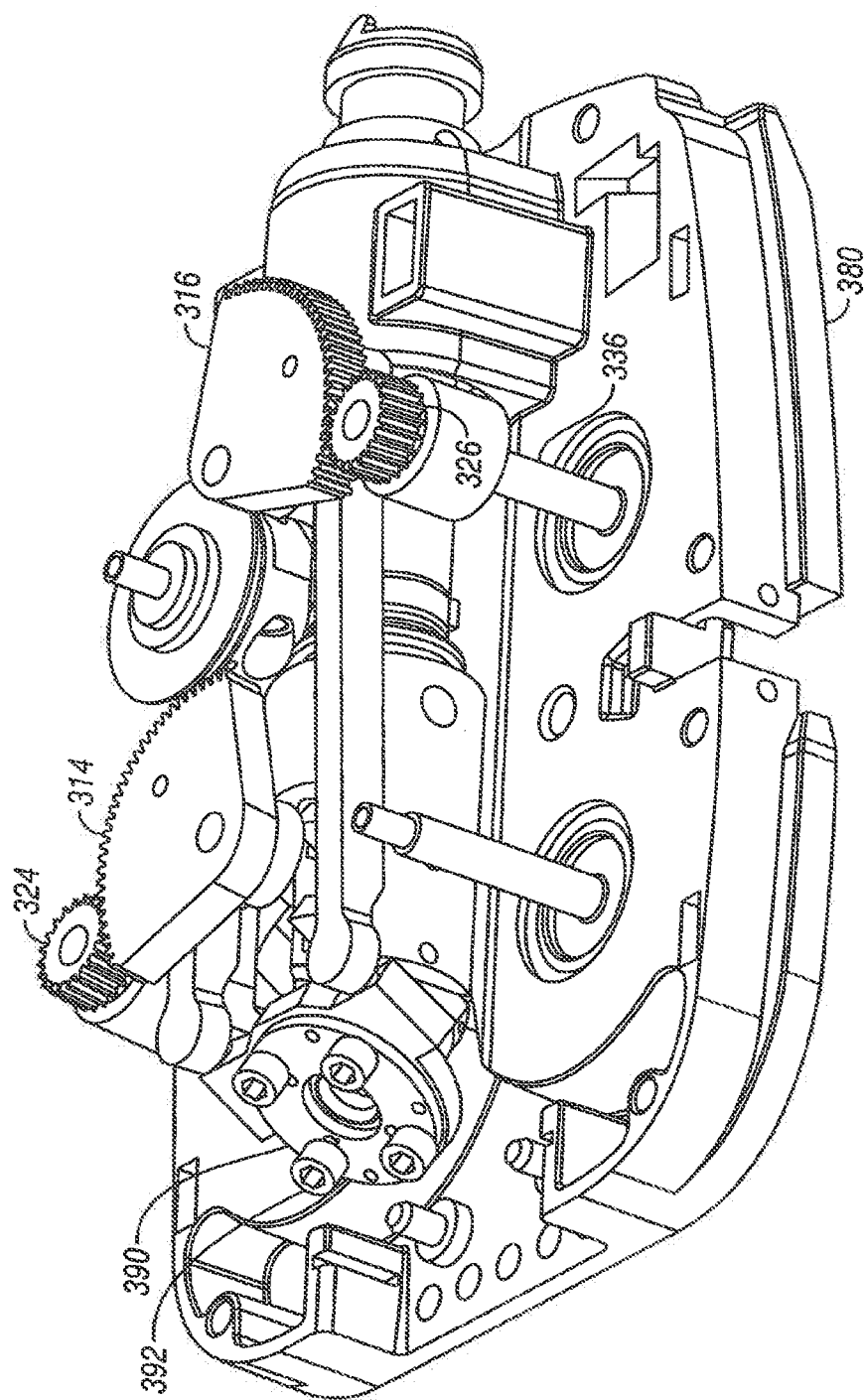
FIG. 34 is a perspective view of the gimbaled cable actuator of FIG. 27 mounted on a lower housing member.
Figure 35:
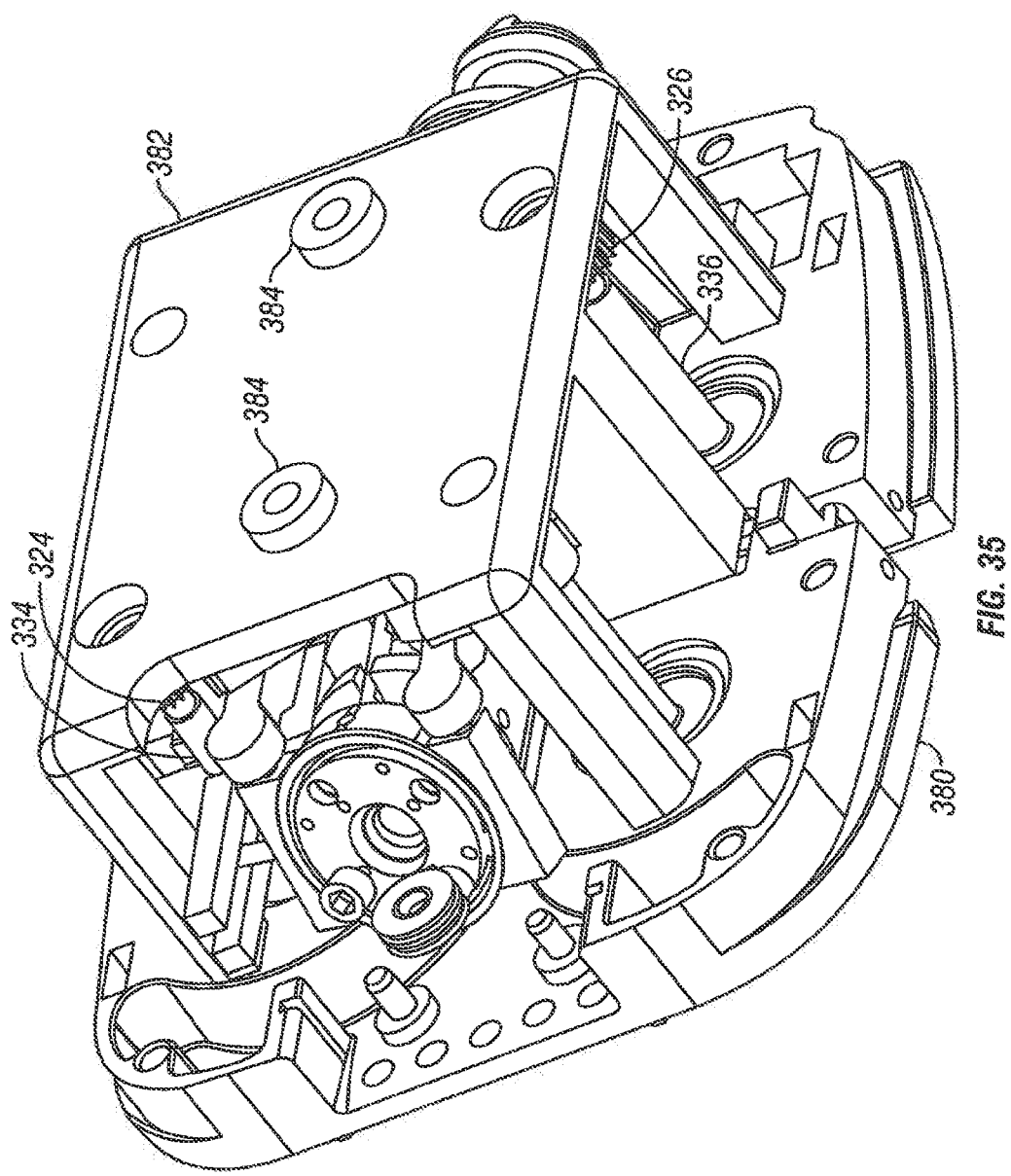
FIG. 35 is a perspective view of the gimbaled cable actuator of FIG. 27 mounted between a lower housing member and an upper housing member.

FIGS. 27-35 illustrate another embodiment of a gimbaled cable actuator 300 for manipulating the cables to control movement of the PPMD wrist, in which an articulated parallel strut/ball joint assembly is employed to provide a "gimbaled" support for actuator plate 302 (i.e., the plate is supported so as to permit plate tilting in two DOF). The actuator 300 includes a rocker or actuator plate 302 mounted in a gimbal configuration. The actuator plate 302 is moved by a first actuator link 304 and a second actuator link 306 to produce pitch and yaw rotations. The actuator links 304, 306 are rotatably coupled to a mounting member 308 disposed around the actuator plate 302. As best seen in FIG. 33, ball ends 310 are used for coupling the actuator links 304, 306 with the mounting member 308 to form ball-in-socket joints in the specific embodiment shown, but other suitable rotational connections may be used in alternate embodiments. The actuator links 304, 306 are driven to move generally longitudinally by first and second follower gear quadrants 314, 316, respectively, which are rotatably coupled with the actuator links 304, 306 via pivot joints 318, 320, as shown in FIGS. 27 and 28. The gear quadrants 314, 316 are rotated by first and second drive gears 324, 326, respectively, which are in turn actuated by drive spools 334, 336, as best seen in FIGS. 34 and 35.

The actuator plate 302 is coupled to a parallel linkage 340 as illustrated in FIGS. 30-33. The parallel linkage 340 includes a pair of parallel links 342 coupled to a pair of parallel rings 344 which form a parallelogram in a plane during movement of the parallel linkage 340. The pair of parallel links 342 are rotatably connected to the pair of parallel rings 344, which are in turn rotatably connected to a parallel linkage housing 346 via pivots 348 to rotate in pitch. The pair of parallel links 342 may be coupled to the actuator plate 302 via ball-in-socket joints 349, as best seen in FIG. 32, although other suitable coupling mechanisms may be used in alternate embodiments.

Figure 29:
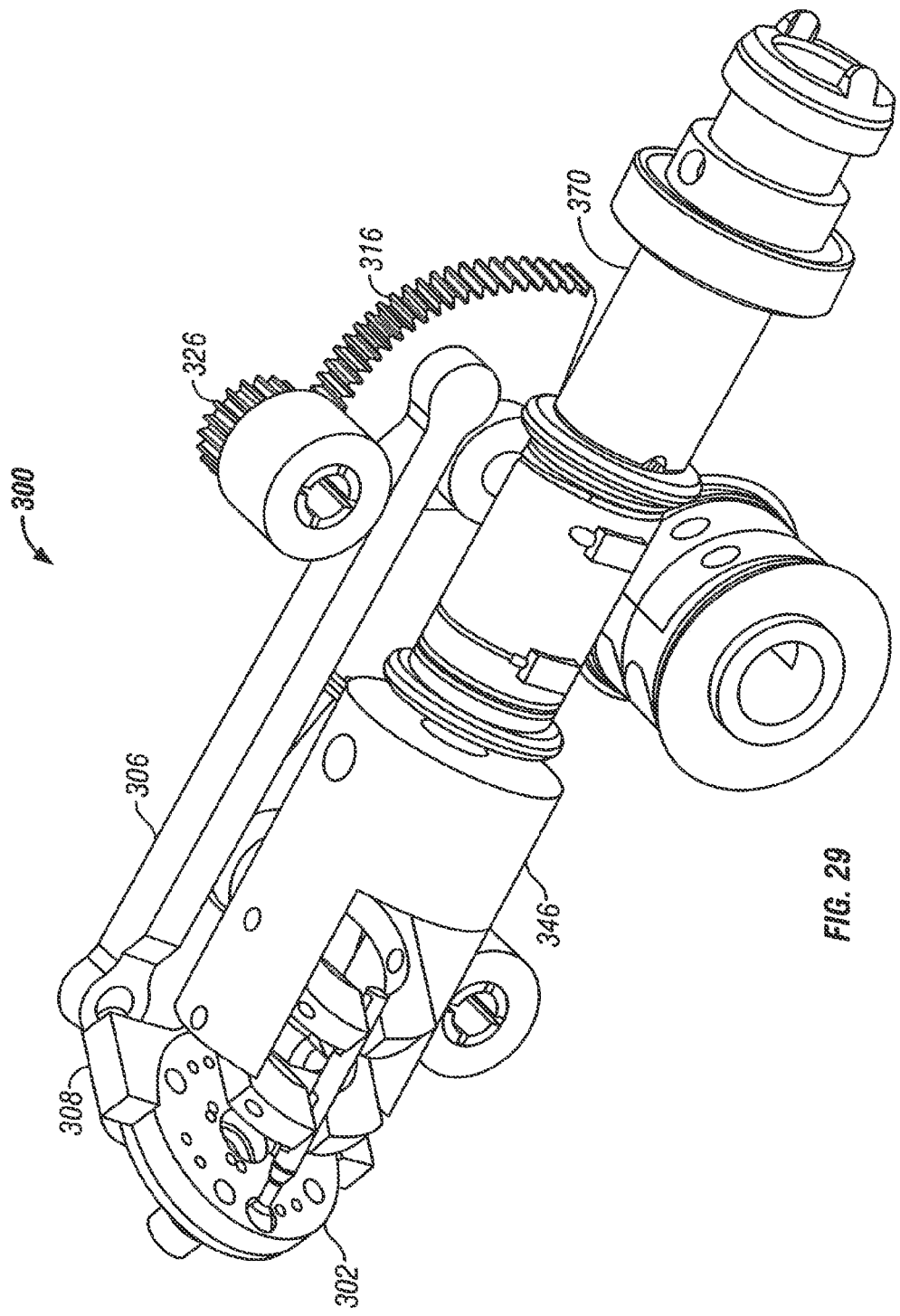
FIG. 29 is another perspective view of the gimbaled cable actuator of FIG. 27 in pitch rotation.

FIGS. 27 and 29 show the actuator plate 302 of the gimbaled cable actuator 300 in pitch rotation with both actuator links 304, 306 moving together so that the actuator plate 302 is constrained by the parallel linkage 340 to move in pitch rotation. In FIG. 28, the first and second actuator links 304, 306 move in opposite directions to produce a yaw rotation of the actuator plate 302. Mixed pitch and yaw rotations result from adjusting the mixed movement of the actuator links 304, 306.

Figure 30:
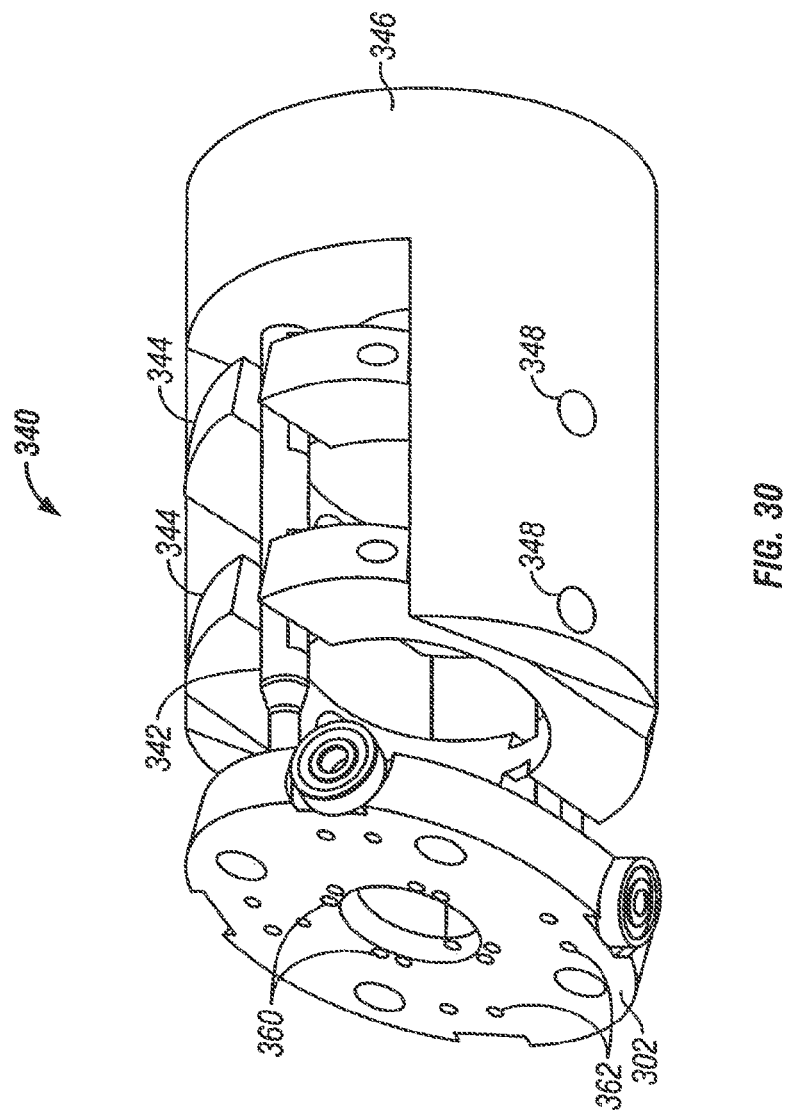
FIG. 30 is a perspective view of the parallel linkage in the gimbaled cable actuator of FIG. 27 illustrating details of the actuator plate.
Figure 31:
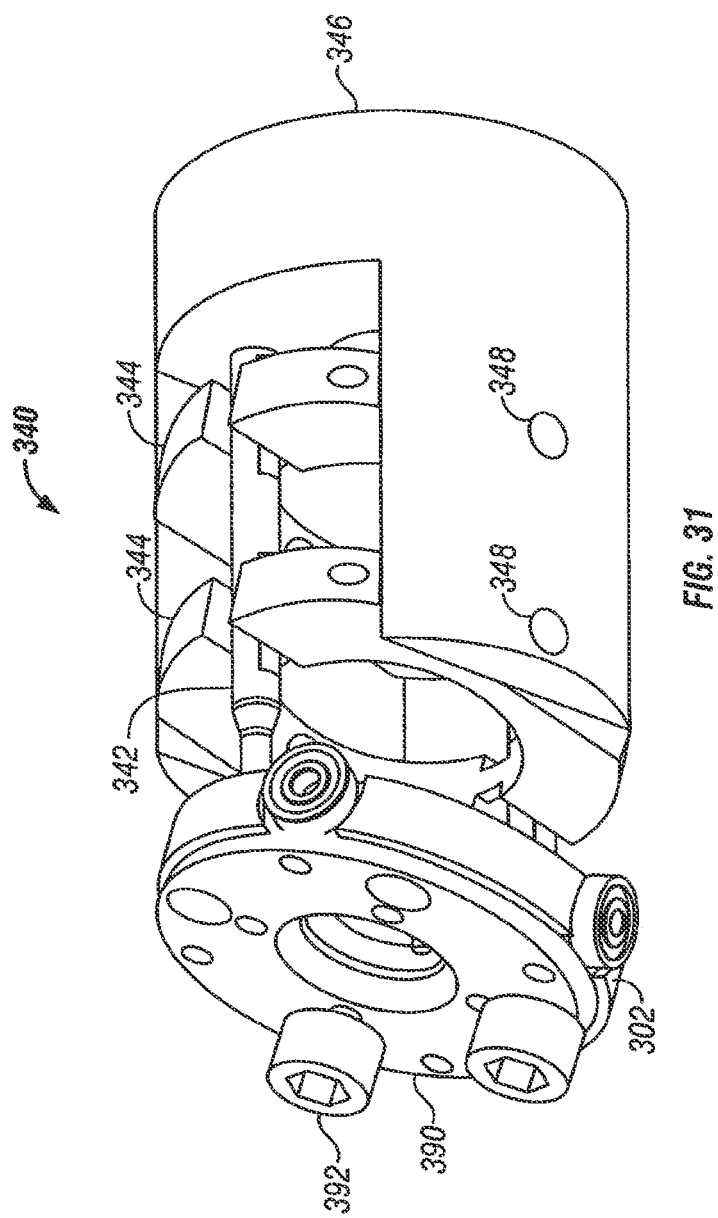
FIG. 31 is a perspective view of the parallel linkage of FIG. 30 illustrating the cover plate over the actuator plate.

As best seen in FIGS. 30 and 32, the actuator plate 302 includes eight small radius apertures 360 for receiving medial cables and eight large radius apertures 362 for receiving distal cables. FIG. 32 shows a medial cable 364 for illustrative purposes. The medial and distal actuation cables extend through the hollow center of the parallel linkage housing 346 and the hollow center of the shaft 370 (FIGS.

27 and 28), for instance, to the middle and distal disks 164, 166 of the PPMD wrist 160 of FIGS. 17-21.

FIG. 34 shows the gimbaled cable actuator 300 mounted on a lower housing member 380. FIG. 35 shows an upper housing member 382 mounted on the lower housing member 380. The upper housing member 382 includes pivots 384 for rotatably mounting the gear quadrants 314, 316. A cover plate 390 may be mounted over the actuator plate 302 by fasteners 392, as seen in FIGS. 27, 28, 31, 33, and 34.

Note that the most distal disk (e.g., disk 166 in FIGS. 17-21) may serve as a mounting base for various kinds of single-element and multi-element end effectors, such as scalpels, forceps, scissors, cautery tools, retractors, and the like. The central lumen internal to the disks may serve as a conduit for end-effector actuator elements (e.g., end effector actuator cables), and may also house fluid conduits (e.g., irrigation or suction) or electrical conductors.

Note that although gimbal ring support assembly 240 is shown in FIG. 26 for actuator plate 250, and an articulated gimbal-like structure 300 is shown in FIGS. 27-35 for actuator plate 302, alternative embodiments of the pivoted-plate cable actuator mechanism having aspects of the invention may have different structures and arrangements for supporting and controllably moving the actuator plate 250. For example the plate may be supported and moved by various types of mechanisms and articulated linkages to permit at least tilting motion in two DOF, for example a Stewart platform and the like. The plate assembly may be controllably actuated by a variety of alternative drive mechanisms, such as motor-driven linkages, hydraulic actuators; electromechanical actuators, linear motors, magnetically coupled drives and the like.

D. Grip Actuation Mechanism

Figure 36:
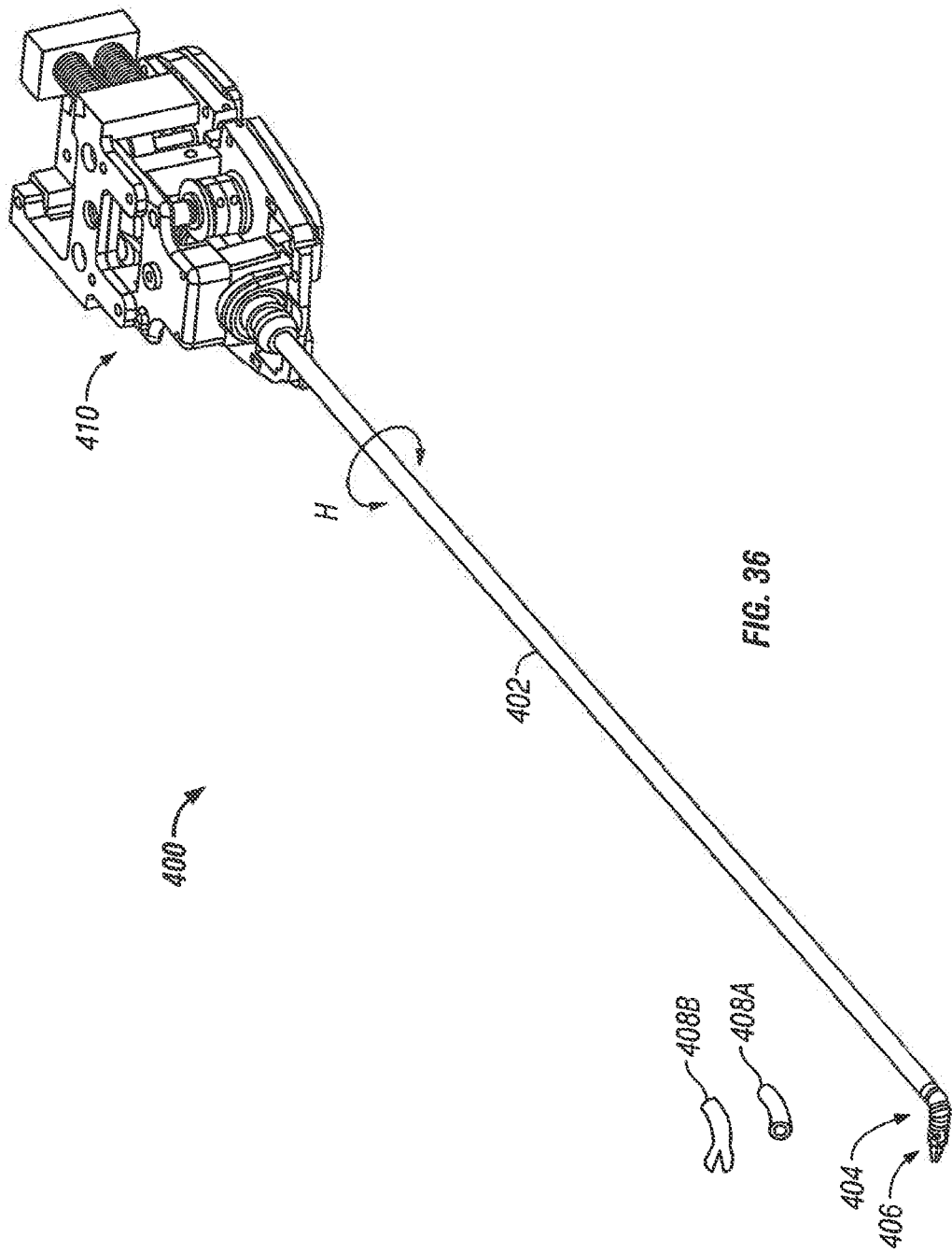
FIG. 36 is a perspective view of a surgical instrument according to an embodiment of the present invention.
Figure 37:
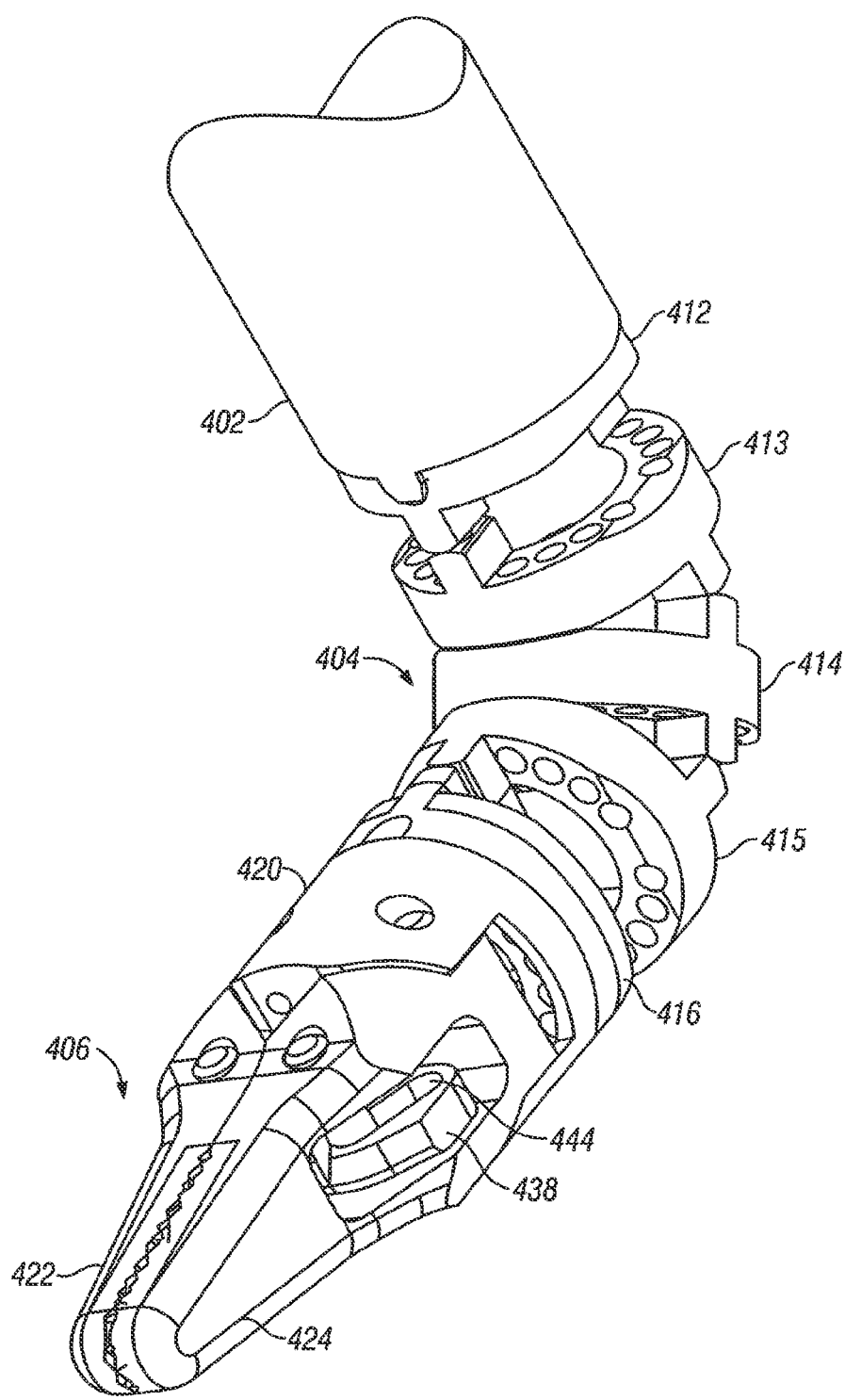
FIG. 37 is a perspective view of the wrist and end effector of the surgical instrument of FIG. 36.

FIG. 36 shows a surgical instrument 400 having an elongate shaft 402 and a wrist-like mechanism 404 with an end effector 406 located at a working end of the shaft 402. The wrist-like mechanism 404 shown is similar to the PPMD wrist 160 of FIGS. 17-21. The PPMD wrist has a lot of small cavities and crevices. For maintaining sterility, a sheath 408A may be placed over the wrist 404. Alternatively, a sheath 408B may be provided to cover the end effector 406 and the wrist 404.

A back end or instrument manipulating mechanism 410 is located at an opposed end of the shaft 402, and is arranged releasably to couple the instrument 400 to a robotic arm or system. The robotic arm is used to manipulate the back end mechanism 410 to operate the wrist-like mechanism 404 and the end effector 406. Examples of such robotic systems are found in various related applications as listed above, such as PCT International Application No. PCT/US98/19508, entitled "Robotic Apparatus", filed on Sep. 18, 1998, and published as WO99/50721; and U.S. patent application Ser. No. 09/398,958, entitled "Surgical Tools for Use in Minimally Invasive Telesurgical Applications", filed on Sep. 17, 1999. In some embodiments, the shaft 402 is rotatably coupled to the back end mechanism 410 to enable angular displacement of the shaft 402 relative to the back end mechanism 410 as indicated by arrows H.

Figure 38:
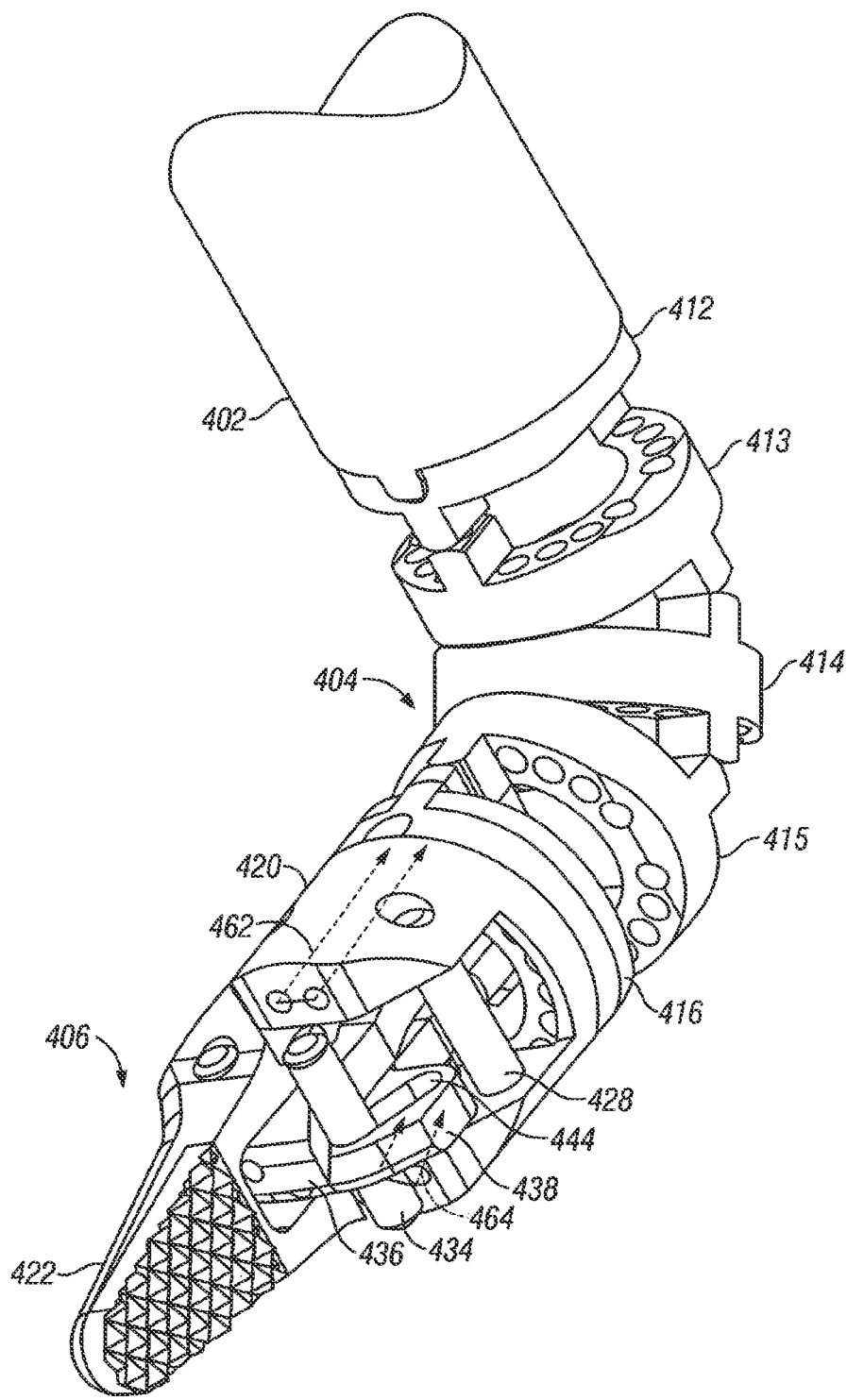
FIG. 38 is a partially cut-out perspective view of the wrist and end effector of the surgical instrument of FIG. 36.
Figure 39:
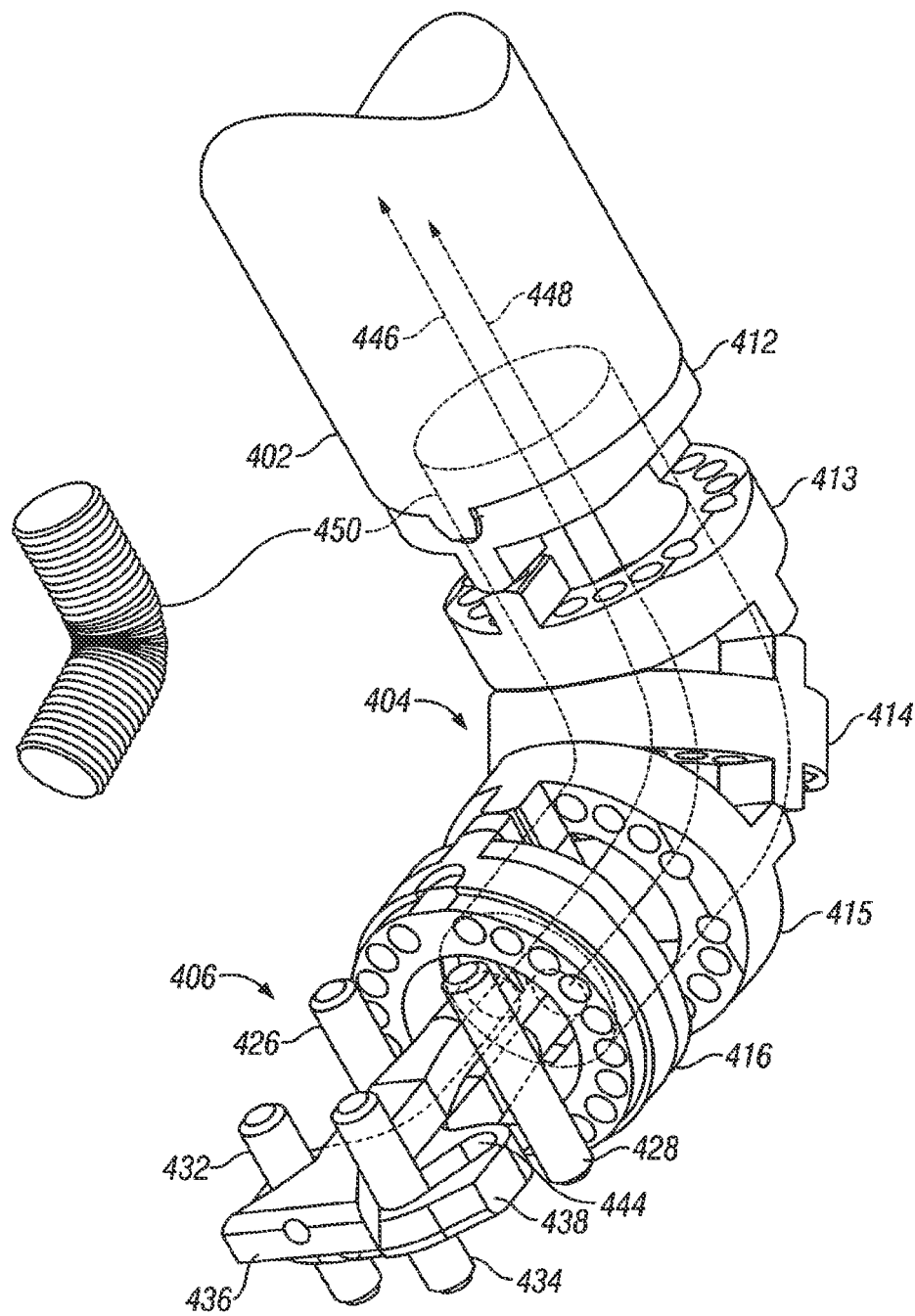
Figure 40:
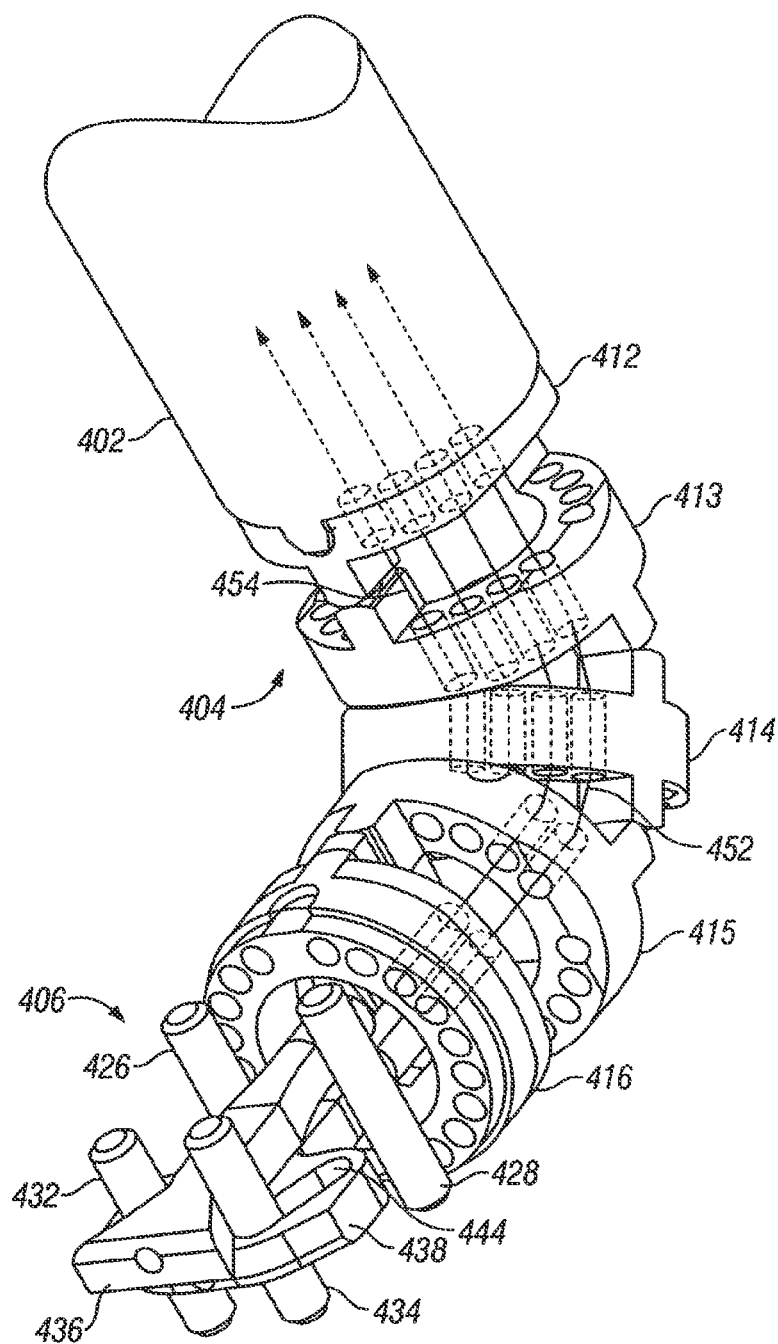
FIG. 40 is the perspective view of FIG. 39 illustrating wrist control cables.

The wrist-like mechanism 404 and end effector 406 are shown in greater detail in FIGS. 27-41. The wrist-like mechanism 404 is similar to the PPMD wrist 160 of FIGS. 17-21, and includes a first or proximal disk 412 connected to the distal end of the shaft 402, a second disk 413, a third or middle disk 414, a fourth disk 415, and a fifth or distal disk 416. A grip support 420 is connected between the distal disk 416 and the end effector 406, which includes a pair of working members or jaws 422, 424. To facilitate grip movement, the jaws 422, 424 are rotatably supported by the grip support 420 to rotate around pivot pins 426, 428, respectively, as best seen in FIGS. 38-40. Of course, other end effectors may be used. The jaws 422, 424 shown are merely illustrative.

Figure 39A:
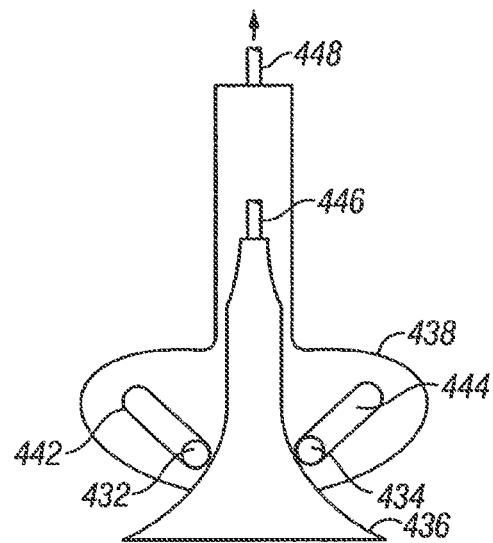
FIGS. 39A and 39B are plan views illustrating the opening and closing actuators for the end effector of the surgical instrument of FIG. 36.
Figure 39B:
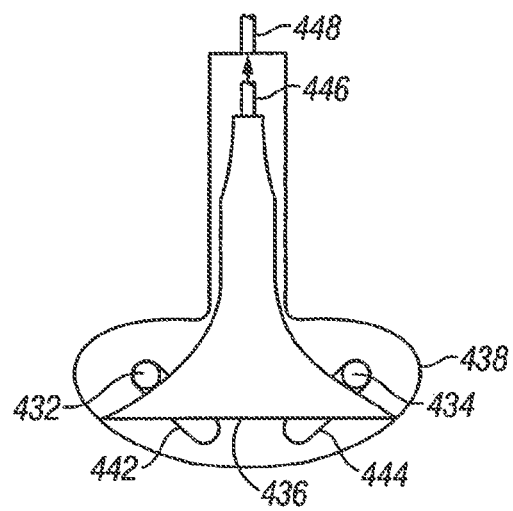

The grip movement is produced by a pair of slider pins 432, 434 connected to the jaws 422, 424, respectively, an opening actuator 436, and a closing actuator 438, which are best seen in FIGS. 38-40. The slider pins 432, 434 are slidable in a pair of slots 442, 444, respectively, provided in the closing actuator 438. When the slider pins 432, 434 slide apart outward along the slots 442, 444, the jaws 422, 424 open in rotation around the pivot pins 426, 428. When the slider pins 432, 434 slide inward along the slots 442, 444 toward one another, the jaws 422, 424 close in rotation around the pivot pins 426, 428. The sliding movement of the slider pins 432, 434 is generated by their contact with the opening actuator 436 as it moves relative to the closing actuator 438. The opening actuator 436 acts as a cam on the slider pins 432, 434. The closing of the jaws 422, 424 is produced by pulling the closing actuator 438 back toward the shaft 402 relative to the opening actuator 436 using a closing actuator cable 448, as shown in FIG. 39A. The opening of the jaws 422, 424 is produced by pulling the opening actuator 436 back toward the shaft 402 relative to the closing actuator 438 using an opening actuator cable 446, as shown in FIG. 39B. The opening actuator cable 446 is typically crimped into the hollow tail of the opening actuator 436, and the closing actuator cable 448 is typically crimped into the hollow tail of the closing actuator 438. In a specific embodiment, the opening actuator cable 446 and the closing actuator cable 448 are moved in conjunction with one another, so that the opening actuator 436 and the closing actuator 438 move simultaneously at an equal rate, but in opposite directions. The actuation cables 446, 448 are manipulated at the back end mechanism 410, as described in more detail below. The closing actuator 438 is a slotted member and the closing actuator cable 446 may be referred to as the slotted member cable. The opening actuator 436 is a slider pin actuator and the opening actuator cable 448 may be referred to as the slider pin actuator cable.

Figure 39C:
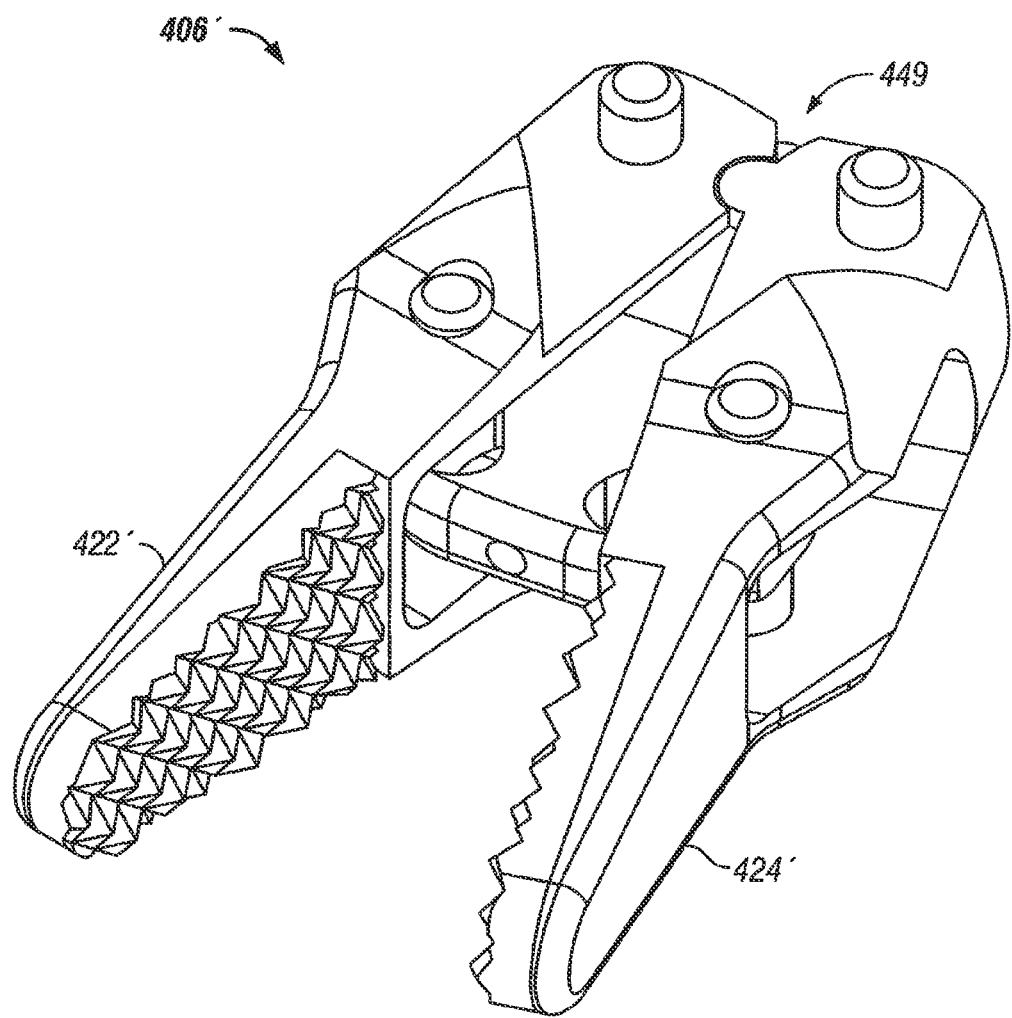
FIG. 39C is a perspective view of an end effector according to another embodiment.

To ensure that the grip members or jaws 422', 424' move symmetrically, an interlocking tooth mechanism 449 may be employed, as illustrated in FIG. 39C. The mechanism 449 includes a tooth provided on the proximal portion of one jaw 424' rotatably coupled to a slot or groove provided in the proximal portion of the other jaw 424'. The mechanism 449 includes another interlocking tooth and slot on the opposite side (not shown) of the jaws 422', 424'.

A plurality of long or distal cables and a plurality of short or medial cables, similar to those shown in FIG. 5, are used to manipulate the wrist 404. FIG. 40 shows one distal cable 452 and one medial cable 454 for illustrative purposes. Each cable (452, 454) extends through adjacent sets of apertures with free ends extending proximally through the tool shaft 402, and makes two passes through the length of the wrist 404. There are desirably a total of four distal cables and four medial cables alternatively arranged around the disks 412-416.

The actuation cables 446, 448 and the wrist control cables such as 452, 454 pass through the lumen formed by the annular disks 412-416 back through the shaft 402 to the back end mechanism 410, where these cables are manipulated. In some embodiments, a conduit 450 is provided in the lumen formed by the annular disks 412-416 (see FIG. 39) to minimize or reduce cable snagging or the like. In a specific embodiment, the conduit 450 is formed by a coil spring connected between the proximal disk 412 and the distal disk 416. The coil spring bends with the disks 412-416 without interfering with the movement of the disks 412-416.

Figure 38A:
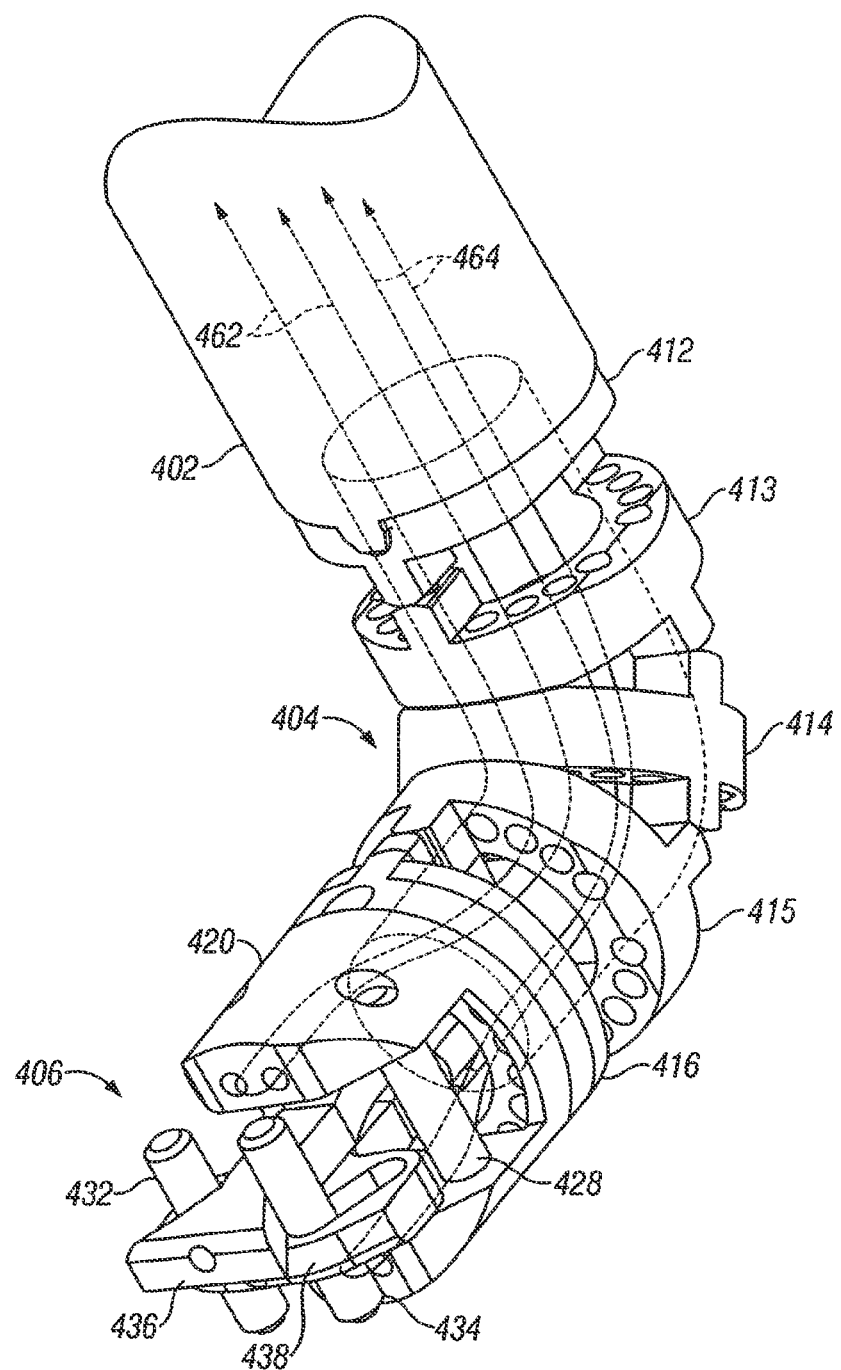
FIGS. 38A and 39 are additional partially cut-out perspective views of the wrist and end effector of the surgical instrument of FIG. 36.

The grip support 420 may be fastened to the wrist 404 using any suitable method. In one embodiment, the grip support 420 is held tightly to the wrist 404 by support cables 462, 464, as illustrated in FIGS. 38 and 38A. Each support cable extends through a pair of adjacent holes in the grip support 420 toward the wrist 404. The support cables 462, 464 also pass through the lumen formed by the annular disks 412-416 back through the shaft 402 to the back end mechanism 410, where they are secured.

Figure 41:
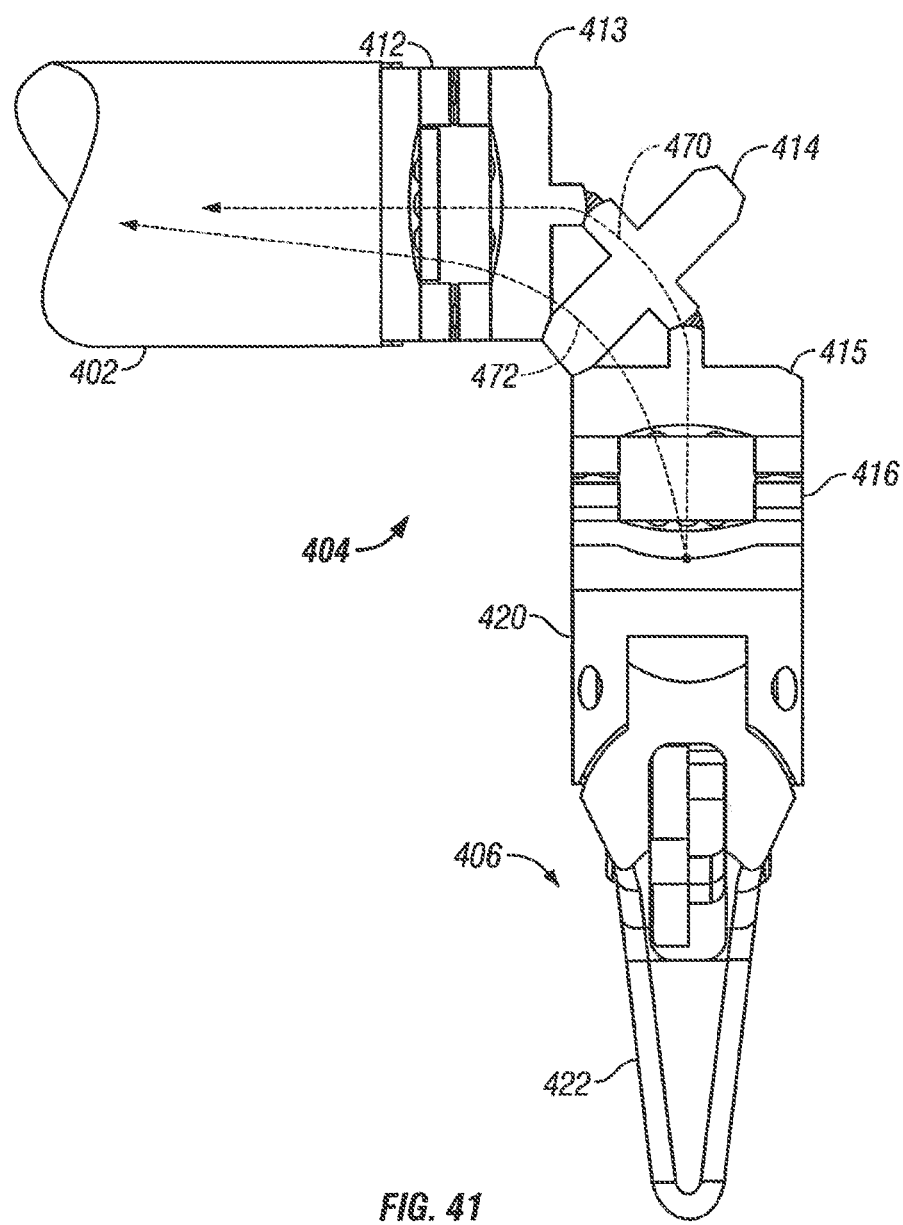
FIG. 41 is an elevational view of the wrist and end effector of the surgical instrument of FIG. 36.

Referring to FIG. 41, the wrist 404 has a wrist central axis or neutral axis 470 that is fixed in length during bending of the wrist 404. The various cables, however, vary in length during bending of the wrist 404 as they take on cable paths that do not coincide with the neutral axis, such as the cable path 472 shown. Constraining the cables to bend substantially along the neutral axis 470 (e.g., by squeezing down the space in the wrist 404) reduces the variation in cable lengths, but will tend to introduce excessive wear problems. In some embodiments, the change in cable lengths will be accounted for in the back end mechanism 410, as described below.

FIGS. 42-46 show a back end mechanism 410 according to an embodiment of the present invention. One feature of this embodiment of the back end mechanism 410 is that it allows for the replacement of the end effector 406 (e.g., the working members or jaws 422, 424, the actuators 436, 438, and the actuation cables 446, 448) with relative ease.

Figure 42:
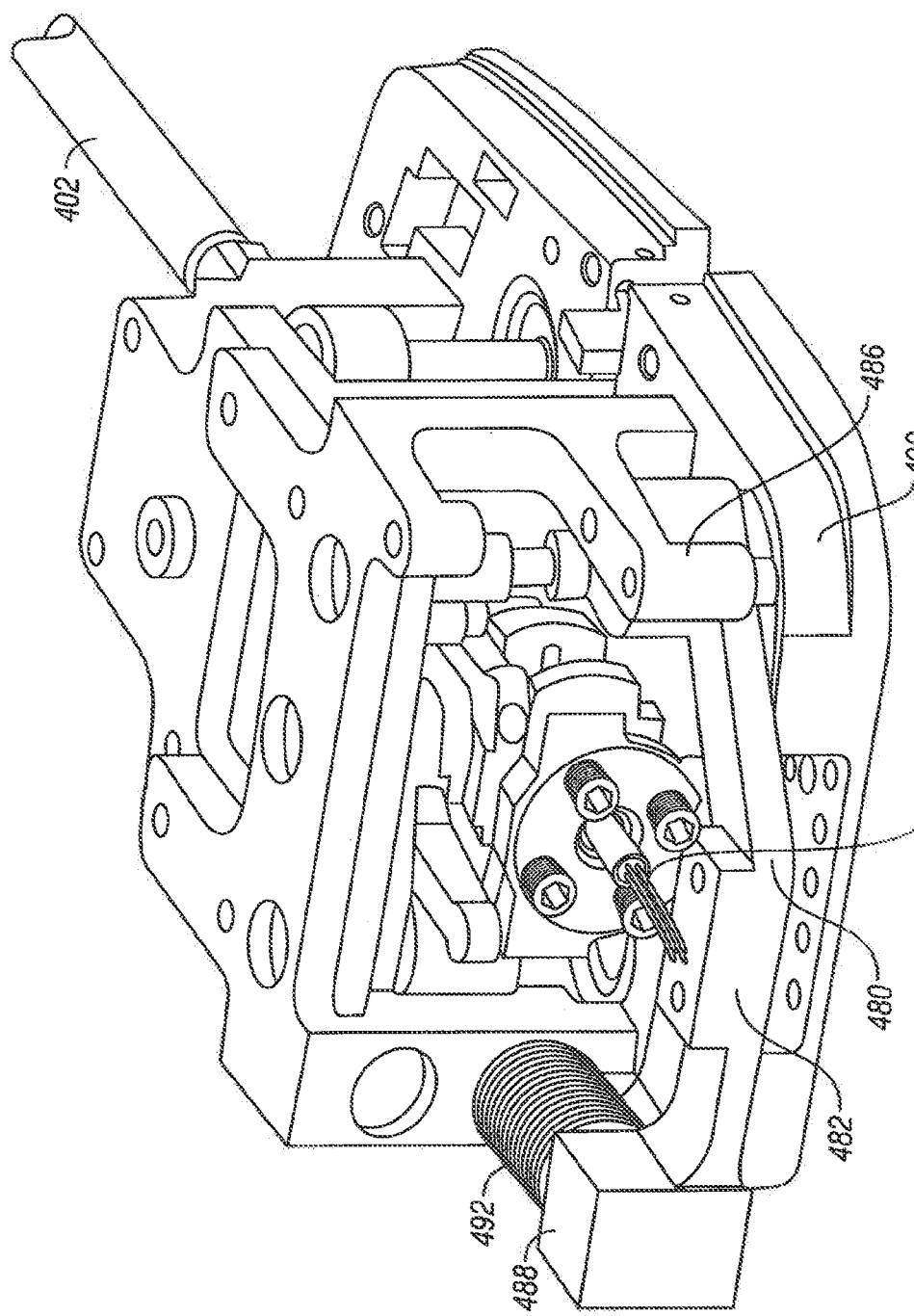
FIG. 42 is a perspective view of a back end mechanism of the surgical instrument of FIG. 36 according to an embodiment of the present invention.

As shown in FIG. 42, the support cables 462, 464 (see FIGS. 38 and 38A) used to hold the grip support 420 to the wrist 404 extend through a central tube after passing through the shaft 402. The support cables 462, 464 are clamped to a lower arm 480 and lower clamp block 482 which are screwed tight. The lower arm 480 includes a pivot end 486 and a spring attachment end 488. The pivot end 486 is rotatably mounted to the back end housing or structure 490, as shown in FIG. 42. The spring attachment end 488 is connected to a spring 492 which is fixed to the back end housing 490. The spring 492 biases the lower arm 480 to apply tension to the support cables 462, 464 to hold the grip support 420 tightly to the wrist 404.

Figure 43:
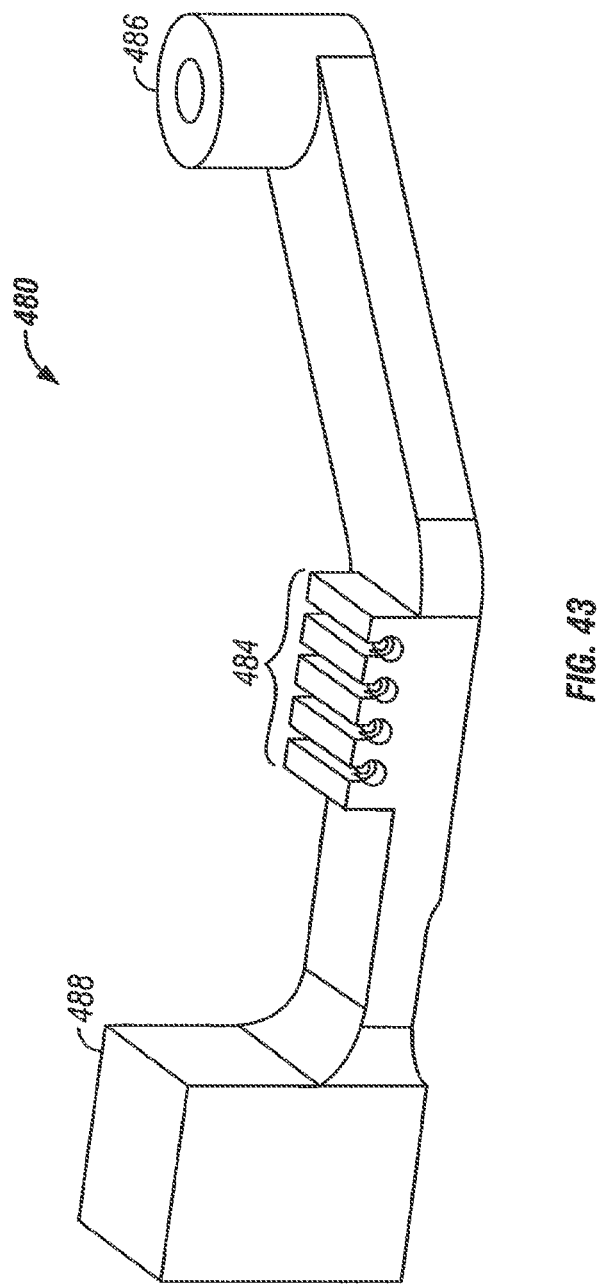
FIG. 43 is a perspective view of a lower member in the back end mechanism of FIG. 42 according to an embodiment of the present invention.

FIG. 43 shows another way to secure the support cables 462, 464 by using four recesses or slots 484 in the lower arm 480 instead of the clamp block 482. A sleeve is crimped onto each of the ends of the support cables 462, 464, and the sleeves are tucked into the recesses or slots 484. This is done by pushing the lower arm 480 inward against the spring force, and slipping the sleeved cables into their slots.

Figure 44:
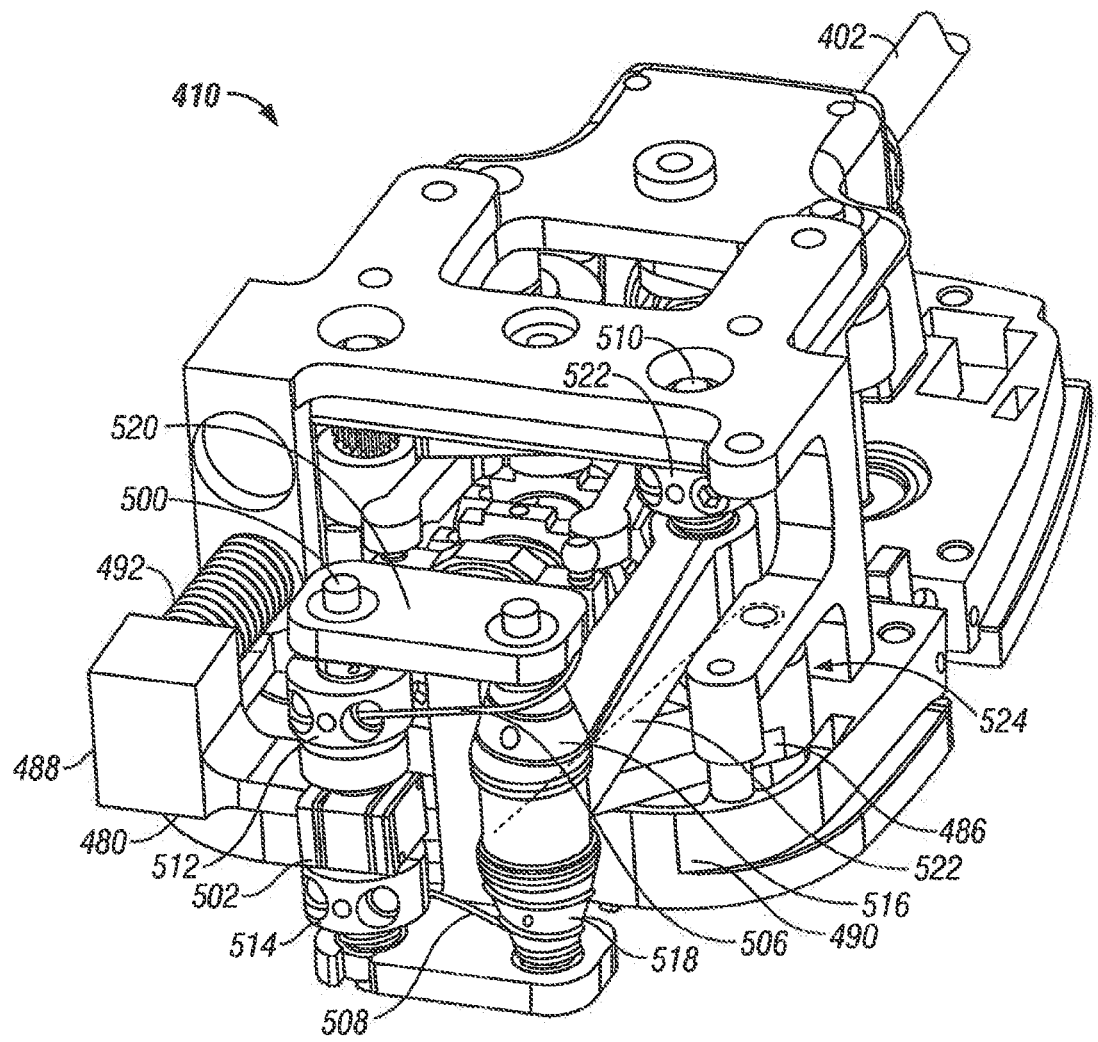
FIGS. 44-46 are perspective views of the back end mechanism according to another embodiment of the present invention.

FIG. 44 shows an additional mechanism that allows the lengths of the actuation cables 446, 448 (see FIG. 39) to change without affecting the position of the grip jaws 422, 424. The actuation cables 446, 448 extending through the shaft 402 are clamped to a grip actuation pivoting shaft 500 at opposite sides of the actuation cable clamping member 502 with respect to the pivoting shaft 500. The clamping member 502 rotates with the grip actuation pivoting shaft 500 so as to pull one actuation cable while simultaneously releasing the other to operate the jaws 422, 424 of the end effector 406.

Figure 47:
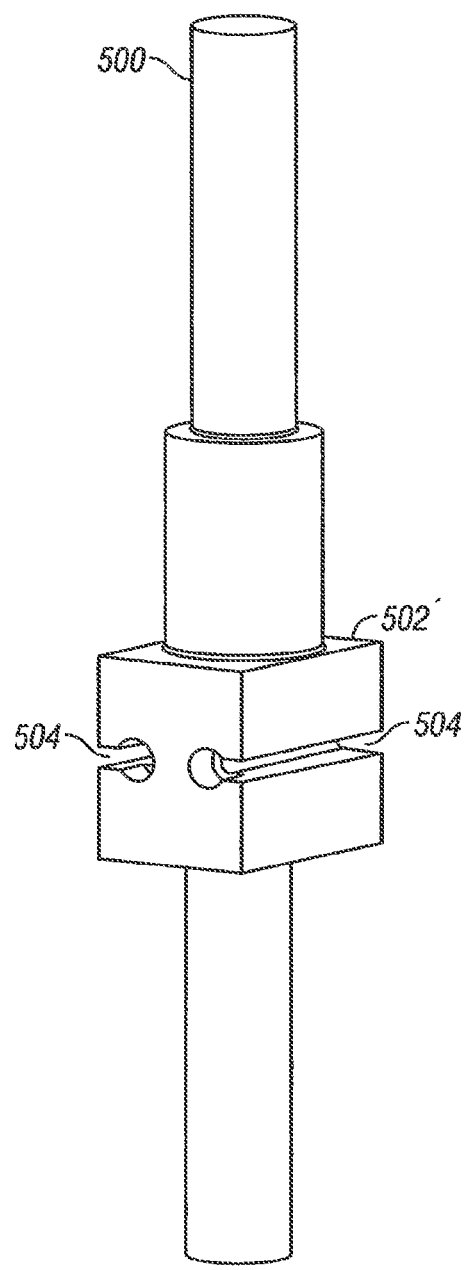
FIG. 47 is a perspective view of a mechanism for securing the actuation cables in the back end of the surgical instrument of FIGS. 44-46 according to another embodiment of the present invention.

Instead of the clamping member 502 for clamping the actuation cables 446, 448, a different cable securing member 502' may be used for the grip actuation pivot shaft 500, as shown in FIG. 47. The cable securing member 502' includes a pair of oppositely disposed recesses or slots 504. A sleeve is crimped onto each of the ends of the actuation cables 446, 448, and the sleeves are tucked into the recesses or slots 504. This is done by pushing the upper arm 530 inward against the spring force, and slipping the sleeved cables into their slots.

Figure 45:
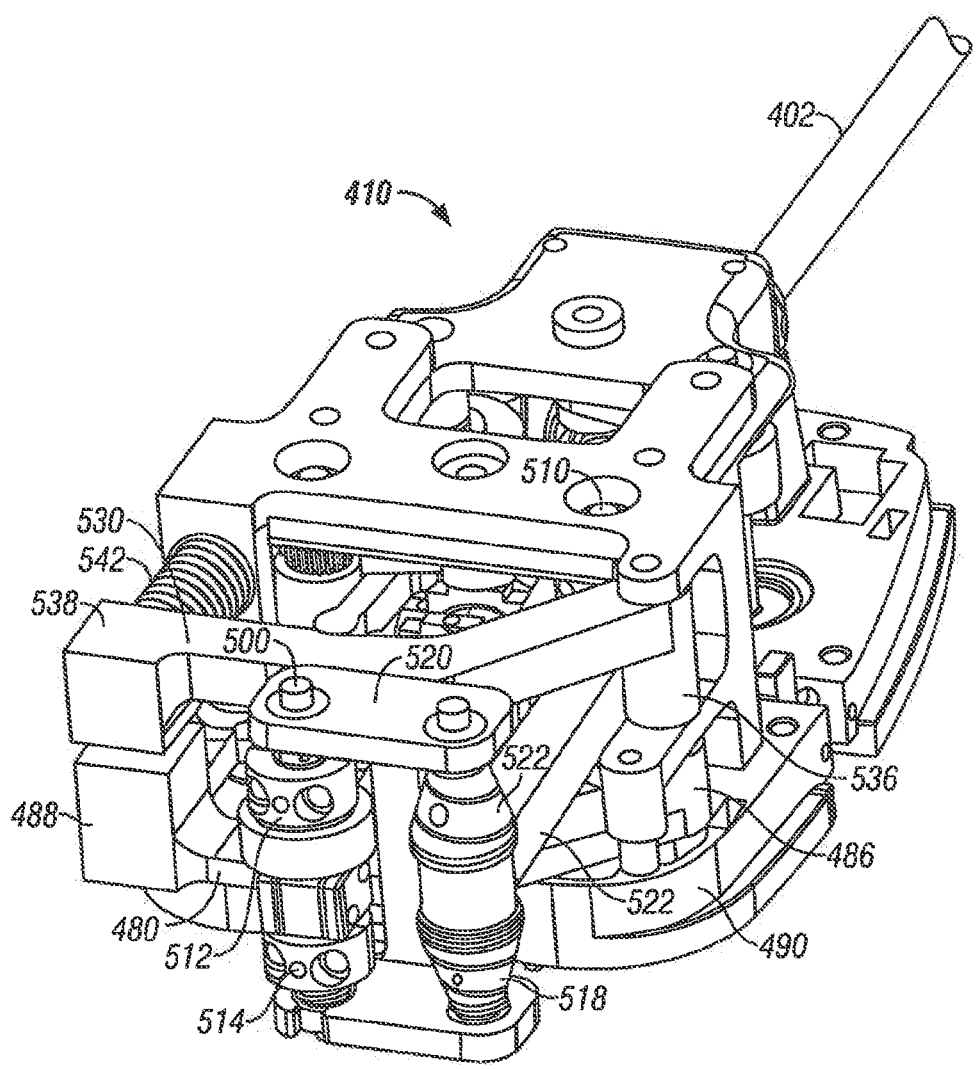
Figure 46:
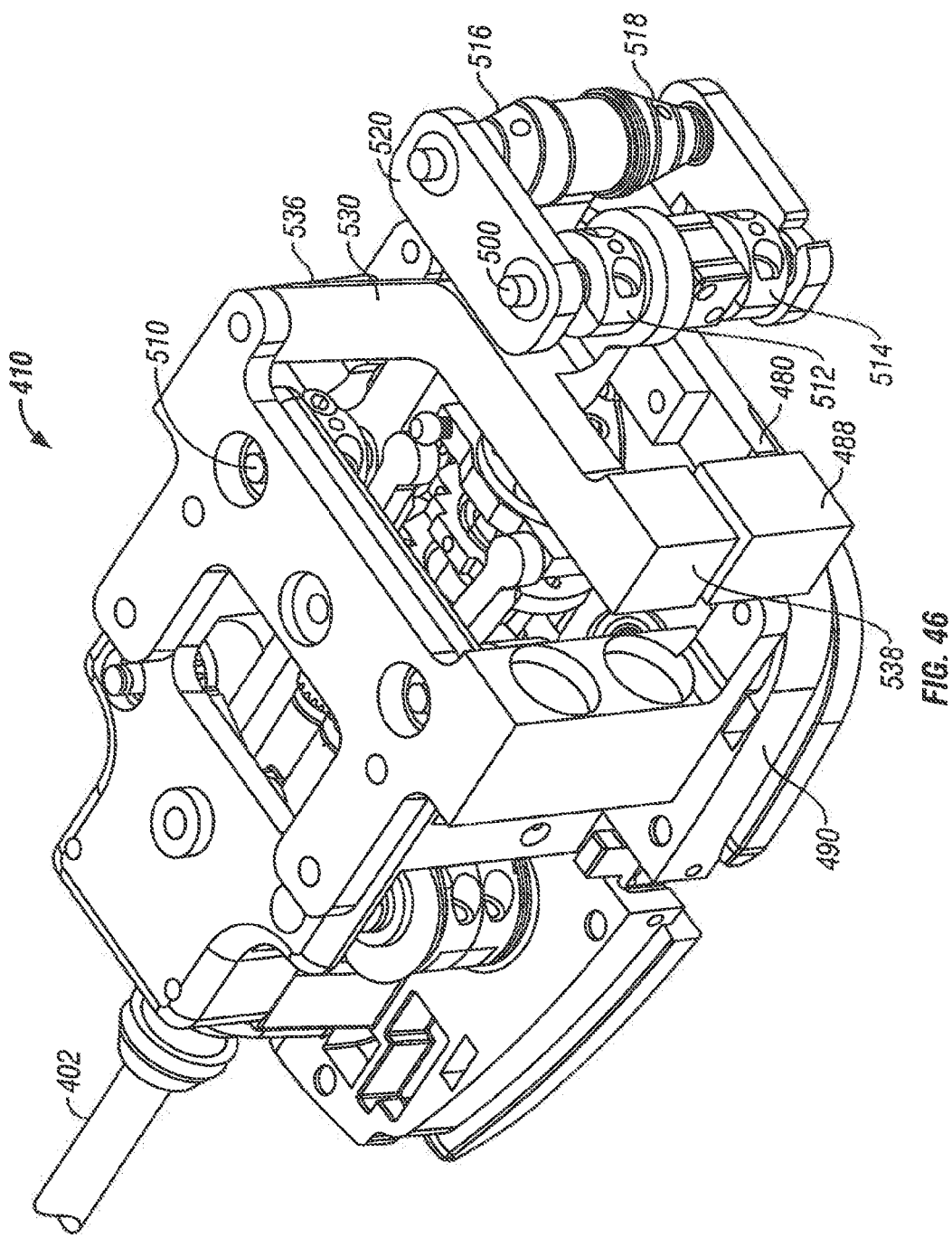

As shown in FIGS. 44-46, the grip actuation pivot shaft 500 is controlled by a pair of control cables 506, 508 that are connected to the motor input shaft 510. The two control cables 506, 508 are clamped to the grip actuation pivot shaft 500 by two hub clamps 512, 514, respectively. From the hub clamps 512, 514, the control cables 506, 508 travel to two helical gear reduction idler pulleys 516, 518, and then to the motor input shaft 510, where they are secured by two additional hub clamps 522, 524. As shown in FIG. 44, the two control cables 506, 508 are oppositely wound to provide the proper torque transfer in both clockwise and counter-clockwise directions. Rotation of the motor input shaft 510 twists the grip actuation pivot shaft 500 via the control cables 506, 508, which in turn pulls one actuation cable while simultaneously releasing the other, thereby actuating the jaws 422, 424 of the end effector 406.

The grip actuation pivot shaft 500 and the pair of helical gear reduction idler pulleys 516, 518 are pivotally supported by a link box 520. The link box 520 is connected to a link beam 522, which is pivotally supported along the axis of the motor input shaft 510 to allow the grip actuation pivot shaft 500 to move back and forth to account for change in cable length due to bending of the wrist 404, without changing the relative position of the two actuation cables 446, 448 that control the grip jaws 422, 424. This feature decouples the control of the grip jaws 422, 424 from the bending of the wrist 404.

FIGS. 45 and 46 show the addition of an upper arm 530 which is similar to the lower arm 480. The upper arm 530 also has a pivot end 536 and a spring attachment end 538. The pivot end 536 is rotatably mounted to the back end housing 490 along the same pivot axis as the pivot end 486 of the lower arm 480. The upper arm 530 is connected to the grip actuation pivot shaft 500. The spring attachment end 538 is connected to a spring 542 which is fixed to the back end housing 490. The spring 542 biases the upper arm 530 to apply a pretension to the actuation cables 446, 448. The springs 492, 542 are not shown in FIG. 46 for simplicity and clarity.

The configuration of the back end mechanism 410 facilitates relatively easy replacement of the actuators 436, 438 and actuation cables 446, 448, as well as the working members or jaws 422, 424. The cables can be released from the back end mechanism 410 with relative ease, particularly when the cables are secured to recesses by crimped sleeves (see FIGS. 43, 47).

Figure 48:
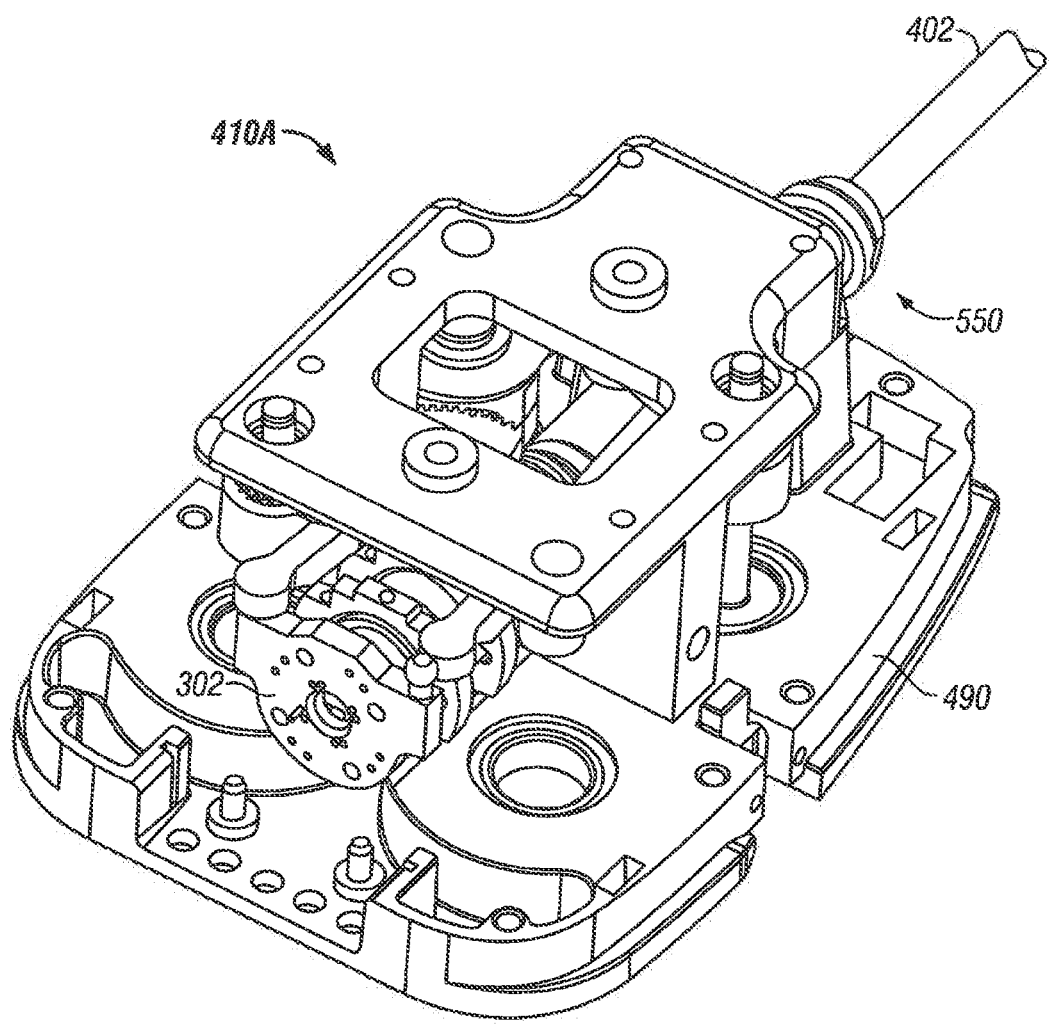
FIG. 48 is a perspective view of a back end mechanism of the surgical instrument of FIG. 36 according to another embodiment of the present invention.

In another embodiment of the back end mechanism 410A as shown in FIG. 48, not only the end effector 406 but the wrist 404 and the shaft 402 may also be replaced with relative ease. As shown in FIGS. 27-35 and described above, the wrist cables (e.g., the distal cable 452 and medial cable 454 in FIG. 40) for actuating the wrist 404 all terminate at the back end on a circular ring of the actuator plate 302. The wrist cables are clamped to the actuator plate 302 with a cover plate 390 (see FIGS. 27-35).

To achieve the replaceable scheme of the wrist 404 and shaft 402, the wrist cables are fastened to a smaller plate (e.g., by clamping), and the smaller plate is fed from the instrument from the front 550 of the back end housing 490 and affixed to the actuator plate 302.

In an alternate configuration, the actuator plate 302 may be repositioned to the front 550 of the back end housing 490 to eliminate the need to thread the smaller plate through the length of the shaft 402.

Figure 49:
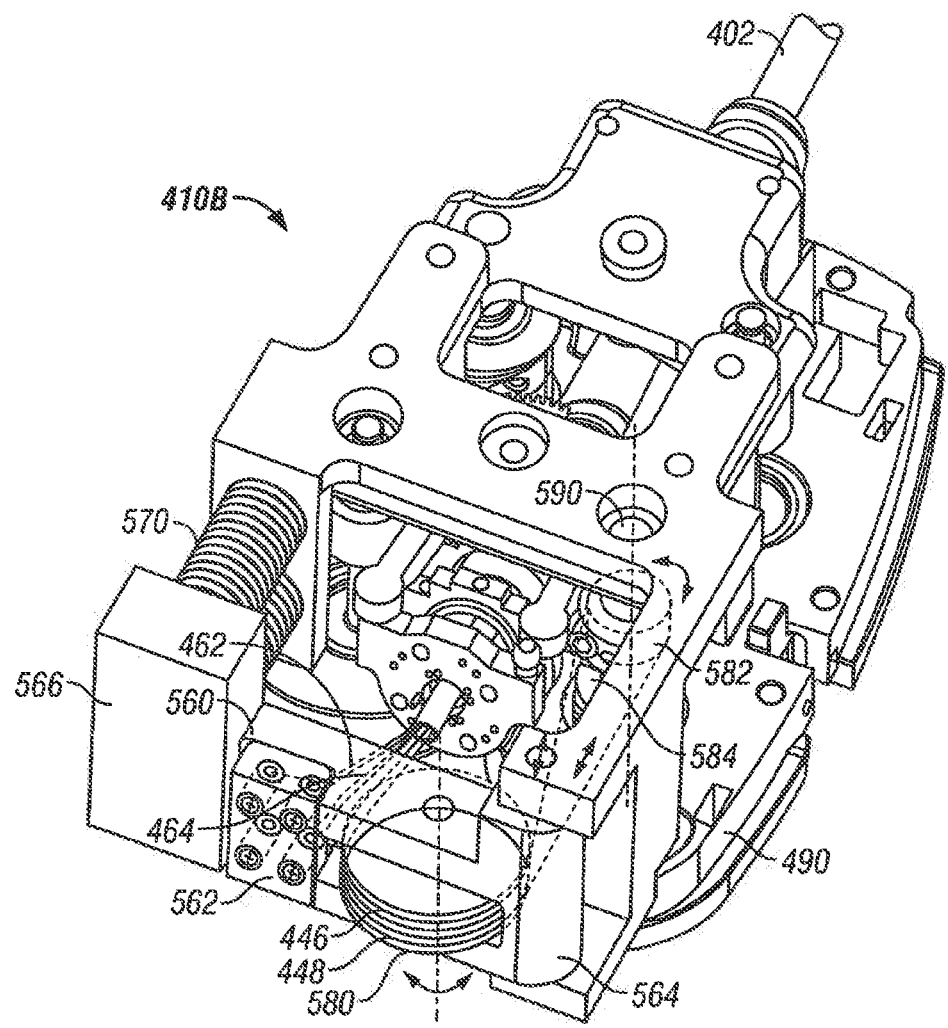
FIGS. 49 and 50 are perspective views of a back end mechanism of the surgical instrument of FIG. 36 according to another embodiment of the present invention.
Figure 50:
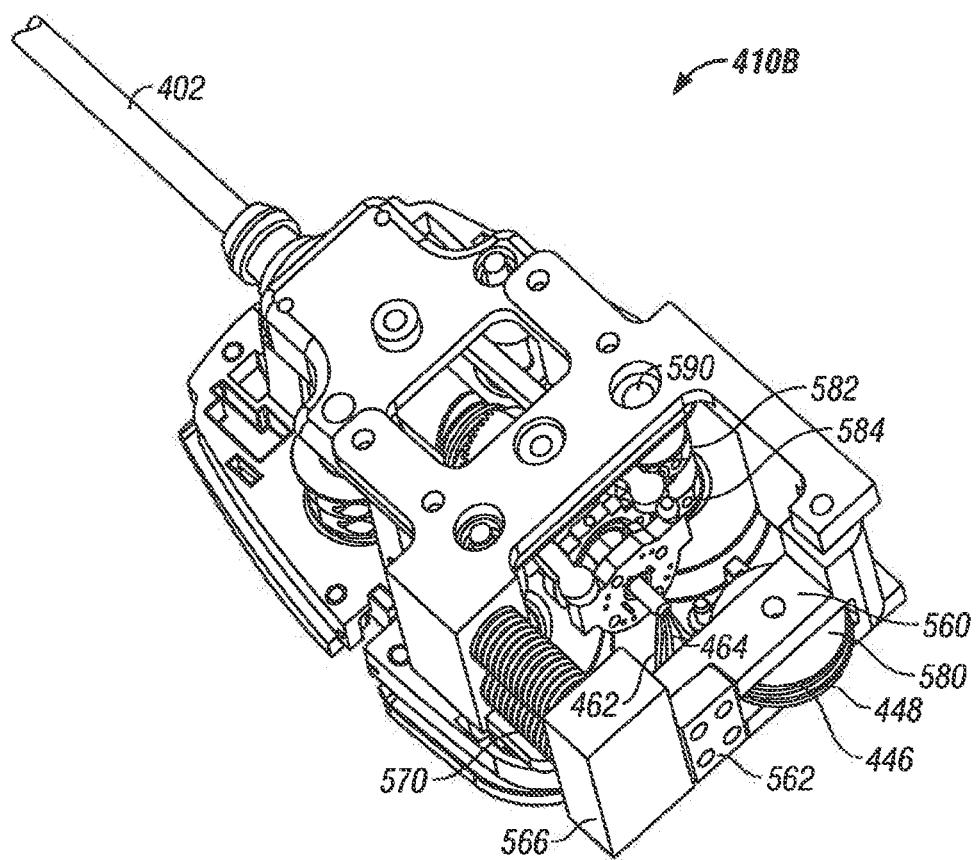

FIGS. 49 and 50 show another back end mechanism 410B illustrating another way of securing the cables. The support cables 462, 464 (see FIGS. 38 and 38A) are clamped to the arm 560 by a clamping block 562. The arm 560 has a pivot end 564 and a spring attachment end 566. The pivot end 564 is rotatably mounted to the back end housing or structure 490. The spring attachment end 566 is connected to one or more springs 570 which are fixed to the back end housing 490. The springs 570 bias the arm 560 to apply tension to the support cables 462, 464 to hold the grip support 420 tightly to the wrist 404.

The actuation cables 446, 448 (see FIG. 39) extend around pulleys 580 connected to the arm 560, and terminate at a pair of hub clamps 582, 584 provided along the motor input shaft 590. This relatively simple arrangement achieves the accommodation of cable length changes and pretensioning of the cables. The support cables 462, 464 are tensioned by the springs 570. The actuation cables 446, 448 are tensioned by applying a torque to the hub clamps 582, 584. The replacement of the end effector 406 and wrist 404 will be more difficult than some of the embodiments described above.

E. A More Compact Embodiment

Figure 51:
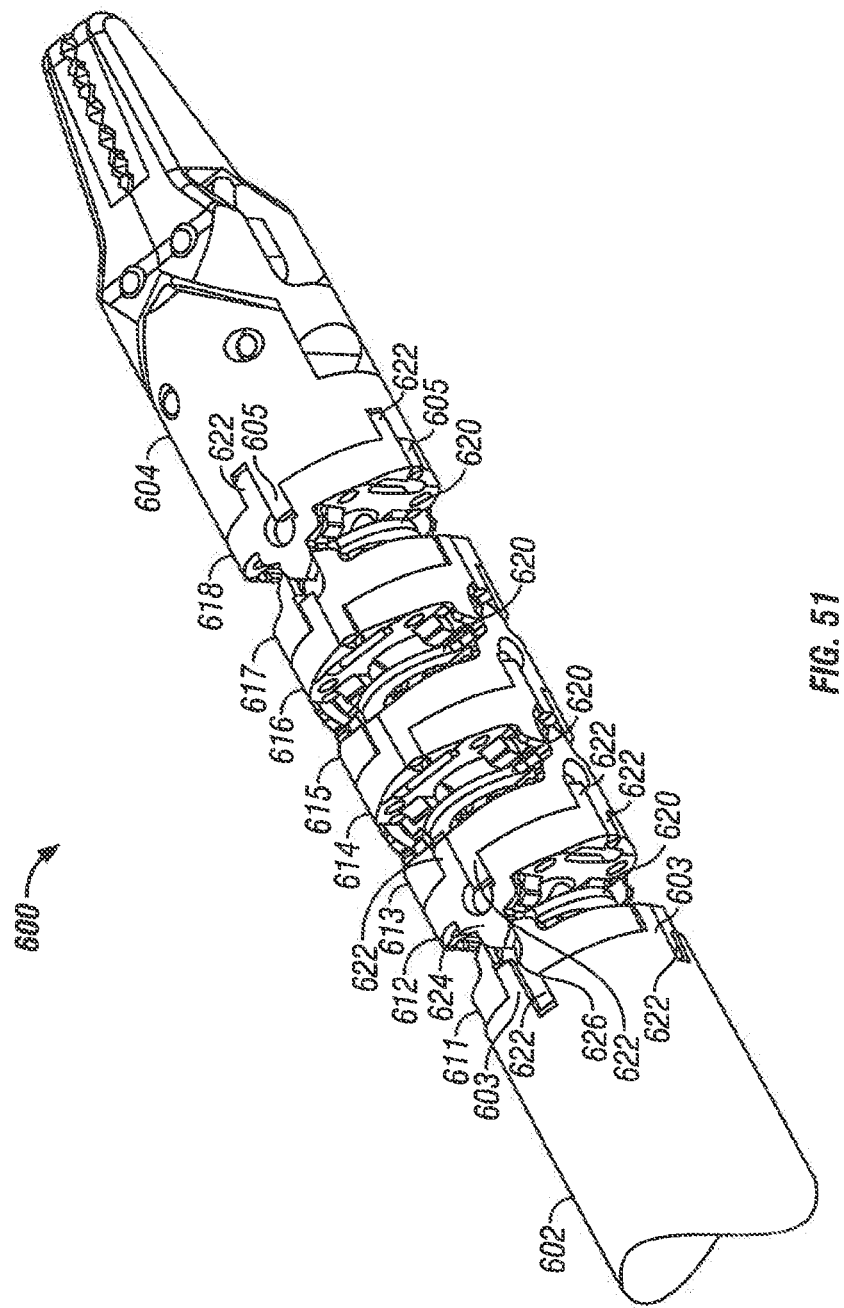
FIG. 51 is a perspective of a PPMD wrist according to another embodiment.
Figure 52:
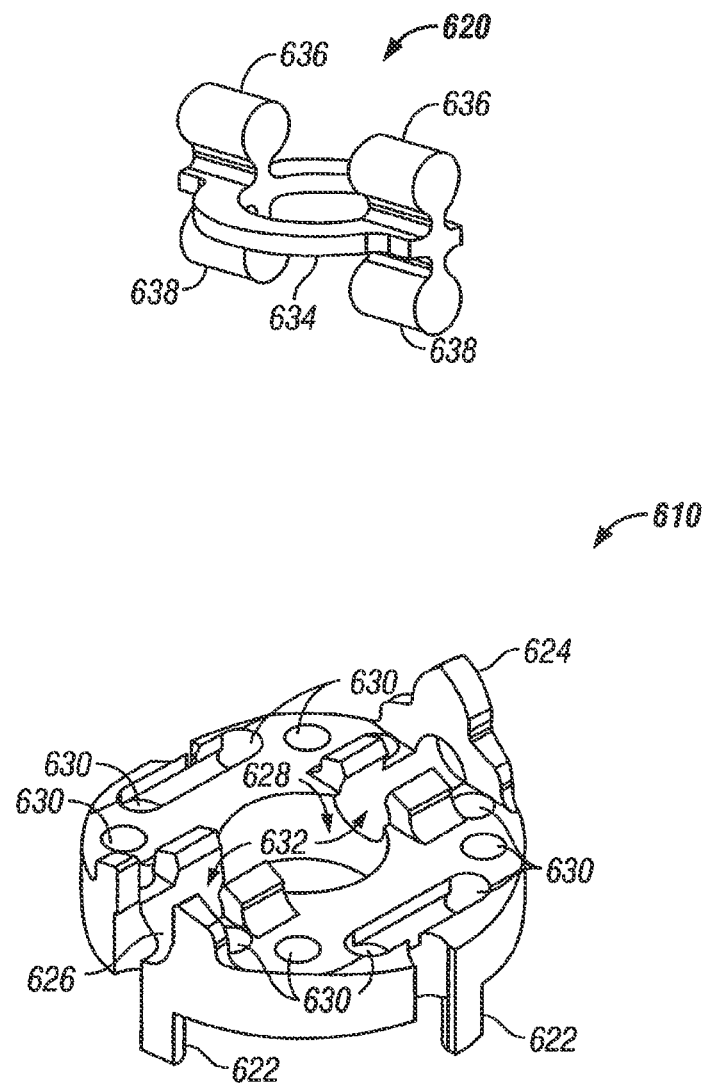
FIG. 52 is an exploded view of a vertebra or disk segment in the PPMD wrist of FIG. 51.
Figure 57:
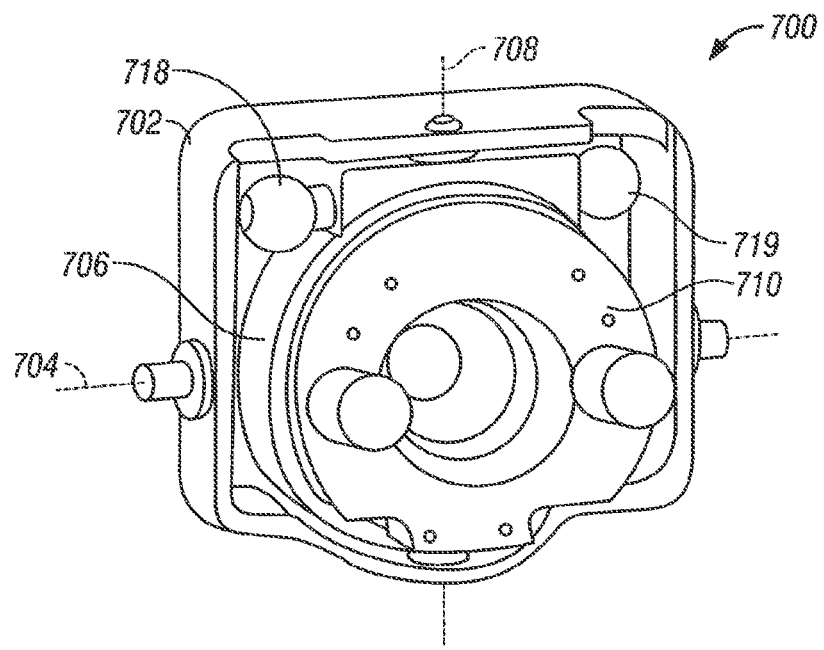
FIGS. 57 and 58 are perspective views of a gimbaled cable actuator according to another embodiment.
Figure 58:
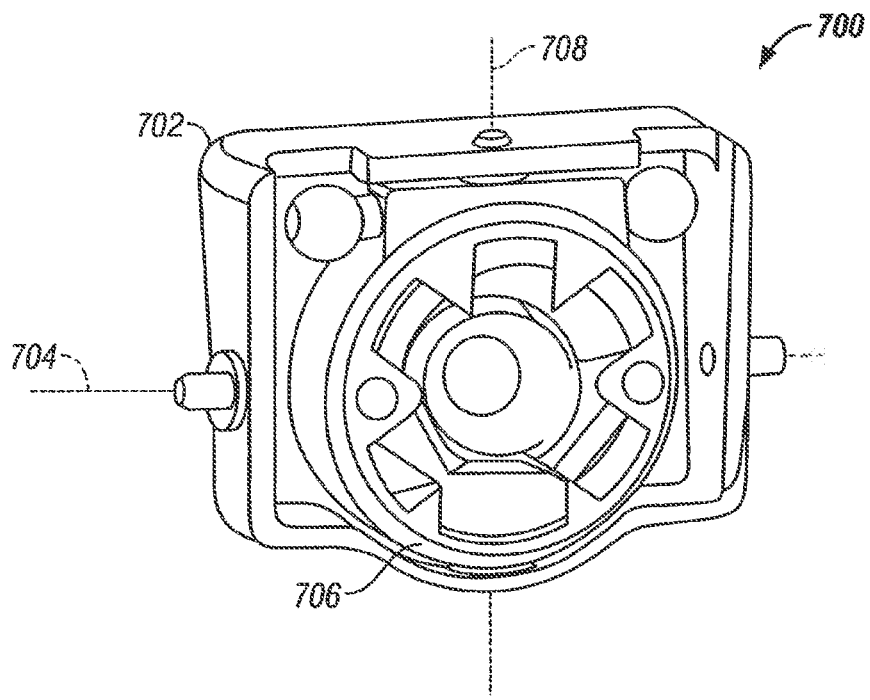

FIGS. 51-67 illustrate another PPMD wrist tool that is designed to have certain components that are more compact or easier to manufacture or assemble. As shown in FIGS. 51-56, the PPMD wrist 600 connected between a tool shaft 602 and an end effector 604. The wrist 600 includes eight nested disk segments 611-618 that are preferably identical, which improves manufacturing efficiency and cost-effectiveness. An individual disk segment 610 is seen in FIG. 52. Four struts 620 are provided, each of which is used to connect a pair of disk segments together. An individual strut 620 is shown in FIG. 52.

The disk segment 610 includes a mating side having a plurality of mating extensions 622 extending in the axial direction (four mating extensions spaced around the circumference in a specific embodiment), and a pivoting side having a gear tooth 624 and a gear slot 626. The gear tooth 624 and gear slot 626 are disposed on opposite sides relative to a center opening 628. Twelve apertures 630 are distributed around the circumference of the disk segment 610 to receive cables for wrist actuation, as described in more detail below. The disk segment 610 further includes a pair of radial grooves or slots 632 disposed on opposite sides relative to the center opening 628. In the specific embodiment shown, the radial grooves 632 are aligned with the gear tooth 624 and gear slot 626.

The strut 620 includes a ring 634, a pair of upper radial plugs or projections 636 disposed on opposite sides of the ring 634, and a pair of lower radial plugs or projections 638 disposed on opposite sides of the ring 634. The upper radial projections 636 and lower radial projections 638 are aligned with each other.

To assemble a pair of disk segments 610 with the strut 620, the pair of lower radial projections 638 are inserted by sliding into the pair of radial grooves 632 of a lower disk segment. An upper disk segment is oriented in an opposite direction from the lower disk segment, so that the pivoting side with the gear tooth 624, gear slot 626, and radial grooves 632 faces toward the strut 620. The pair of upper radial projections 638 of the strut 620 are inserted by sliding into the pair of radial grooves 632 of the upper disk segment. In the specific embodiment, the radial projections and radial grooves are circular cylindrical in shape to facilitate pivoting between the disk segments. The gear tooth 624 of the lower disk segment is aligned with the gear slot 626 of the upper disk segment to pivot relative thereto, while the gear tooth 624 of the upper disk segment is aligned with the gear slot 626 of the lower disk segment to pivot relative thereto. This is best seen in FIG. 51. The movement between the gear tooth 624 and gear slot 626 is made by another nonattached contact.

The proximal or first disk segment 611 is connected to the end of the tool shaft 602 by the mating extensions 622 of the disk segment 611 and mating extensions 603 of the shaft 602. The second disk segment 612 is oriented opposite from the first disk segment 611, and is coupled to the first segment 611 by a strut 620. The gear tooth 624 of the second disk segment 612 is engaged with the gear slot 626 of the first disk segment 611, and the gear tooth 624 of the first disk segment 611 is engaged with the gear slot 626 of the second disk segment 612. The third disk segment 613 is oriented opposite from the second disk segment 612, with their mating sides facing one another and the mating extensions 622 mating with each other. The second disk segment 612 and the third disk segment 613 forms a whole disk. Similarly, the fourth disk segment 614 and fifth disk segment 615 form a whole disk, and the sixth disk segment 616 and the seventh disk segment 617 form another whole disk. The other three struts 620 are used to rotatably connect, respectively, third and fourth disk segments 613, 614; fifth and sixth disk segments 615, 616; and seventh and eighth disk segments 617, 618. The eighth or distal disk segment 618 is connected to the end effector 604 by the mating extensions 622 of the disk segment 618 and the mating extensions 605 of the end effector 604.

As more clearly seen in FIG. 53, the rotational coupling between the first disk segment 611 and second disk segment 612 provides pitch rotation 640 of typically about 45°, while the rotational coupling between the seventh disk segment 617 and eighth disk segment 618 provides additional pitch rotation 640 of typically about 45° for a total pitch of about 90°. The four disk segments in the middle are circumferentially offset by 90° to provide yaw rotation. As more clearly seen in FIG. 54, the rotational coupling between the third disk segment 613 and fourth disk segment 614 provides yaw rotation 642 of typically about 45°, while the rotational coupling between the fifth disk segment 615 and sixth disk segment 161 provides additional yaw rotation 642 of typically about 45° for a total yaw of about 90°. Of course, different orientations of the disk segments may be formed in other embodiments to achieve different combinations of pitch and yaw rotation, and additional disk segments may be included to allow the wrist to rotate in pitch and yaw by greater than 90°.

Note that the rotatable engagement of the pair of projections 638 of each strut 620 with a respective bearing surface of grooves 632 on each adjacent disk portion 610 assures a "dual pivot point" motion of adjacent disks with respect to one another, such that the pivot points are in coplanar alignment with the cable apertures 630. By this means, a "cable balancing" property is achieved, to substantially similar effect as is described above with respect to the embodiment of FIG. 25. This assures that the cable length paid out on one side is equal to the cable length pulled on the other side of the disk.

The disk segments of the wrist 600 are manipulated by six cables 650 extending through the apertures 630 of the disk segments, as shown in FIGS. 55 and 56. Each cable 650 passes through adjacent sets of apertures 630 to make two passes through the length of the wrist 600 in a manner similar to that shown in FIG. 40, with the free ends extending through the tool shaft to the back end, where the cables are manipulated. The six cables include three long or distal cables and three short or medial cables that are alternately arranged around the disk segments. An internal lumen tube 654 may be provided through the center of the wrist 600 and extend through the interior of the tool shaft 602, which is not shown in FIGS. 55 and 56. In the embodiment shown, the cables 650 are crimped to hypotubes 656 provided inside the tool shaft 602.

Figure 59:
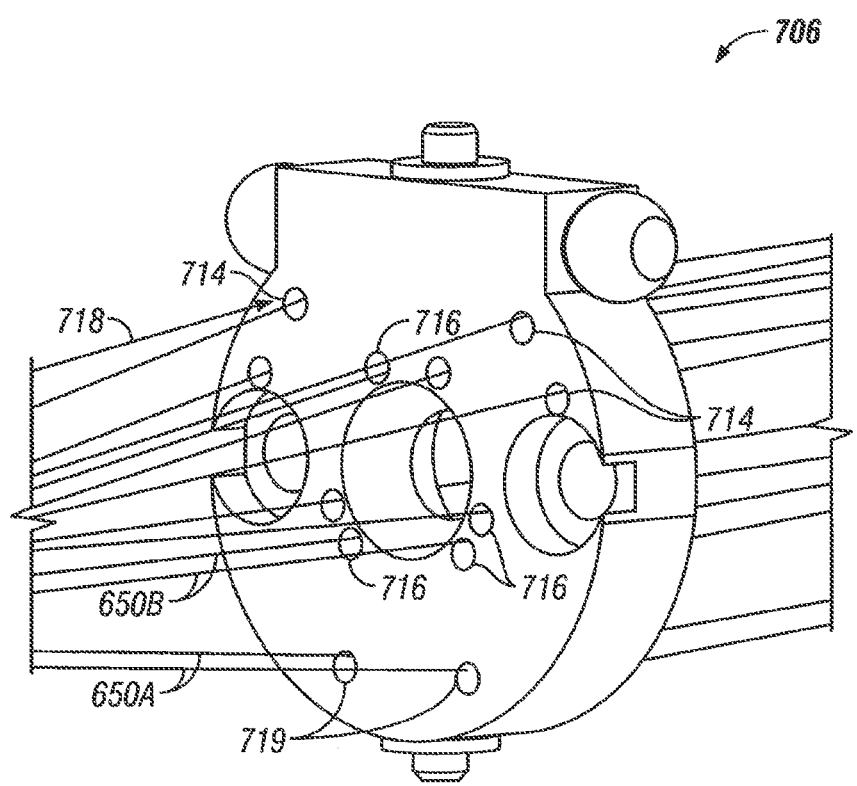
FIG. 59 is a perspective view of the gimbal plate of the actuator of FIG. 55.

FIGS. 57-63 show a gimbal mechanism 700 in the back end of the tool. The gimbal mechanism 700 is more compact than the gimbal mechanism comprising the gimbal plate 302 and parallel linkage mechanism 340 of FIGS. 35-40. The gimbal mechanism 700 includes another gimbal member or ring 702 that is mounted to rotate around an axis 704. A gimbal plate or actuator plate 706 is mounted to the outer ring 700 to rotate around an orthogonal axis 708. A lock plate 710 is placed over the gimbal plate 706. As seen in FIG. 59, the cables 650 from the wrist 600 are inserted through twelve cable holes 714, 716 of the gimbal plate 706, and pulled substantially straight back along arrow 716 toward the proximal end of the back end of the tool. The gimbal plate 706 includes six large radius apertures 714 for receiving distal cables 650A and six small radius apertures 716 for receiving medial cables 650B. The gimbal plate 706 has a first actuator connection 718 and a second actuator connection 719 for connecting to actuator links, as described below.

Figure 60:
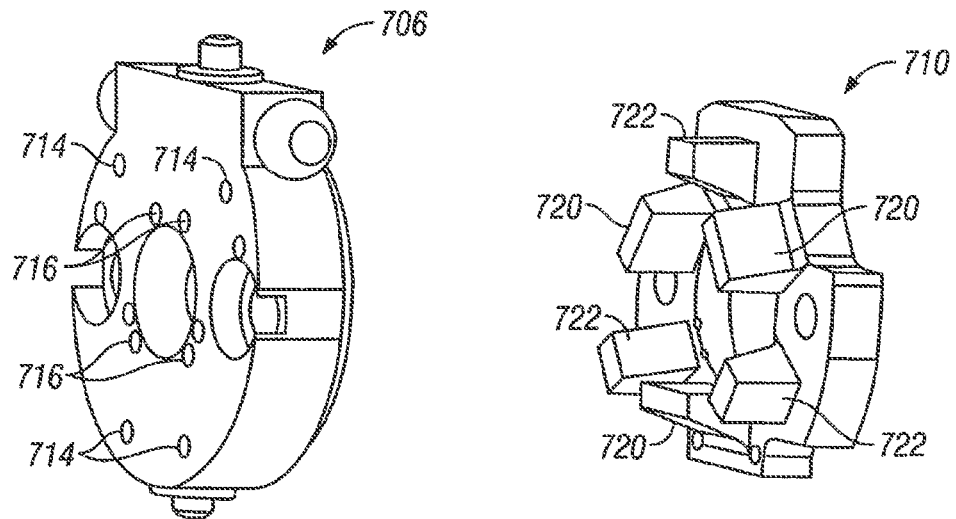
FIGS. 60-62 are exploded perspective views of the gimbaled cable actuator of FIG. 55.
Figure 61:
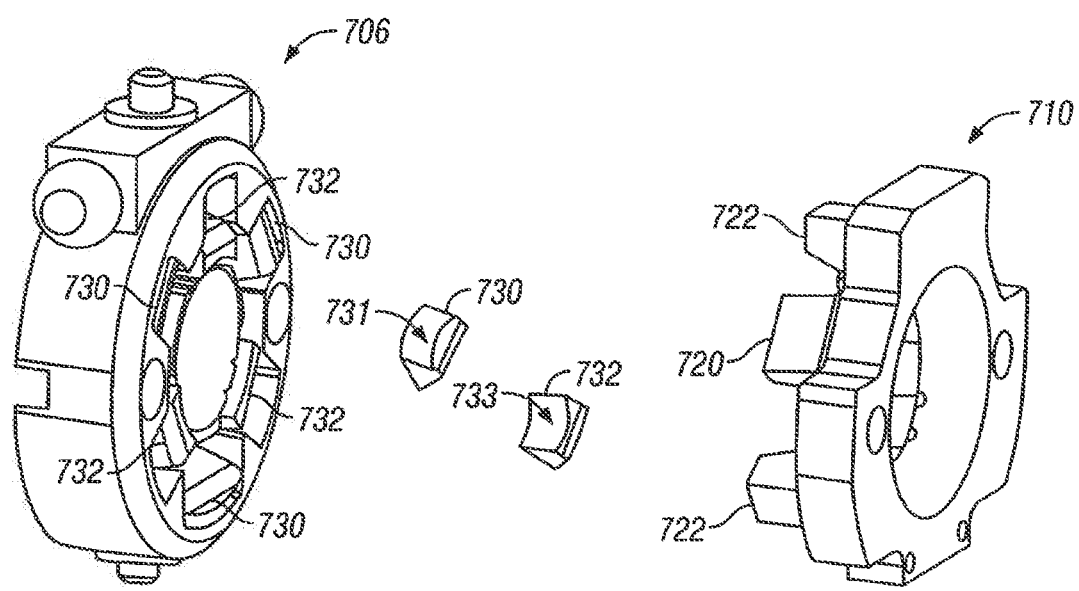

FIGS. 60 and 61 show the gimbal plate 706 and the lock plate 710 prior to assembly. The lock plate 710 is used to lock the cables 650A, 650B in place by moving wedges against the cables 650. As best seen in FIG. 60, the lock plate has three outward wedges 720 with radially outward facing wedge surfaces and three inward wedges 722 with radially inward facing wedge surface, which are alternately arranged around the lock plate 710. The gimbal plate 706 has corresponding loose or movable wedges that mate with the fixed wedges 720, 722 of the lock plate 710. As best seen in FIG. 61, the gimbal plate 706 includes three movable inward wedges 730 with radially inward facing wedge surfaces and curved outward surfaces 731, and three movable outward wedges 732 with radially outward facing wedge surfaces and curved inward surface 733. These movable wedges 730, 732 are alternately arranged and inserted into slots provided circumferentially around the gimbal plate 706.

Figure 62:
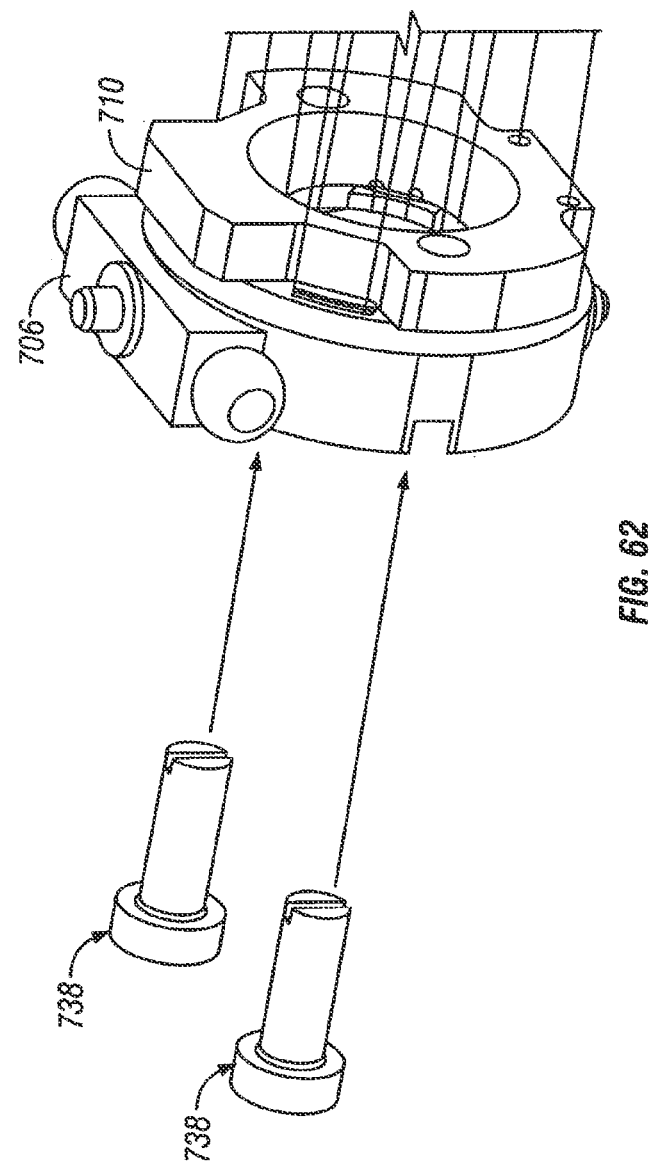
Figure 63:
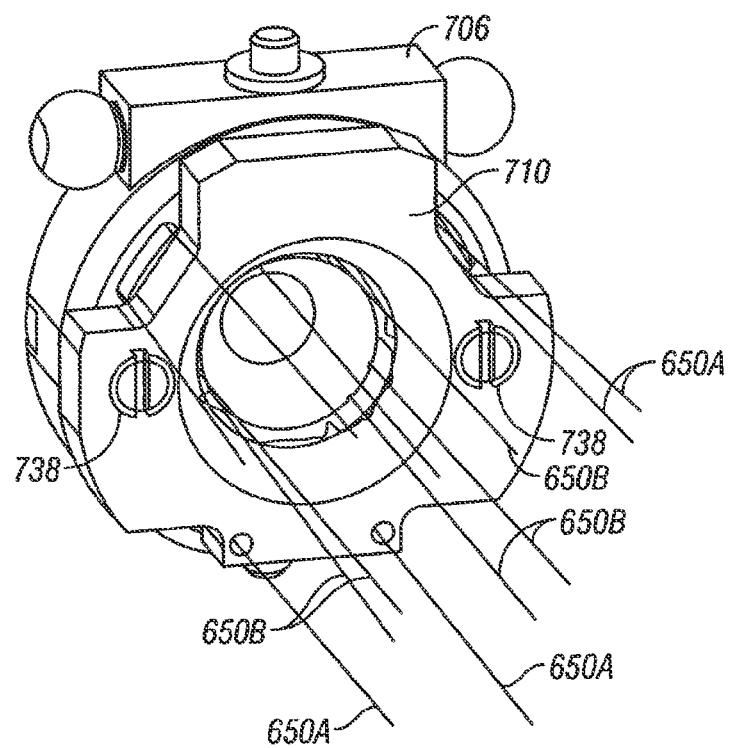
FIG. 63 is another perspective view of the gimbaled cable actuator of FIG. 55.
Figure 64:
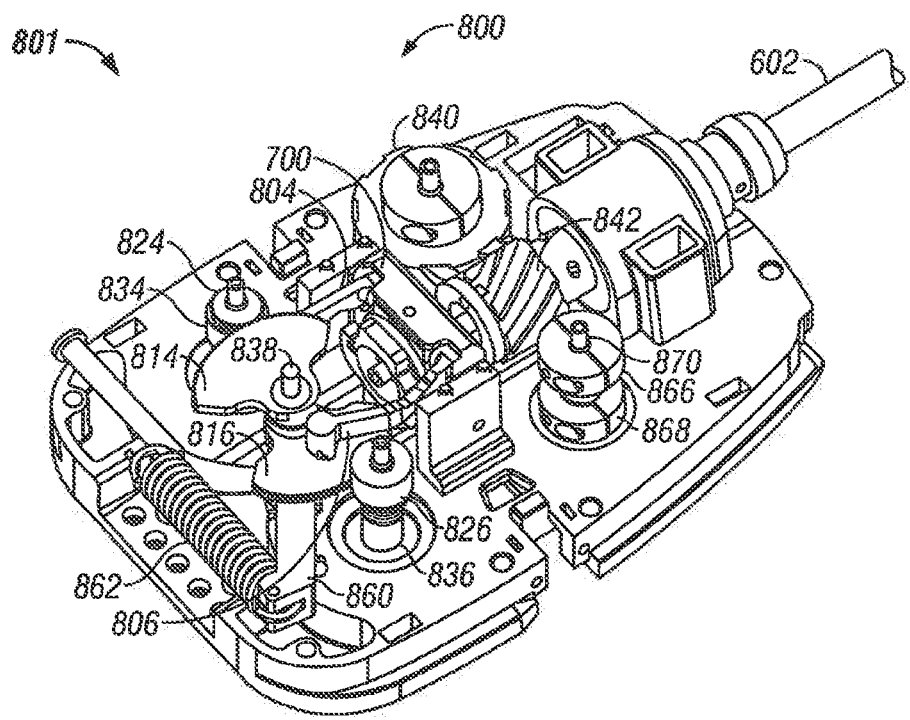
FIGS. 64-67 are perspective views of the back end according to another embodiment.

The lock plate 710 is assembled with the gimbal plate 706 after the cables 650 are inserted through the cable holes 714, 716 of the gimbal plate 706. As the lock plate 710 is moved toward the gimbal plate 706, the three outward wedges 720 of the lock plate 720 mate with the three movable inward wedges 730 in the slots of the gimbal plate 706 to push the movable inward wedges 730 radially outward against the six distal cables 650A extending through the six large radius apertures 714, which are captured between the curved outward surfaces 731 of the wedges 730 and the gimbal plate wall. The three inward wedges 722 of the lock plate 720 mate with the three movable outward wedges 732 in the slots of the gimbal plate 706 to push the movable outward wedges 732 radially inward against the six medial cables 650B extending through the six small radius apertures 716, which are captured between the curved inward surfaces 733 of the wedges 732 and the gimbal plate wall. As seen in FIGS. 62 and 63, the lock plate 710 is attached to the gimbal plate 706 using fasteners 738 such as threaded bolts or the like, which may be inserted from the gimbal plate 706 into the lock plate 710, or vice versa. In this embodiment of crimping all cables 650 by attaching the lock plate 710 to the gimbal plate 706, the cable tension is not affected by the termination method.

The gimbaled cable actuator 800 incorporating the gimbal mechanism 700 as illustrated in the back end 801 FIGS. 64-67 is similar to the gimbaled cable actuator 300 of FIGS. 32-40, but are rearranged and reconfigured to be more compact and efficient. The gimbaled cable actuator 800 is mounted on a lower housing member of the back end and the upper housing member is removed to show the internal details.

The gimbal plate 706 of the gimbal mechanism 700 is moved by a first actuator link 804 rotatably coupled to the first actuator connection 718 of the gimbal plate 706, and a second actuator link 806 rotatably coupled to the second actuator connection 719 of the gimbal plate 706, to produce pitch and yaw rotations. The rotatable coupling at the first actuator connection 718 and the second actuator connection 719 may be ball-in-socket connections. The actuator links 804, 806 are driven to move generally longitudinally by first and second follower gear quadrants 814, 816, respectively, which are rotatably coupled with the actuator links 804, 806 via pivot joints. The gear quadrants 814, 816 are rotated by first and second drive gears 824, 826, respectively, which are in turn actuated by drive spools 834, 836. The gear quadrants 814, 816 rotate around a common pivot axis 838. The arrangement is more compact than that of FIGS. 32-40. The first and second actuator links 804, 806 move in opposite directions to produce a yaw rotation of the gimbal plate 706, and move together in the same direction to produce a pitch rotation of the gimbal plate 706. Mixed pitch and yaw rotations result from adjusting the mixed movement of the actuator links 804, 806. Helical drive gear 840 and follower gear 842 are used to produce row rotation for improved efficiency and cost-effectiveness.

Figure 65:
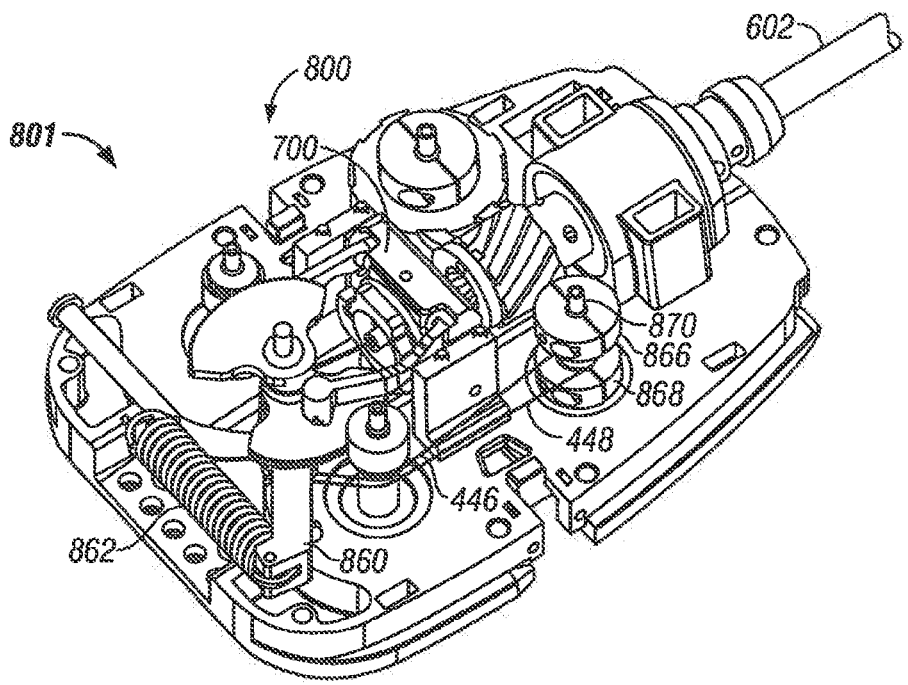
Figure 66:
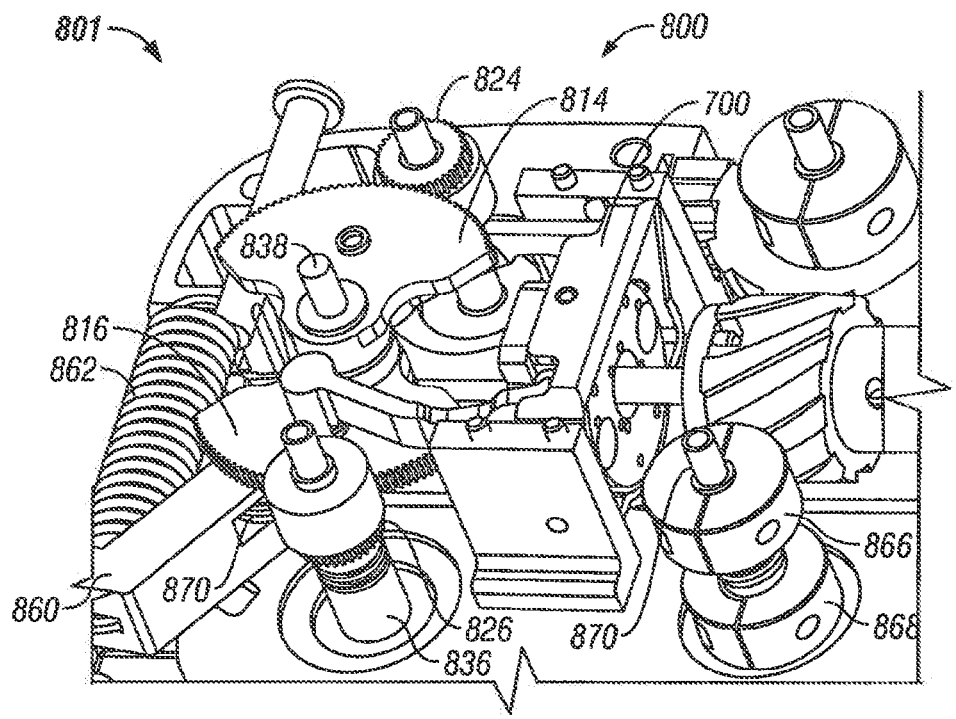
Figure 67:
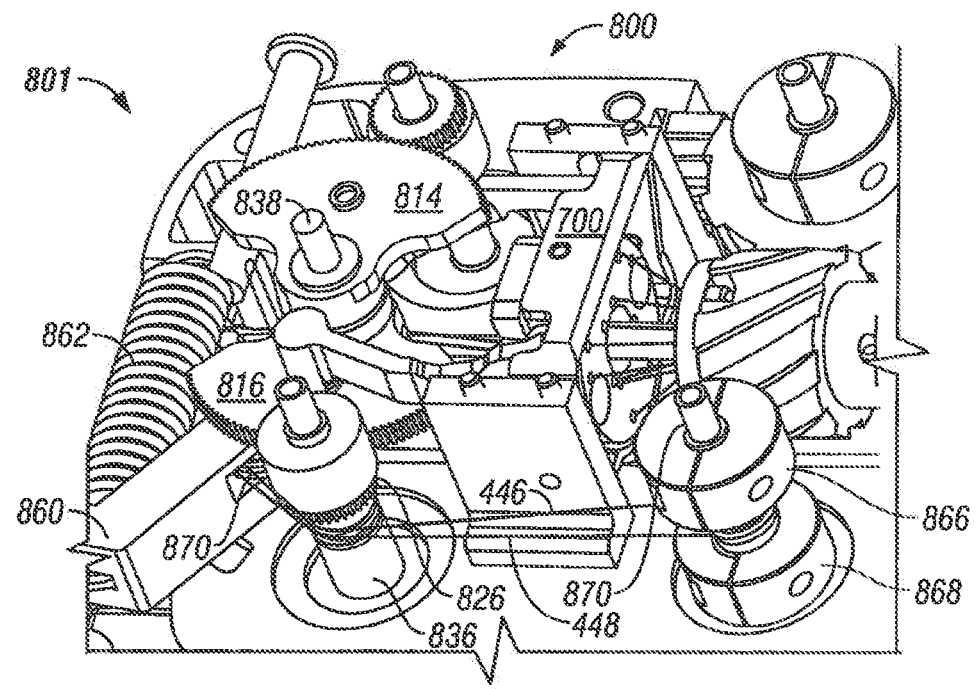

The back end 801 structure of FIGS. 64-67 provides an alternate way of securing and tensioning the cables, including the support cables 462, 464 for holding the grip support to the wrist (see FIGS. 38 and 38A), and grip actuation cables 446, 448 for actuating the opening and closing of the grip end effector (see FIG. 39). The support cables 462, 464 are clamped to an arm 860 which pivots around the pivot axis 838 and is biased by a cable tensioning spring 862. The spring 862 biases the arm 860 to apply tension to the support cables 462, 464 to hold the grip support tightly to the wrist (see FIGS. 38, 38A). The grip actuation cables 446, 448 extend around pulleys 870 (FIG. 66) connected to the spring-biased arm 860, and terminate at a pair of hub clamps 866, 868 provided along the motor input shaft 870, as best seen in FIGS. 65 and 67. The actuation cables 446, 448 are tensioned by applying a torque to the hub clamps 866, 868.

Figure 68C:
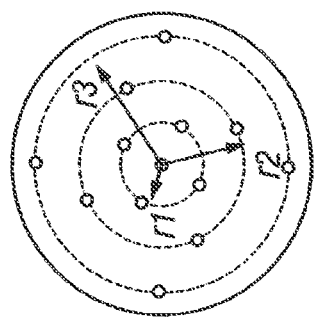
FIG. 68C is a schematic view of a cable actuator plate according to another embodiment.
Figure 68B:
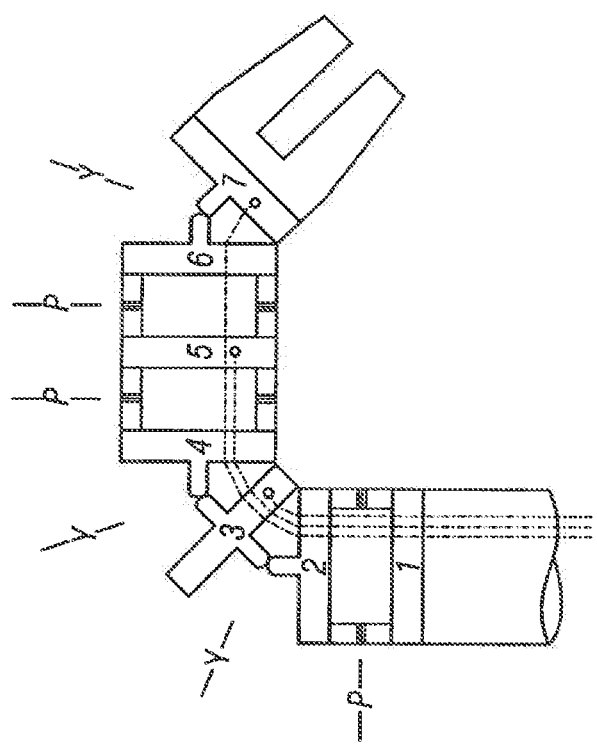
FIG. 68B is an elevational view of a bent wrist.
Figure 68A:
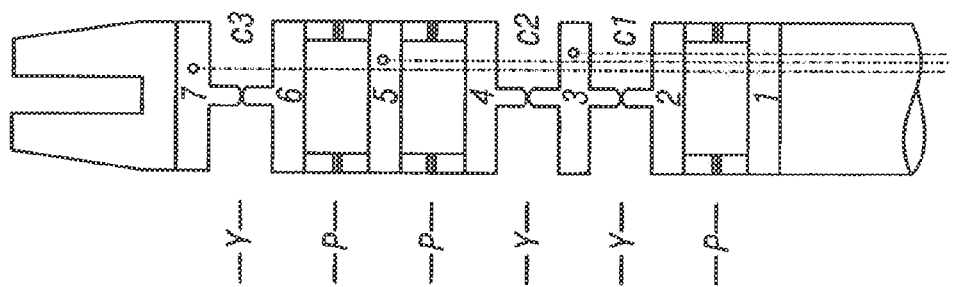
FIG. 68A is an elevational view of a straight wrist according to another embodiment.

FIGS. 68A, 68B, and 68C illustrate schematically a PPMD wrist embodiment and corresponding actuator plate having aspects of the invention, wherein the wrist includes more than five segments or disks, and has more than one medial disk with cable termination. The PPMD wrist shown in this example has 7 disks (numbered 1-7 from proximal shaft end disk to distal end effector support disk), separated by 6 pivotal couplings in a P,YY,PP,Y configuration. Three exemplary cable paths are shown, for cable sets c1, c2 and c3, which terminate at medial disks 3, 5 and 7 respectively. FIG. 68A shows the wrist in a straight conformation, and FIG. 68B shows the wrist in a yaw-deflected or bent conformation. The wrist may similarly be deflected in pitch (into or out of page), or a combination of these. Except for the number of segments and cable sets, the wrist shown is generally similar to the embodiment shown in FIGS. 17-24.

The wrist shown is of the type having at least a pair of generally parallel adjacent axes (e.g., . . . YPPY . . . or . . . PYYP . . . ), but may alternatively be configured with a PY,PY,PY alternating perpendicular axes arrangement. Still further alternative embodiments may have combination configurations of inter-disk couplings, such as PYYP,YP and the like. The wrist illustrated has a constant segment length and sequentially repeated pivot axes orientations. In more general alternative exemplary embodiments, the "Y" and "P" axes need not be substantially perpendicular to each other and need not be substantially perpendicular to the centerline, and the sequential segments need not be of a constant length.

FIG. 68C shows schematically the cable actuator plate layout, including cable set connections at r1, r2 and r3, corresponding to cable sets c1, c2 and c3 respectively. Four connections are shown per cable set, but the number may be 3, and may be greater than 4.

In more general form, alternative PPMD wrist embodiment and corresponding actuator plates having aspects of the invention may be configured as follows: Where N represents the number of disk segments (including end disks), the number of cable termination medial disks M may be: $M=(N-3)/2$. The number of cable sets and corresponding actuator plate "lever arm" radii, including the distal cable set connections, is $M+1$.

In general, the "constant velocity" segment arrangement described previously is analogous to an even-numbered sequence of universal-joint-like coupling pairs disposed back-to-front and front-to-back in alternation. For example, a YP,PY or YP,PY,YP,PY segment coupling sequence provides the "constant velocity" property. Thus may be achieved for arrangements wherein $N-1$ is a multiple of four, such as $N=5, 9$ and the like.

It may be seen that, for a given angular defection per coupling, the overall deflection of the wrist increases with increasing segment number (the example of FIG. 68B illustrates about 135 degrees of yaw).

The above-described arrangements of apparatus and methods are merely illustrative of applications of the principles of this invention and many other embodiments and modifications may be made without departing from the spirit and scope of the invention as defined in the claims. The scope of the invention should, therefore, be determined not with reference to the above description, but instead should be determined with reference to the appended claims along with their full scope of equivalents.

What is claimed is:

1. A tendon actuating assembly for a surgical instrument, wherein the instrument includes a shaft-like member having a distal working end for insertion into a patient's body through an aperture, the working end including at least one distal moveable member arranged to be actuated by at least one of a plurality of movable tendon elements, the actuating assembly comprising:

an actuator including a plurality of tendon engagement portions, each engagement portion receiving at least one of the plurality of tendons; and a drive mechanism drivingly coupled to the actuator so as to controllably pivot the actuator in the at least one degree of freedom, so as to move at least one of the tendons relative to the shaft-like member so as to actuate the distal moveable member;

wherein the actuator is pivotable about a pitch axis and a yaw axis; and the drive mechanism is configured to controllably pivot the actuator selectably about each of the pitch and yaw axes, so that movement of the actuator about either of the axes moves at least one tendon relative to the shaft-like member so as to actuate the at least one distal moveable member.

2. The actuating assembly of claim 1, wherein the actuator has a central axis, each of the first and second pivot axes intersect the central axis, and the plurality of engagement portions includes a first set of more than one engagement portions spaced apart from the central axis at about a first radial distance.

3. The actuating assembly of claim 2, wherein the plurality of engagement portions includes at least a second set of more than one engagement portions spaced apart from the central axis at about a second radial distance, the first radial distance being substantially different from the second radial distance.

4. The actuating assembly of claim 2, wherein the plurality of engagement portions includes a plurality of different sets of at least three engagement portions, each set spaced apart from the central axis at about a radial distance, the radial distance of each of the plurality of set being substantially different from the radial distance of each of the other sets.

5. The actuating assembly of claim 1, wherein the at least one distal movable member is a movable segment of a distal flexible member.

6. The actuating assembly of claim 1, wherein the drive mechanism is controllable by a robotic surgical system.

* * * * *